US012790651B2

(12) United States Patent
Eltoukhy et al.

(10) Patent No.: US 12,790,651 B2
(45) **Date of Patent: *Nov. 10, 2026**

(54) GENERATING ADJUSTED TEST RESULTS FROM MOLECULAR BARCODED CELL-FREE DNA SEQUENCE DATA

(71) Applicant: Guardant Health, Inc., Redwood City, CA (US)

(72) Inventors: Helmy Eltoukhy, Atherton, CA (US); AmirAli Talasaz, Menlo Park, CA (US)

(73) Assignee: GUARDANT HEALTH, INC., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/192,886

(22) Filed: Apr. 29, 2025

(65) Prior Publication Data

US 2026/0337692 A1 Oct. 29, 2026

Related U.S. Application Data

(63) Continuation of application No. 15/796,642, filed on Oct. 27, 2017, which is a continuation of application No. PCT/US2016/030301, filed on Apr. 29, 2016.

(60) Provisional application No. 62/155,755, filed on May 1, 2015.

(51) Int. Cl.
*C12Q 1/6886* (2018.01)

(52) U.S. Cl.
CPC ..... *C12Q 1/6886* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 4,725,536 | A | 2/1988 | Fritsch et al. |
| 4,942,124 | A | 7/1990 | Church |
| 5,124,246 | A | 6/1992 | Urdea et al. |
| 5,149,625 | A | 9/1992 | Church et al. |
| 5,200,314 | A | 4/1993 | Urdea |
| 5,424,186 | A | 6/1995 | Fodor et al. |
| 5,424,413 | A | 6/1995 | Hogan et al. |
| 5,445,934 | A | 8/1995 | Fodor et al. |
| 5,604,097 | A | 2/1997 | Brenner |
| 5,635,352 | A | 6/1997 | Urdea et al. |
| 5,635,400 | A | 6/1997 | Brenner |
| 5,648,245 | A | 7/1997 | Fire et al. |
| 5,654,413 | A | 8/1997 | Brenner |
| 5,656,731 | A | 8/1997 | Urdea |
| 5,658,737 | A | 8/1997 | Nelson et al. |
| 5,714,330 | A | 2/1998 | Brenner et al. |
| 5,744,305 | A | 4/1998 | Fodor et al. |
| 5,759,778 | A | 6/1998 | Li et al. |
| 5,763,175 | A | 6/1998 | Brenner |
| 5,800,992 | A | 9/1998 | Fodor et al. |
| 5,846,719 | A | 12/1998 | Brenner et al. |
| 5,854,033 | A | 12/1998 | Lizardi |
| 5,871,928 | A | 2/1999 | Fodor et al. |
| 5,925,525 | A | 7/1999 | Fodor et al. |
| 5,935,793 | A | 8/1999 | Wong |
| 5,952,170 | A | 9/1999 | Stroun et al. |
| 5,968,740 | A | 10/1999 | Fodor et al. |
| 5,981,176 | A | 11/1999 | Wallace |
| 5,981,179 | A | 11/1999 | Lorinez et al. |
| 6,013,445 | A | 1/2000 | Albrecht et al. |

(Continued)

FOREIGN PATENT DOCUMENTS

| | | |
|---|---|---|
| CN | 102933721 A | 2/2013 |
| EP | 0799897 B1 | 6/2006 |

(Continued)

OTHER PUBLICATIONS

Park, et al. Discovery of common Asian copy number variants using integrated high-resolution array CGH and massively parallel DNA sequencing. Nat Genet. May 2010;42(5):400-5. doi: 10.1038/ng.555. Epub Apr. 4, 2010.
Paweletz, C.P. et al. "Bias-corrected targeted next-generation sequencing for rapid, multiplexed detection of actionable alterations in cell-free DNA from advanced lung cancer patients" Clin Canc Res (2016) 22(4):915-922.
Phallen, J. et al. "Direct detection of early-stage cancers using circulating tumor DNA" Sci Trans Med (2017) vol. 9, Issue 403, eaan2415DOI: 10.1126/scitranslmed.aan2415.
Pihlak, et al. Rapid genome sequencing with short universal tiling probes. Nature Biotechnology, 26: 676-684 (2008).
Pinkel, et al. Comparative Genomic Hybridization. Annual Review of Genomics and Human Genetics, 6: 331-354 (2005).
Pleasance, et al. A small-cell lung cancer genome with complex signatures of tobacco exposure. Nature. Jan. 14, 2010;463(7278):184-90. doi: 10.1038/nature08629. Epub Dec. 16, 2009.

(Continued)

*Primary Examiner* — G. Steven Vanni
(74) *Attorney, Agent, or Firm* — Stephen W. Chen

(57) ABSTRACT

The present disclosure provides methods comprising: (a) ligating molecular barcodes to a plurality of cell-free DNA (cfDNA) molecules, wherein the plurality of cfDNA molecules are from a first cell-free biological sample from a subject; (b) ligating molecular barcodes to a second plurality of cfDNA molecules, wherein the second plurality of cfDNA molecules are from a second cell-free biological sample from the subject; (c) generating genetic data using a genetic analyzer, wherein the genetic data relates to genetic information of the subject; (d) receiving the genetic data from the genetic analyzer; (e) comparing the genetic data from the first cell-free biological sample to the genetic data from the second cell-free biological sample to produce an adjusted test result, wherein the adjusted test result is adjusted based upon whether the genetic data from the first cell-free biological sample corroborates or conflicts with the genetic data from the second cell-free biological sample and (f) outputting the adjusted test result into computer memory. This abstract is intended as a scanning tool for purposes of searching in the particular art and is not intended to be limiting of the present invention.

27 Claims, 13 Drawing Sheets

(56) References Cited

U.S. PATENT DOCUMENTS

| | | | |
|---|---|---|---|
| 6,020,124 | A | 2/2000 | Sorenson |
| 6,040,138 | A | 3/2000 | Lockhart et al. |
| 6,046,005 | A | 4/2000 | Ju et al. |
| 6,060,596 | A | 5/2000 | Lerner et al. |
| 6,117,631 | A | 9/2000 | Nilsen |
| 6,124,092 | A | 9/2000 | O'Neill et al. |
| 6,138,077 | A | 10/2000 | Brenner |
| 6,140,489 | A | 10/2000 | Brenner |
| 6,172,214 | B1 | 1/2001 | Brenner |
| 6,197,506 | B1 | 3/2001 | Fodor et al. |
| 6,235,475 | B1 | 5/2001 | Brenner et al. |
| 6,242,186 | B1 | 6/2001 | Salonen |
| 6,268,152 | B1 | 7/2001 | Fodor et al. |
| 6,284,460 | B1 | 9/2001 | Fodor et al. |
| 6,300,077 | B1 | 10/2001 | Shuber et al. |
| 6,309,822 | B1 | 10/2001 | Fodor et al. |
| 6,309,823 | B1 | 10/2001 | Cronin et al. |
| 6,326,148 | B1 | 12/2001 | Pauletti et al. |
| 6,355,431 | B1 | 3/2002 | Chee et al. |
| 6,355,432 | B1 | 3/2002 | Fodor et al. |
| 6,395,491 | B1 | 5/2002 | Fodor et al. |
| 6,406,848 | B1 | 6/2002 | Bridgham et al. |
| 6,440,667 | B1 | 8/2002 | Fodor et al. |
| 6,440,706 | B1 | 8/2002 | Vogelstein et al. |
| 6,451,536 | B1 | 9/2002 | Fodor et al. |
| 6,458,530 | B1 | 10/2002 | Morris et al. |
| 6,468,744 | B1 | 10/2002 | Cronin et al. |
| 6,489,114 | B2 | 12/2002 | Laayoun et al. |
| 6,492,121 | B2 | 12/2002 | Kurane et al. |
| 6,498,012 | B2 | 12/2002 | Laken |
| 6,503,718 | B2 | 1/2003 | Shuber et al. |
| 6,512,105 | B1 | 1/2003 | Hogan et al. |
| 6,514,699 | B1 | 2/2003 | O'Neill et al. |
| 6,544,739 | B1 | 4/2003 | Fodor et al. |
| 6,551,784 | B2 | 4/2003 | Fodor et al. |
| 6,576,424 | B2 | 6/2003 | Fodor et al. |
| 6,582,908 | B2 | 6/2003 | Fodor et al. |
| 6,586,177 | B1 | 7/2003 | Shuber |
| 6,600,996 | B2 | 7/2003 | Webster et al. |
| 6,629,040 | B1 | 9/2003 | Goodlett et al. |
| 6,653,077 | B1 | 11/2003 | Brenner |
| 6,753,147 | B2 | 6/2004 | Vogelstein et al. |
| 6,849,403 | B1 | 2/2005 | Shuber |
| 6,849,404 | B2 | 2/2005 | Park et al. |
| 6,852,488 | B2 | 2/2005 | Fodor et al. |
| 6,858,412 | B2 | 2/2005 | Willis et al. |
| 6,964,846 | B1 | 11/2005 | Shuber |
| 7,163,789 | B2 | 1/2007 | Chen et al. |
| 7,208,275 | B2 | 4/2007 | Gocke et al. |
| 7,410,764 | B2 | 8/2008 | Gocke et al. |
| 7,424,368 | B2 | 9/2008 | Huang et al. |
| 7,424,371 | B2 | 9/2008 | Kamentsky |
| 7,537,897 | B2 | 5/2009 | Brenner et al. |
| 7,700,286 | B2 | 4/2010 | Stroun et al. |
| 7,704,687 | B2 | 4/2010 | Wang et al. |
| 7,727,720 | B2 | 6/2010 | Dhallan |
| 7,803,929 | B2 | 9/2010 | Melkonyan et al. |
| 7,811,757 | B2 | 10/2010 | Shuber |
| 7,822,555 | B2 | 10/2010 | Huang et al. |
| 7,824,889 | B2 | 11/2010 | Vogelstein et al. |
| 7,838,647 | B2 | 11/2010 | Hahn et al. |
| 7,915,015 | B2 | 3/2011 | Vogelstein et al. |
| 7,935,487 | B2 | 5/2011 | Gocke et al. |
| 7,937,225 | B2 | 5/2011 | Mishra et al. |
| 7,957,913 | B2 | 6/2011 | Chinitz et al. |
| 7,972,817 | B2 | 7/2011 | Kopreski |
| 7,981,612 | B2 | 7/2011 | Shuber et al. |
| 8,094,312 | B2 | 1/2012 | Ulmer |
| 8,168,385 | B2 | 5/2012 | Brenner |
| 8,195,415 | B2 | 6/2012 | Fan et al. |
| 8,209,130 | B1 | 6/2012 | Kennedy et al. |
| 8,216,789 | B2 | 7/2012 | Disis et al. |
| 8,236,532 | B2 | 8/2012 | Ronaghi et al. |
| 8,361,726 | B2 | 1/2013 | Gocke et al. |
| 8,383,338 | B2 | 2/2013 | Kitzman et al. |
| 8,383,345 | B2 | 2/2013 | Shendure et al. |
| 8,455,193 | B2 | 6/2013 | Travers et al. |
| 8,470,996 | B2 | 6/2013 | Brenner |
| 8,481,292 | B2 | 7/2013 | Casbon et al. |
| 8,603,749 | B2 | 12/2013 | Gillevet |
| 8,685,678 | B2 | 4/2014 | Casbon et al. |
| 8,704,165 | B2 | 4/2014 | Huang |
| 8,715,967 | B2 | 5/2014 | Casbon et al. |
| 8,722,368 | B2 | 5/2014 | Casbon et al. |
| 8,728,766 | B2 | 5/2014 | Casbon et al. |
| 8,741,606 | B2 | 6/2014 | Casbon et al. |
| 8,775,092 | B2 | 7/2014 | Colwell et al. |
| 8,835,358 | B2 | 9/2014 | Fodor et al. |
| 9,018,365 | B2 | 4/2015 | Brenner |
| 9,085,798 | B2 | 7/2015 | Chee |
| 9,260,753 | B2 | 2/2016 | Xie et al. |
| 9,340,830 | B2 | 5/2016 | Lipson et al. |
| 9,376,719 | B2 | 6/2016 | Eijk et al. |
| 9,404,156 | B2 | 8/2016 | Hicks et al. |
| 9,598,731 | B2 | 3/2017 | Talasaz |
| 9,834,822 | B2 | 12/2017 | Talasaz |
| 9,840,743 | B2 | 12/2017 | Talasaz |
| 9,920,366 | B2 | 3/2018 | Eltoukhy et al. |
| 10,876,172 | B2 | 12/2020 | Talasaz |
| 2001/0053519 | A1 | 12/2001 | Fodor et al. |
| 2002/0034760 | A1 | 3/2002 | Kindness et al. |
| 2002/0072058 | A1 | 6/2002 | Voelker et al. |
| 2003/0003490 | A1 | 1/2003 | Fan et al. |
| 2003/0049616 | A1 | 3/2003 | Brenner et al. |
| 2003/0104436 | A1 | 6/2003 | Morris et al. |
| 2003/0152490 | A1 | 8/2003 | Trulson et al. |
| 2003/0165978 | A1 | 9/2003 | Firth et al. |
| 2003/0186251 | A1 | 10/2003 | Dunn et al. |
| 2003/0207300 | A1 | 11/2003 | Matray et al. |
| 2004/0096892 | A1 | 5/2004 | Wang et al. |
| 2004/0146901 | A1 | 7/2004 | Morris et al. |
| 2004/0157243 | A1 | 8/2004 | Huang et al. |
| 2004/0209299 | A1 | 10/2004 | Pinter et al. |
| 2004/0259118 | A1 | 12/2004 | Macevicz |
| 2005/0164241 | A1 | 7/2005 | Hahn et al. |
| 2005/0221314 | A1 | 10/2005 | Berlin et al. |
| 2005/0250147 | A1 | 11/2005 | Macevicz |
| 2006/0035258 | A1 | 2/2006 | Tadakamalla et al. |
| 2006/0046258 | A1 | 3/2006 | Lapidus et al. |
| 2006/0073506 | A1 | 4/2006 | Christians et al. |
| 2006/0211030 | A1 | 9/2006 | Brenner |
| 2007/0020640 | A1 | 1/2007 | McCloskey et al. |
| 2007/0065823 | A1 | 3/2007 | Dressman et al. |
| 2007/0111233 | A1 | 5/2007 | Bianchi et al. |
| 2007/0128724 | A1 | 6/2007 | Miles et al. |
| 2007/0172839 | A1 | 7/2007 | Smith et al. |
| 2007/0172873 | A1 | 7/2007 | Brenner et al. |
| 2008/0014146 | A1 | 1/2008 | Hoff et al. |
| 2008/0124721 | A1 | 5/2008 | Fuchs et al. |
| 2008/0161420 | A1 | 7/2008 | Shuber |
| 2008/0261204 | A1 | 10/2008 | Lexow |
| 2008/0293055 | A1 | 11/2008 | Freeman et al. |
| 2009/0029377 | A1 | 1/2009 | Lo et al. |
| 2009/0087847 | A1 | 4/2009 | Lo et al. |
| 2009/0098547 | A1 | 4/2009 | Ghosh |
| 2009/0105959 | A1 | 4/2009 | Braverman et al. |
| 2009/0162836 | A1 | 6/2009 | Widschwendter |
| 2009/0298075 | A1 | 12/2009 | Travers et al. |
| 2009/0298709 | A1 | 12/2009 | Ma |
| 2009/0317818 | A1 | 12/2009 | Ehrich et al. |
| 2010/0041048 | A1 | 2/2010 | Diehl et al. |
| 2010/0062494 | A1 | 3/2010 | Church et al. |
| 2010/0069250 | A1 | 3/2010 | White et al. |
| 2010/0143932 | A1 | 6/2010 | Lapidus |
| 2010/0166744 | A1 | 7/2010 | Wong |
| 2010/0196898 | A1 | 8/2010 | Sugarbaker et al. |
| 2010/0323348 | A1 | 12/2010 | Hamady et al. |
| 2010/0330571 | A1 | 12/2010 | Robins et al. |
| 2011/0014607 | A1 | 1/2011 | Jirtle et al. |
| 2011/0160078 | A1 | 6/2011 | Fodor et al. |
| 2011/0160290 | A1 | 6/2011 | Tewari |
| 2011/0171640 | A1 | 7/2011 | Bhatt et al. |
| 2011/0177512 | A1 | 7/2011 | Shuber |
| 2011/0183330 | A1 | 7/2011 | Lo et al. |

(56) References Cited

U.S. PATENT DOCUMENTS

| | | | |
|---|---|---|---|
| 2011/0201507 | A1 | 8/2011 | Rava et al. |
| 2011/0230358 | A1 | 9/2011 | Rava |
| 2011/0230360 | A1 | 9/2011 | Stephan et al. |
| 2011/0245482 | A1 | 10/2011 | Hahn et al. |
| 2011/0257896 | A1 | 10/2011 | Dowds et al. |
| 2011/0264376 | A1 | 10/2011 | Chinitz et al. |
| 2011/0275084 | A1 | 11/2011 | Byron et al. |
| 2011/0281736 | A1 | 11/2011 | Drmanac et al. |
| 2012/0003637 | A1 | 1/2012 | Lo et al. |
| 2012/0034685 | A1 | 2/2012 | Sparks et al. |
| 2012/0046877 | A1 | 2/2012 | Hyland et al. |
| 2012/0053073 | A1 | 3/2012 | Kassis |
| 2012/0059594 | A1 | 3/2012 | Hatchwell et al. |
| 2012/0065081 | A1 | 3/2012 | Chee |
| 2012/0095697 | A1 | 4/2012 | Halpern et al. |
| 2012/0100548 | A1 | 4/2012 | Rava et al. |
| 2012/0164630 | A1 | 6/2012 | Porreca et al. |
| 2012/0208706 | A1 | 8/2012 | Downing et al. |
| 2012/0214163 | A1 | 8/2012 | Sugarbaker et al. |
| 2012/0214678 | A1 | 8/2012 | Rava et al. |
| 2012/0220478 | A1 | 8/2012 | Shaffer |
| 2012/0231479 | A1 | 9/2012 | Puskas et al. |
| 2012/0238464 | A1 | 9/2012 | Koi et al. |
| 2012/0270212 | A1 | 10/2012 | Rabinowitz et al. |
| 2012/0316074 | A1 | 12/2012 | Saxonov |
| 2013/0005585 | A1 | 1/2013 | Anderson et al. |
| 2013/0017958 | A1 | 1/2013 | Benz et al. |
| 2013/0022977 | A1 | 1/2013 | Lapidus et al. |
| 2013/0029852 | A1 | 1/2013 | Rava et al. |
| 2013/0034546 | A1 | 2/2013 | Rava et al. |
| 2013/0040824 | A1 | 2/2013 | Lo et al. |
| 2013/0053256 | A1 | 2/2013 | Hubbell |
| 2013/0060483 | A1 | 3/2013 | Struble et al. |
| 2013/0078626 | A1 | 3/2013 | Wasserstrom et al. |
| 2013/0085681 | A1 | 4/2013 | Deciu et al. |
| 2013/0102485 | A1 | 4/2013 | Lee |
| 2013/0102487 | A1 | 4/2013 | Cos et al. |
| 2013/0116127 | A1 | 5/2013 | Schuetz et al. |
| 2013/0116130 | A1 | 5/2013 | Fu et al. |
| 2013/0122499 | A1 | 5/2013 | Morris et al. |
| 2013/0130923 | A1 | 5/2013 | Ehrich et al. |
| 2013/0137588 | A1 | 5/2013 | Shendure et al. |
| 2013/0143747 | A1 | 6/2013 | Gutin et al. |
| 2013/0210643 | A1 | 8/2013 | Casbon et al. |
| 2013/0210645 | A1 | 8/2013 | Volgelstein et al. |
| 2013/0224743 | A1 | 8/2013 | Casbon et al. |
| 2013/0237431 | A1 | 9/2013 | Lo et al. |
| 2013/0237458 | A1 | 9/2013 | Casbon et al. |
| 2013/0260381 | A1 | 10/2013 | Ramakrishnan |
| 2013/0267424 | A1 | 10/2013 | Casbon et al. |
| 2013/0338933 | A1 | 12/2013 | Deciu et al. |
| 2014/0011694 | A1 | 1/2014 | Couronne |
| 2014/0065609 | A1 | 3/2014 | Hicks et al. |
| 2014/0065630 | A1 | 3/2014 | Bubnoff et al. |
| 2014/0066317 | A1 | 3/2014 | Talasaz |
| 2014/0100121 | A1 | 4/2014 | Lo et al. |
| 2014/0200147 | A1 | 7/2014 | Bartha et al. |
| 2014/0242588 | A1 | 8/2014 | Boom et al. |
| 2014/0274731 | A1 | 9/2014 | Raymond et al. |
| 2014/0274740 | A1 | 9/2014 | Srinivasan et al. |
| 2014/0296094 | A1 | 10/2014 | Domanus |
| 2014/0303008 | A1 | 10/2014 | Schutz et al. |
| 2014/0336943 | A1 | 11/2014 | Pellini et al. |
| 2014/0350130 | A1 | 11/2014 | Sanborn et al. |
| 2015/0004158 | A1 | 1/2015 | Shipp et al. |
| 2015/0024950 | A1 | 1/2015 | Bielas et al. |
| 2015/0044687 | A1 | 2/2015 | Schmitt et al. |
| 2015/0050647 | A1 | 2/2015 | Luo et al. |
| 2015/0051085 | A1 | 2/2015 | Vogelstein et al. |
| 2015/0065352 | A1 | 3/2015 | Faham et al. |
| 2015/0065358 | A1 | 3/2015 | Comstock et al. |
| 2015/0087535 | A1 | 3/2015 | Patel |
| 2015/0167069 | A1 | 6/2015 | Schutz et al. |
| 2015/0275289 | A1 | 10/2015 | Otwinowski et al. |
| 2015/0299812 | A1 | 10/2015 | Talasaz |
| 2015/0329917 | A1 | 11/2015 | Shuber |
| 2015/0344970 | A1 | 12/2015 | Vogelstein et al. |
| 2015/0366866 | A1 | 12/2015 | Ali et al. |
| 2015/0368708 | A1 | 12/2015 | Talasaz |
| 2016/0002739 | A1 | 1/2016 | Schütz et al. |
| 2016/0002741 | A1 | 1/2016 | Kitano et al. |
| 2016/0024576 | A1 | 1/2016 | Chee |
| 2016/0026758 | A1 | 1/2016 | Jabara et al. |
| 2016/0032396 | A1 | 2/2016 | Diehn et al. |
| 2016/0040229 | A1 | 2/2016 | Talasaz et al. |
| 2016/0046986 | A1 | 2/2016 | Eltoukhy et al. |
| 2016/0053301 | A1 | 2/2016 | Raymond et al. |
| 2016/0060691 | A1 | 3/2016 | Giresi et al. |
| 2016/0071432 | A1 | 3/2016 | Kurowski et al. |
| 2016/0115553 | A1 | 4/2016 | Stephan et al. |
| 2016/0130649 | A1 | 5/2016 | Xie et al. |
| 2016/0251704 | A1 | 9/2016 | Talasaz et al. |
| 2016/0273049 | A1 | 9/2016 | Velculescu et al. |
| 2016/0289753 | A1 * | 10/2016 | Osborne ................ G16B 30/20 |
| 2016/0319345 | A1 | 11/2016 | Gnerre et al. |
| 2016/0333417 | A1 | 11/2016 | Talasaz |
| 2016/0376647 | A1 | 12/2016 | Travers et al. |
| 2017/0051347 | A1 | 2/2017 | Vogelstein et al. |
| 2017/0073774 | A1 | 3/2017 | Lo et al. |
| 2017/0145516 | A1 | 5/2017 | Kopetz et al. |
| 2017/0159120 | A1 | 6/2017 | Eijk et al. |
| 2017/0211143 | A1 | 7/2017 | Shendure et al. |
| 2017/0218459 | A1 | 8/2017 | Talasaz et al. |
| 2017/0218460 | A1 | 8/2017 | Talasaz |
| 2017/0260590 | A1 | 9/2017 | Eltoukhy et al. |
| 2018/0023125 | A1 | 1/2018 | Talasaz et al. |
| 2018/0135044 | A1 | 5/2018 | Sausen et al. |
| 2018/0251848 | A1 | 9/2018 | Diehn et al. |
| 2020/0299785 | A1 | 9/2020 | Talasaz |

FOREIGN PATENT DOCUMENTS

| | | | |
|---|---|---|---|
| EP | 1647600 | A2 | 6/2006 |
| EP | 2110442 | A1 | 10/2009 |
| EP | 3070177 | A1 | 9/2016 |
| EP | 3178941 | A1 | 6/2017 |
| WO | 1997007241 | A1 | 2/1997 |
| WO | 1997010365 | A1 | 3/1997 |
| WO | 1999028505 | A1 | 6/1999 |
| WO | 2000058516 | A2 | 10/2000 |
| WO | 2002056014 | A2 | 7/2002 |
| WO | 2005059692 | A2 | 6/2005 |
| WO | 2005080604 | A2 | 9/2005 |
| WO | 2005111242 | A2 | 11/2005 |
| WO | 2006102264 | A1 | 9/2006 |
| WO | 2007037678 | A2 | 4/2007 |
| WO | 2008070144 | A2 | 6/2008 |
| WO | 2008154317 | A1 | 12/2008 |
| WO | 2009152928 | A2 | 12/2009 |
| WO | 2011060240 | A1 | 5/2011 |
| WO | 2011087760 | A2 | 7/2011 |
| WO | 2011091046 | A1 | 7/2011 |
| WO | 2011103236 | A2 | 8/2011 |
| WO | 2011140510 | A2 | 11/2011 |
| WO | 2011155833 | A2 | 12/2011 |
| WO | 2012012693 | A2 | 1/2012 |
| WO | 2012014877 | A1 | 2/2012 |
| WO | 2012019200 | A2 | 2/2012 |
| WO | 2012028746 | A1 | 3/2012 |
| WO | 2012038839 | A2 | 3/2012 |
| WO | 2012042374 | A2 | 4/2012 |
| WO | 2012048341 | A1 | 4/2012 |
| WO | 2012054873 | A2 | 4/2012 |
| WO | 2012066451 | A1 | 5/2012 |
| WO | 2012088348 | A2 | 6/2012 |
| WO | 2012106559 | A1 | 8/2012 |
| WO | 2012129363 | A2 | 9/2012 |
| WO | 2012142213 | A2 | 10/2012 |
| WO | 2012103031 | A3 | 1/2013 |
| WO | 2013019075 | A2 | 2/2013 |
| WO | 2013033721 | A1 | 3/2013 |
| WO | 2013067001 | A1 | 5/2013 |
| WO | 2013106737 | A1 | 7/2013 |
| WO | 2013123442 | A1 | 8/2013 |

(56) References Cited

FOREIGN PATENT DOCUMENTS

| | | | |
|---|---|---|---|
| WO | 2013130512 | A2 | 9/2013 |
| WO | 2013130674 | A1 | 9/2013 |
| WO | 2013138510 | A1 | 9/2013 |
| WO | 2013142213 | A1 | 9/2013 |
| WO | 2013142389 | A1 | 9/2013 |
| WO | 2013148496 | A1 | 10/2013 |
| WO | 2013159035 | A2 | 10/2013 |
| WO | 2013173394 | A2 | 11/2013 |
| WO | 2013181170 | A1 | 12/2013 |
| WO | 2013188471 | A2 | 12/2013 |
| WO | 2013190441 | A2 | 12/2013 |
| WO | 2014004726 | A1 | 1/2014 |
| WO | 2014014497 | A1 | 1/2014 |
| WO | 2014015319 | A1 | 1/2014 |
| WO | 2014039556 | A1 | 3/2014 |
| WO | 2014093330 | A1 | 6/2014 |
| WO | 2014145078 | A1 | 9/2014 |
| WO | 2014149134 | A2 | 9/2014 |
| WO | 2014151117 | A1 | 9/2014 |
| WO | 2014152990 | A1 | 9/2014 |
| WO | 2015100427 | A1 | 7/2015 |
| WO | 2015159293 | A2 | 10/2015 |
| WO | 2015175705 | A1 | 11/2015 |
| WO | 2016015058 | A2 | 1/2016 |
| WO | 2016040901 | A1 | 3/2016 |
| WO | 2016179049 | A1 | 11/2016 |
| WO | 2017100441 | A1 | 6/2017 |
| WO | 2017181146 | A1 | 10/2017 |

OTHER PUBLICATIONS

Pollack, et al. Genome-wide analysis of DNA copy-number changes using cDNA microarrays. Nat Genet. Sep. 1999;23(1):41-6.

Qiu, et al. DNA sequence-based "bar codes" for tracking the origins of expressed sequence tags from a maize cDNA library constructed using multiple mRNA sources. Plant Physiol. Oct. 2003;133(2):475-81.

Quail, et al. A large genome center's improvements to the Illumina sequencing system. Nat Methods. Dec. 2008;5 (12):1005-10. doi: 10.1038/nmeth.1270.

Rand, et al. Headloop suppression PCR and its application to selective amplification of methylated DNA sequences. Nucleic Acids Res. Aug. 9, 2005;33(14):e127.

Ryan, et al. A prospective study of circulating mutant KRAS2 in the serum of patients with colorectal neoplasia: strong prognostic indicator in postoperative follow up. Gut. Jan. 2003;52(1):101-8.

Rygaard, et al. Abnormalities in structure and expression of the retinoblastoma gene in small cell lung cancer cell lines and xenografts in nude mice. Cancer Res. Sep. 1, 1990;50(17):5312-7.

Sanger, F. et al. "DNA sequencing with chain-terminating inhibitors" PNAS (1977) 74(12):5463-5467.

Schmitt, et al. Detection of ultra-rare mutations by next-generation sequencing. Proc Natl Acad Sci U S A. Sep. 4, 2012;109(36):14508-13. doi: 10.1073/pnas.1208715109. Epub Aug. 1, 2012.

Schwarzenbach, et al. A critical evaluation of loss of heterozygosity detected in tumor tissues, blood serum and bone marrow plasma from patients with breast cancer. Breast Cancer Res. 2007;9(5):R66.

Schwarzenbach, et al. Cell-free tumor DNA in blood plasma as a marker for circulating tumor cells in prostate cancer. Clin Cancer Res. Feb. 1, 2009;15(3):1032-8. doi: 10.1158/1078-0432.CCR-08-1910.

Sebat, et al. Large-Scale Copy Number Polymorphism in the Human Genome. Science, 305: 525-528 (2004).

Shaw et al. Genomic analysis of circulating cell-free DNA infers breast cancer dormancy. Genome Research 22 (2):220-231 (Feb. 2012).

Shaw, et al. Microsatellite alterations plasma DNA of primary breast cancer patients. Clin Cancer Res. Mar. 2000;6 (3):1119-24.

Shinozaki, et al. Utility of circulating B-Raf Dna mutation in serum for monitoring melanoma patients receiving biochemotherapy. Clin Cancer Res. Apr. 1, 2007;13(7):2068-74.

Shiroguchi, et al. Digital RNA sequencing minimizes sequence-dependent bias and amplification noise with optimized single-molecule barcodes. Proc Natl Acad Sci U S A. Jan. 24, 2012;109(4):1347-52. doi: 10.1073/pnas.1118018109. Epub Jan. 9, 2012.

Shoemaker, et al. Quantitative phenotypic analysis of yeast deletion mutants using a highly parallel molecular bar-coding strategy. Nature Genetics, 14: 450-456 (1996).

Simen, B.B. et al. "Validation of a Next-Generation-Sequencing Cancer Panel for Use in the Clinical Laboratory" Archives of Pathology & Laboratory Medicine (2015) 139(4):508-517.

Simpson, et al. Copy number variant detection in inbred strains from short read sequence data. Bioinformatics. Feb. 15, 2010;26(4):565-7. doi: 10.1093/bioinformatics/btp693. Epub Dec. 18, 2009.

Smith, et al. Highly-multiplexed barcode sequencing: an efficient method for parallel analysis of pooled samples. Nucleic Acids Research, 38(13): e142 (2010).

Sorenson, et al. Soluble normal and mutated DNA sequences from single-copy genes in human blood. Cancer Epidemiol Biomarkers Prev. Jan.-Feb. 1994;3(1):67-71.

Sparks, et al. Selective analysis of cell-free DNA in maternal blood for evaluation of fetal trisomy. Prenat Diagn. Jan. 2012;32(1):3-9. doi: 10.1002/pd.2922. Epub Jan. 6, 2012.

Steinman. Free DNA in serum and plasma from normal adults. J Clin Invest. Aug. 1975;56(2):512-5.

Stitziel, et al. Computational and statistical approaches to analyzing variants identified byexome sequencing. Genome Biol. Sep. 14, 2011;12(9):227. doi: 10.1186/GB-2011-12-9-227.

Stroun, M, et al., "About the possible orgin and mechanism of circulating DNA apoptosis and active DNA release", Clin Chim Acta, vol. 313, No. 1-2, pp. 139-142, (2001).

Taback, et al. Detection of tumor-specific genetic alterations in bone marrow from early-stage breast cancer patients. Cancer Res. Apr. 15, 2003;63(8):1884-7.

Tan, et al. Genome-wide comparison of DNA hydroxymethylation in mouse embryonic stem cells and neural progenitor cells by a new comparative hMeDIP-seq method. Nucleic Acids Res. Apr. 2013;41(7):e84. doi: 10.1093/nar/gkt091. Epub Feb. 13, 2013.

Taudien, et al. Haplotyping and copy number estimation of the highly polymorphic human beta-defensin locus on 8p23 by 454 amplicon sequencing. BMC Genomics. Apr. 19, 2010;11:252. doi: 10.1186/1471-2164-11-252.

Teer, J.K. et al. "Systematic comparison of three genomic enrichment methods for massively parallel DNA sequencing" Genome Res (2010) 20(10):1420-1431.

Tomaz, et al. Differential methylation as a cause of allele dropout at the imprinted GNAS locus. Genet Test Mol Biomarkers. Aug. 2010;14(4):455-60. doi: 10.1089/gtmb.2010.0029.

Tomlinson, et al. A genome-wide association scan of tag SNPs identifies a susceptibility variant for colorectal cancer at 8q24.21. Nat Genet. Aug. 2007;39(8):984-8. Epub Jul. 8, 2007.

Tsai, et al. Discovery of rare mutations in populations: TILLING by sequencing. Plant Physiol. Jul. 2011;156 (3):1257-68. doi: 10.1104/pp.110.169748. Epub Apr. 29, 2011.

UCSC Genome Bioinformatics. About the UCSC Genome Bioinformatics Site. http://genome.ucsc.edu/index.html. Accessed on May 26, 2015. 2 pgs.

Umetani et al. Prediction of Breast Tumor Progression by Integrity of Free Circulating DNA in Serum. Journal of Clinical Oncology 24(26):4270-4276 (Sep. 10, 2006).

Utting, et al. Microsatellite analysis of free tumor DNA in urine, serum, and plasma of patients: a minimally invasive method for the detection of bladder cancer. Clin Cancer Res. Jan. 2002;8(1):35-40.

Van Houten, et al. Mutated p53 as a molecular marker for the diagnosis of head and neck cancer. J Pathol. Dec. 2002;198(4):476-86.

Van Orsouw, N. et al. "Complexity Reduction of Polymorphic Sequences (CRoPSTM): A Novel Approach for Large-Scale Polymorphism Discovery in Complex Genomes" PLoS One (2007) 11(e1172):1-10.

Velculescu, et al. Characterization of the Yeast Transcriptome. Cell, 88: 243-251 (1997).

(56) References Cited

OTHER PUBLICATIONS

Velculescu, et al. Serial Analysis of Gene Expression. Science, 270: 484-487 (1995).
Vogelstein, et al. Digital PCR. Proc. Natl. Acad. Sci., 96(16): 9236-9241(1999).
Walker, et al. Isothermal in vitro amplification of DNA by a restriction enzyme/DNA polymerase system. Proc Natl Acad Sci U S A. Jan. 1, 1992;89(1):392-6.
Walsh, et al. Detection of inherited mutations for breast and ovarian cancer using genomic capture and massively parallel sequencing. Proc Natl Acad Sci U S A. Jul. 13, 2010;107(28):12629-33. doi: 10.1073/pnas.1007983107. Epub Jun. 28, 2010.
Wan, J.C.M. et al. "Liquid biopsies come of age: towards implementation of circulating tumour DNA" Nature Rev (2017) 17:223-238.
Wang, et al. iCLIP predicts the dual splicing effects of TIA-RNA interactions, Oct. 2010, PLoS Biol, 8(10):e1000530.
Wang, et al. Molecular detection of APC, K-ras, and p53 mutations in the serum of colorectal cancer patients as circulating biomarkers. World J Surg. Jul. 2004;28(7):721-6. Epub Jun. 8, 2004.
Final Office Action for U.S. Appl. No. 19/192,901 dated Oct. 31, 2025.
Poon, A.F.Y. et al. "Phylogenetic Analysis of Population-Based an Deep Sequencing Data to Identify Coevolving Sites in the nef Gene of HIV-1" Moll Biol and Evolution (2010) 27(4):819-832.
Wang, et al. RNA-Seq: a revolutionary tool for transcriptomics. Nature Reviews Genetics, 10: 57-63 (2009).
Weber, et al. A real-time polymerase chain reaction assay for quantification of allele ratios and correction of amplification bias. Anal Biochem. Sep. 15, 2003;320(2):252-8.
Wittes, et al. Searching for Evidence of Altered Gene Expression: a Comment on Statistical Analysis of Microarray Data. Journal of the National Cancer Institute, 91(5): 400-401 (1999).
Wodicka, et al. Genome-wide expression monitoring in *Saccharomyces cerevisiae*. Nature Biotechnology, 15: 1359-1367 (1997).
Wojdacs, et al. Primer design versus PCR bias in methylation independent PCR amplifications. Epigenetics. May 16, 2009;4(4):231-4. Epub May 14, 2009.
Wood, et al. The genomic landscapes of human breast and colorectal cancers. Science. Nov. 16, 2007;318 (5853):1108-13. Epub Oct. 11, 2007.
Wood, et al. Using next-generation sequencing for high resolution multiplex analysis of copy number variation from nanogram quantities of DNA from formalin-fixed paraffin-embedded specimens. Nucleic Acids Res. Aug. 2010;38(14): e151. doi: 10.1093/nar/gkq510. Epub Jun. 4, 2010.
Xi, et al. Copy number variation detection in whole-genome sequencing data using the Bayesian information criterion. Proc Natl Acad Sci U S A. Nov. 15, 2011;108(46):E1128-36. doi: 10.1073/pnas.1110574108. Epub Nov. 7, 2011.
Yandell, et al. A probabilistic disease-gene finder for personal genomes. Genome Res. Sep. 2011;21(9):1529-42. doi: 10.1101/gr.123158.111. Epub Jun. 23, 2011.
Yang, et al., EGFR gene copy number as a predictive biomarker for the treatment of metastatic colorectal cancer with anti-EGFR monoclonal antibodies: a meta-analysis.,J Hematol Oncol, Aug. 16, 2012,5:52,1-9.
Yang. Simple binary segmentation frameworks for identifying variation in DNA copy number. BMC Bioinformatics. Oct. 30, 2012;13:277. doi: 10.1186/1471-2105-13-277.
Ye, et al. Fluorescent microsphere-based readout technology for multiplexed human single nucleotide polymorphism analysis and bacterial identification. Human Mutation, 17(4): 305-316 (2001).
Yoon, et al. Sensitive and accurate detection of copy number variants using read depth of coverage. Genome Res. Sep. 2009;19(9):1586-92. doi: 10.1101/gr.092981.109. Epub Aug. 5, 2009.
Zhang et al. "Comprehensive One-Step Molecular Analysis of Mitochondrial Genome by Massively Parallel Sequencing" Clinical Chem (2012) 58(9):1322-1331.
Zhang, et al. The impact of next-generation sequencing on genomics. J Genet Genomics. Mar. 20, 2011;38(3):95-109. doi: 10.1016/j.jgg.2011.02.003. Epub Mar. 15, 2011.
Zhao, et al. Homozygous Deletions and Chromosome Amplifications in Human Lung Carcinomas Revealed by Single Nucleotide Polymorphism Array Analysis. Cancer Research, 65: 5561-5570 (2005).
Zhou, et al. Counting alleles reveals a connection between chromosome 18q loss and vascularinvasion. Nature Biotechnology, 19: 78-81 (2001).
"LB-246/12—Detection of circulating tumor DNA in early stage cancers," Available at https://www.genomeweb.com/cancer/ngs-error-correction-method-described-aacr-excitement-grows-early-cancer-detection, Accessed on Apr. 26, 2017.
Alkan, et al. Personalized copy number and segmental duplication maps using next-generation sequencing. Nat Genet. Oct. 2009;41(10):1061-7. doi: 10.1038/ng.437. Epub Aug. 30, 2009.
Andersson, et al. Bayesian detection of periodic mRNA time profiles without use of training examples. BMC Bioinformatics. Feb. 9, 2006;7:63.
Angeloni, D. Molecular analysis of deletions in human chromosome 3p21 and the role of resident cancer genes in disease. Brief Funct Genomic Proteomic. Mar. 2007;6(1):19-39. Epub May 24, 2007.
Anglesio, M.S. et al. "Cancer-Associated Mutations in Endometriosis without Cancer" NEJM (2017) 376:1835-1848.
Ansorge "Next-generation DNA sequencing techniques." New Biotechnology, 25(4):195-203 (2009).
Appel, Maryke. Part II: It's all about conversion. Kapa Biosystems. Accessed Mar. 29, 2017. Printed Apr. 11, 2017. 5 pages. URL:https://www.kapabiosystems.com/ngs/part-ii-conversion/.
Ashford, Monica. NGS Error Correction Method Described at AACR as Excitement Grows for Early Cancer Detection. Genomeweb.com. Apr. 5, 2017. 3 pages. URL:https://www.genomeweb.com/cancer/ngs-error-correction-method-described-aacr-excitement-grows-early-cancer-detection.
Atanur, et al. The genome sequence of the spontaneously hypertensive rat: Analysis and functional significance. Genome Res. Jun. 2010;20(6):791-803. doi: 10.1101/gr.103499.109. Epub Apr. 29, 2010.
Audic, et al. "The Significance of Digital Gene Expression Profiles." Genome Research, 7: 986-995 (1997).
Barzon, et al. Evaluation of circulating thyroid-specific transcripts as markers of thyroid cancer relapse. Int J Cancer. Jul. 20, 2004;110(6):914-20.
Bendich, et al. Circulating DNA as a possible factor in oncogenesis. Science. Apr. 16, 1965;148(3668):374-6.
Blakely, C.M. et al. "Evolution and clinical impact of co-occurring genetic alterations in advanced-stage EGFR-mutant lung cancers" Nature Generated (2017) 49(12):1693-1704.
Bonaldo, et al. Normalization and subtraction: two approaches to facilitate gene discovery. Genome Res. Sep. 1996;6(9):791-806.
Bowcock, et al. Exclusion of the retinoblastoma gene and chromosome 13q as the site of a primary lesion for human breast cancer. Am J Hum Genet. Jan. 1990; 46(1):12-7.
Braha, et al. Simultaneous stochastic sensing of divalent metal ions. Nature Biotechnology, 18: 1005-1007 (2000).
Bremnes, et al. Circulating tumour-derived DNA and RNA markers in blood: a tool for early detection, diagnostics, and follow-up? Lung Cancer. Jul. 2005;49(1):1-12.
Brenner, et al. "Gene expression analysis by massively parallel signature sequencing (MPSS) on microbead arrays." Nature Biotechnology, 18: 630-634 (2000).
Brenner, et al. In vitro cloning of complex mixtures of DNA on microbeads: physical separation of differentially expressed cDNAs. Proc Natl Acad Sci U S A. Feb. 15, 2000;97(4):1665-70.
Campbell, et al. Identification of somatically acquired rearrangements in cancer using genome-wide massively parallel paired-end sequencing. Nat Genet. Jun. 2008;40(6):722-9. doi: 10.1038/ng.128. Epub Apr. 27, 2008.
Caramazza, et al. Chromosome 1 abnormalities in myeloid malignancies: a literature survey and karyotype-phenotype associations. Eur J Haematol. Mar. 2010;84(3):191-200. doi: 10.1111/j.1600-0609.2009.01392.x. Epub Nov. 30, 2009.

(56) References Cited

OTHER PUBLICATIONS

Carr, et al. Inferring relative proportions of DNA variants from sequencing electropherograms. Bioinformatics. Dec. 15, 2009;25(24):3244-50. doi: 10.1093/bioinformatics/btp583. Epub Oct. 9, 2009.
Casbon, et al. A method for counting PCR template molecules with application to next-generation sequencing. Nucleic Acids Res. Jul. 2011;39(12):e81. doi: 10.1093/nar/gkr217. Epub Apr. 13, 2011.
Castle, et al. DNA copy number, including telomeres and mitochondria, assayed using next-generation sequencing. BMC Genomics. Apr. 16, 2010;11:244. doi: 10.1186/1471-2164-11-244.
Chang, et al. Detection of allelic imbalance in ascitic supernatant by digital single nucleotide polymorphism analysis. Clin Cancer Res. Aug. 2002;8(8):2580-5.
Chee, et al. "Accessing genetic information with high-density DNA arrays." Science, 274: 610-614 (1996).
Chee. "Enzymatic multiplex DNA sequencing." Nucleic Acids Research, 19(12): 3301-3305 (1991).
Chen, et al. Microsatellite alterations in plasma DNA of small cell lung cancer patients. Nat Med. Sep. 1996;2 (9):1033-5.
Chin, et al. A SNP in a let-7 microRNA complementary site in the KRAS 3' untranslated region increases non-small cell lung cancer risk. Cancer Res. Oct. 15, 2008;68(20):8535-40. doi: 10.1158/0008-5472.CAN-08-2129.
Chiu, et al. Non-invasive prenatal assessment of trisomy 21 by multiplexed maternal plasma DNA sequencing: large scale validity study. BMJ. Jan. 11, 2011;342:c7401. doi: 10.1136/bmj.c7401.
Chiu, et al. Quantitative analysis of circulating mitochondrial DNA in plasma. Clin Chem. May 2003;49(5):719-26.
Church, et al. "Multiplex DNA sequencing." Science, 240: 185-188 (1988).
Clark, T.A. et al. "Analytical Validation of a Hybrid Capture Based Next-Generation Sequencing Clinical Assay for Genomic Profiling of Cell-Free Circulating Tumor DNA," J. Mol. Diagnostics (2018) 20(5):686-702.
Cook, et al. Methylated DNA labels for marking objects. Biotechnol Lett. Jan. 2003;25(1):89-94.
Costello, et al. Discovery and characterization of artifactual mutations in deep coverage targeted capture sequencing data due to oxidative DNA damage during sample preparation. Nucleic Acids Res. Apr. 1, 2013;41(6):e67. doi: 10.1093/nar/gks1443. Epub Jan. 8, 2013.
Coulet, et al. Detection of plasma tumor DNA in head and neck squamous cell carcinoma by microsatellite typing and p53 mutation analysis. Cancer Res. Feb. 1, 2000;60(3):707-11.
Cox, J. "Bar coding objects with DNA." Analyst. May 2001;126(5):545-7.
Craig, et al. Identification of genetic variants using bar-coded multiplexed sequencing. Nat Methods. Oct. 2008;5 (10):887-93. doi: 10.1038/nmeth.1251. Epub Sep. 14, 2008.
Daines, et al. High-throughput multiplex sequencing to discover copy number variants in *Drosophila*. Genetics. Aug. 2009;182(4):935-41. doi: 10.1534/genetics.109.103218. Epub Jun. 15, 2009.
D'Antoni, et al. Rapid quantitative analysis using a single molecule counting approach. Anal Biochem. May 1, 2006;352(1):97-109. Epub Feb. 10, 2006.
Daser, et al. "Interrogation of genomes by molecular copy-number counting (MCC)." Nature Methods, 3(6): 447-453 (2006).
De Saizieu, et al. "Bacterial transcript imaging by hybridization of total RNA to oligonucleotide arrays." Nature Biotechnology, 16: 45-48 (1998).
Diehl et al. Circulating mutant DNA to assess tumor dynamics. Nat Med 14(9):985-990 (2008).
Diehl, et al. Detection and quantification of mutations in the plasma of patients with colorectal tumors. Proc Natl Acad Sci US A. Nov. 8, 2005;102(45):16368-73. Epub Oct. 28, 2005.
Ding, L. et al. "Clonal evolution in relapsed acute myeloid leukemia revealed by whole-genome sequencing" Nature (2012) 481(7382):506-510.
Ehrich, et al. Noninvasive detection of fetal trisomy 21 by sequencing of DNA in maternal blood: a study in a clinical setting. Am J Obstet Gynecol. Mar. 2011;204(3):205.e1-11. doi: 10.1016/j.ajog.2010.12.060. Epub Feb. 18, 2011.
Eisenmann, et al. 5q-myelodysplastic syndromes: chromosome 5q genes direct a tumor-suppression network sensing actin dynamics. Oncogene. Oct. 1, 2009;28(39):3429-41. doi: 10.1038/onc.2009.207. Epub Jul. 13, 2009.
Elshire, et al. A robust, simple genotyping-by-sequencing (GBS) approach for high diversity species. PLoS One. May 4, 2011;6(5):e19379. doi: 10.1371/journal.pone.0019379.
Extended European search report and opinion dated Dec. 4, 2018 for EP Application No. 16789867.5.
Fan, et al. "Microfluidic digital PCR enables rapid prenatal diagnosis of fetal aneuploidy." Am Obstet Gynecol. 2009; 200:543.e1-543.e7.
Koboldt, et al. Massively parallel sequencing approaches for characterization of structural variation. Aug. 12, 2011. Methods Mol Biol. 2012;838:369-84. doi: 10.1007/978-1-61779-507-7_18.
Kolble, et al. Microsatellite alterations in serum DNA of patients with colorectal cancer. Lab Invest. Sep. 1999;79 (9):1145-50.
Konig, et al. iCLIP reveals the function of hnRNAP particles in splicing at individual nucleotide resolution, Jul. 2010, Nature Structural & Molecular Biology, 17(7):909-916.
Kopreski, et al. Detection of mutant K-ras DNA in plasma or serum of patients with colorectal cancer. Br J Cancer. 1997;76(10):1293-9.
Koyanagi, et al. Association of circulating tumor cells with serum tumor-related methylated DNA in peripheral blood of melanoma patients. Cancer Res. Jun. 15, 2006;66(12):6111-7.
Kukita, Y. et al. "High-fidelity target sequencing of individual molecules identified using barcode sequences: de novo detection and absolute quantitation of mutations in plasma cell-free DNA from cancer patients" DNA Research (2015) 22(4):269-277.
Lam, et al. Plasma DNA as a prognostic marker for stroke patients with negative neuroimaging within the first 24 h of symptom onset. Resuscitation. Jan. 2006;68(1):71-8. Epub Dec. 1, 2005.
Lanman, et al., Analytical and Clinical Validation of a Digital Sequencing Panel for Quantitative, Highly Accurate Evaluation of Cell-Free Circulating Tumor DNA PLoS One, Oct. 2015, 10(10), e0140712. doi: 10.1371/journal.pone.0140712.
Larson, et al. A single molecule view of of gene expression. Trends Cell Biol. Nov. 2009;19(11):630-7. Epub Oct. 8, 2009.
Leary, et al. Detection of chromosomal alterations in the circulation of cancer patients with whole-genome sequencing. Sci Transl Med. Nov. 28, 2012;4(162):162ra154. doi: 10.1126/scitranslmed.3004742.
Leary, et al. Development of personalized tumor biomarkers using massively parallel sequencing. Sci Transl Med. Feb. 24, 2010;2(20):20ra14. doi: 10.1126/scitranslmed.3000702.
Lecomte, et al. Detection of free-circulating tumor-associated DNA in plasma of colorectal cancer patients and its association with prognosis. Int J Cancer. Aug. 10, 2002;100(5):542-8.
Leon, et al. Free DNA in the serum of cancer patients and the effect of therapy. Cancer Res. Mar. 1977;37(3):646-50.
Leung, et al. Plasma Epstein-Barr viral deoxyribonucleic acid quantitation complements tumor-node-metastasis staging prognostication in nasopharyngeal carcinoma. J Clin Oncol. Dec. 1, 2006;24(34):5414-8.
Li, et al. Mapping short DNA sequencing reads and calling variants using mapping quality scores. Genome Res. Nov. 2008;18(11):1851-8. doi: 10.1101/gr.078212.108. Epub Aug. 19, 2008.
Li, et al. Structure-independent and quantitative ligation of single-stranged DNA. Anal Biochem. Feb. 15, 2006;349 (2):242-6. Epub Nov. 18, 2005.
Lizardi, et al. Mutation detection and single-molecule counting using isothermal rolling-circle amplification. Nat Genet. Jul. 1998;19(3):225-32.
Lo, et al. Quantitative Analysis of Cell-free Epstein-Barr Virus DNA in Plasma of Patients with Nasopharyngeal Carcinoma, Cancer Research, 59(6):1188-1191 (Mar. 1999).
Lockhart, et al. Expression monitoring by hybridization to high-density oligonucleotide arrays. Nature Biotechnology, 14: 1675-1680 (1996).

(56) References Cited

OTHER PUBLICATIONS

Lodes, et al. Novel Chimera-Free, High Efficiency Library Preparation for NGS Platforms. Poster. Presented at the Plant & Animal Genome XX Conference. San Diego, California. Jan. 14-18, 2012. 1 page.
Lucito, et al. Detecting gene copy number fluctuations in tumor cells by microarray analysis of genomic representations. Genome Res. Nov. 2000;10(11):1726-36.
Lucito, et al. Representational Oligonucleotide Microarray Analysis: A High-Resolution Method to Detect Genome Copy Number Variation. Genome Research (2003), 13: 2291-2305.
Maamar, et al. Noise in Gene Expression Determines Cell Fate in Bacillus subtilis. Science, 317: 526-529 (2007).
Mahmud, et al. Fast MCMC sampling for hidden Markov Models to determine copy number variations. BMC Bioinformatics. Nov. 2, 2011;12:428. doi: 10.1186/1471-2105-12-428.
Makrigiorgos, et al., A PCR-Based amplification method retaining quantative difference between two complex genomes. Nature Biotech, vol. 20, No. 9, pp. 936-939 (Sep. 2002).
Mandel, et al. Les acides nucleiques du plasma sanguin chez l'homme. C R Seances Soc Biol Fil. Feb. 1948;142 (3-4):241-3.
Marsit, et al. Epigenetic profiling reveals etiologically distinct patterns of DNA methylation in head and neck squamous cell carcinoma. Carcinogenesis. Mar. 2009;30(3):416-22. doi: 10.1093/carcin/bgp006. Epub Jan. 6, 2009.
McCloskey, et al. Encoding PCR products with batch-stamps and barcodes. Biochem Genet. Dec. 2007;45 (11-12):761-7. Epub Oct. 23, 2007.
Medvedev, et al. Detecting copy number variation with mated short reads. Genome Res. Nov. 2010;20(11):1613-22. doi: 10.1101/gr.106344.110. Epub Aug. 30, 2010.
Mei, et al. Identification of recurrent regions of Copy-Number Variants across multiple individuals. BMC Bioinformatics. Mar. 22, 2010;11:147. doi: 10.1186/1471-2105-11-147.
Meldrum, et al. Next generation sequencing for cancer diagnostics: a practical perspective. Clin Biochem Rev. Nov. 2011;32(4):177-95.
Milbury, et al. "Enabling Clinical Cancer Genomics for Rare Mutations: COLD-PCR Magnifies Mutations Prior to Targeted Amplicon Re-Sequencing". Clin Chem. Mar. 2012;58(3):580-9. doi: 10.1373/clinchem.2011.176198. Epub Dec. 21, 2011.
Miner, et al. Molecular barcodes detect redundancy and contamination in hairpin-bisulfite PCR. Nucleic Acids Res. Sep. 30, 2004;32(17):e135.
Mitchell, et al. Circulating microRNAS as stable blood-based markers for cancer detection. Proc Natl Acad Sci U S A. Jul. 29, 2008;105(30):10513-8. Epub Jul. 28, 2008.
Mitelman, F. et al. "The impact of translocations and gene fusions on cancer causation" Nature Rev. Cancer (2007) 7(4):233-245.
Mohan, et al., Changes in colorectal carcinoma genomes under anti-EGFR therapy identified by whole-genome plasma DNA sequencing., PLoS Genet, doi: 10.1371/journal.pgen.1004271. eCollection 2014.,Mar. 27, 2014,10(3), e1004271.
Mori, et al. Predictive utility of circulating methylated DNA in serum of melanoma patients receiving biochemotherapy. J Clin Oncol. Dec. 20, 2005;23(36):9351-8.
Morrissy, A.S. et al. "Next-generation tag sequencing for cancer gene expression profiling" Genome Research (2009) 19(10): 1825-1835.
Mortazavi, et al. Mapping and quantifying mammalian transcriptomes by RNA-Seq. Nat. Methods. 2008; 5, 621-628.
Narayan, et al. Ultrasensitive measurement of hotspot mutations in tumor DNA in blood using error-suppressed multiplexed deep sequencing. Cancer Res. Jul. 15, 2012;72(14):3492-8. doi: 10.1158/0008-5472.CAN-11-4037. Epub May 10, 2012.
Nawroz, et al. Microsatellite alterations in serum DNA of head and neck cancer patients. Nat Med. Sep. 1996;2 (9):1035-7.
Newman, et al. An ultrasensitive method for quantitating circulating tumor DNA with broad patient coverage. Nat Med. May 2014;20(5):548-54. doi: 10.1038/nm.3519. Epub Apr. 6, 2014.
Nord, et al. Accurate and exact CNV identification from targeted high-throughput sequence data. BMC Genomics. Apr. 12, 2011;12:184.
Office action dated Aug. 13, 2018 for U.S. Appl. No. 15/811,836 (Sausen et al.).
Office Action for Singapore Patent Application No. 11201708982W dated Dec. 31, 2018.
Office Action for Singapore Patent Application No. 11201708982W dated May 23, 2020.
Office Action for Singapore Patent Application No. 11201708982W dated Jan. 19, 2022.
Ogino, et al. Quantification of PCR bias caused by a single nucleotide polymorphism in SMN gene dosage analysis. J Mol Diagn. Nov. 2002;4(4):185-90.
Pacific Biosciences. Template Preparation and Sequencing Guide. Publication date: Oct. 14, 2014. Pacific Biosciences website http://www.pacificbiosciences.com/support/pubmap/documentation.html.
Pan, et al. Loss of heterozygosity patterns provide fingerprints for genetic heterogeneity in multistep cancer progression of tobacco smoke-induced non-small cell lung cancer. Cancer Res. Mar. 1, 2005;65(5):1664-9.
Fan, et al. "Parallel Genotyping of Human SNPs Using Generic High-density Oligonucleotide Tag Arrays." Genome Research, 10: 853-860 (2000).
Fan, et al. Noninvasive diagnosis of fetal aneuploidy by shotgun sequencing DNA from maternal blood. Proc Natl Acad Sci U S A. Oct. 21, 2008;105(42):16266-71. Epub Oct. 6, 2008.
Fan, et al. Non-invasive prenatal measurement of the fetal genome. Nature. Jul. 19, 2012;487(7407):320-4. doi: 10.1038/nature 11251.
Fonatsch, C. The role of chromosome 21 in hematology and oncology. Genes Chromosomes Cancer. Jun. 2010;49 (6):497-508. doi: 10.1002/gcc.20764.
Fong, S.L. et al. "Comparison of 7 Methods for Extracting Cell-Free DNA from Serum Samples of Colorectal Cancer Patients" Clinical Chem (2009) 55(3):587-598.
Forshew, T. et al. "Noninvasive Identification and Monitoring of Cancer Mutations by Targeted Deep Sequencing of Plasma DNA" Sci Transl Med (2012) 4(136) ra68.
Forster, et al. From next-generation sequencing alignments to accurate comparison and validation of single-nucleotide variants: the pibase software. Nucleic Acids Res. Jan. 7, 2013;41(1):e16. doi: 10.1093/nar/gks836. Epub Sep. 10, 2012.
Fournie, et al. Plasma DNA as a marker of cancerous cell death. Investigations in patients suffering from lung cancer and in nude mice bearing human tumours. Cancer Lett. May 8, 1995;91(2):221-7.
Freeman, et al. Profiling the T-cell receptor beta-chain repertoire by massively parallel sequencing. Genome Res. Oct. 2009;19(10):1817-24. doi: 10.1101/gr.092924.109. Epub Jun. 18, 2009.
Fu, et al. Counting individual DNA molecules by the stochastic attachment of diverse labels. Proc Natl Acad Sci U S A. May 31, 2011;108(22):9026-31. Epub May 11, 2011.
Fujiwara, et al. Identification of epigenetic aberrant promoter methylation in serum DNA is useful for early detection of lung cancer. Clin Cancer Res. Feb. 1, 2005;11(3):1219-25.
Fujiwara, et al. Plasma DNA microsatellites as tumor-specific markers and indicators of tumor progression in melanoma patients. Cancer Res. Apr. 1, 1999;59(7):1567-71.
Gerry, et al. Universal DNA microarray method for multiplex detection of low abundance point mutations. Journal of Molecular Biology, 292(2): 251-262 (1999).
Gillespie. Exact stochastic simulation of coupled chemical reactions. The Journal of Physical Chemistry, 81(25): 2340-2361 (1977).
Gordian, et al. Serum free circulating DNA is a useful biomarker to distinguish benign versus malignant prostate disease. Cancer Epidemiol Biomarkers Prev. Aug. 2010;19(8):1984-91. doi: 10.1158/1055-9965.EPI-10-0287. Epub Jul. 20, 2010.
Gormally, et al. Amount of DNA in plasma and cancer risk: a prospective study. Int J Cancer. Sep. 20, 2004;111 (5):746-9.
Grant, et al. SNP genotyping on a genome-wide amplified DOP-PCR template. Nucleic Acids Res. Nov. 15, 2002;30 (22):e25.
Gregory et al. "Targeted Single Molecule Mutation Detection with Massively Parallel Sequencing" Nucleic Acids Research (2015) 44(3):2-11.

(56) References Cited

OTHER PUBLICATIONS

Grutzmann, et al. Sensitive detection of colorectal cancer in peripheral blood by septin 9 DNA methylation assay. PLoS One. 2008;3(11):e3759. doi: 10.1371/journal.pone.0003759. Epub Nov. 19, 2008.
Gundry, et al. "Direct mutation analysis by high-throughput sequencing: from germline to low-abundant, somatic variants" Mutat Res Jan. 3, 2012; 729(1-2):1-15. doi: 10.1016/mrfmmm.2011.10.001. Pub Oct. 12, 2011.
Gundry, et al. Direct, genome-wide assessment of DNA mutations in single cells. Nucleic Acids Res. Mar. 2012;40 (5):2032-40. doi: 10.1093/nar/gkr949. Epub Nov. 15, 2011.
Hacia, et al. Determination of ancestral alleles for human single-nucleotide polymorphisms using high-density oligonucleotide arrays. Nature Genetics, 22: 164-167 (1999).
Hafner, et al., RNA-ligase-dependent biases in miRNA representation in deep-sequenced small RNA eDNA libraries, RNA Sep. 1, 2011, 17(9):1697-1712.
Hamady, et al. Error-correcting barcoded primers for pyrosequencing hundreds of samples in multiplex. Nat Methods. Mar. 2008;5(3):235-7. doi: 10.1038/nmeth.1184. Epub Feb. 10, 2008.
Hamm, C.A. et al. "Genomic and Immunological Tumor Profiling Identifies Targetable Pathways and Extensive CD8p/ PDL1b Immune Infiltration in Inflammatory Breast Cancer Tumors" Mol Canc Therapeutics (2016) 15(7):1746-1756.
Hensel, et al. Simultaneous identification of bacterial virulence genes by negative selection. Science. Jul. 21, 1995;269(5222):400-3.
Hiatt, et al. Parallel, tag-directed assembly of locally derived short sequence reads. Nat Methods. Feb. 2010;7 (2):119-22. doi: 10.1038/nmeth.1416. Epub Jan. 17, 2010.
Hiatt, et al. Single molecule molecular inversion probes for targeted, high-accuracy detection of low-frequency variation. Genome Res. May 2013;23(5):843-54. doi: 10.1101/gr.147686.112. Epub Feb. 4, 2013.
Hibi, et al. Molecular detection of genetic alterations in the serum of colorectal cancer patients. Cancer Res. Apr. 1, 1998;58(7):1405-7.
Holdenrieder, et al. Circulating nucleosomes and cytokeratin 19-fragments in patients with colorectal cancer during chemotherapy. Anticancer Res. May-Jun. 2005;25(3A):1795-801.
Holies, et al. A stochastic approach to count RNA molecules using DNA sequencing methods. 2003, Lecture Notes in Computer Science, vol. 2812, pp. 55-62.
Hollstein, M. et al. "p53 mutations in human cancers" Science (1991) 253(5015):49-53.
Hoque, et al. Detection of aberrant methylation of four genes in plasma DNA for the detection of breast cancer. J Clin Oncol. Sep. 10, 2006;24(26):4262-9. Epub Aug. 14, 2006.
Hosoda, W. et al. "Genetic analyses of isolated high-grade pancreatic intraepithelial neoplasia (HG-PanIN) reveal paucity of alterations in TP53 and SMAD4" J Path (2017) 242:16-23.
Howe, et al. Retinoblastoma growth suppressor and a 300-kDa protein appear to regulate cellular DNA synthesis. Proc Natl Acad Sci U S A. Aug. 1990;87(15):5883-7.
Hug, et al. Measurement of the number of molecules of a single mRNA species in a complex mRNA preparation. J Theor Biol. Apr. 21, 2003;221(4):615-24.
Hyland, et al. The normal and tumor spectrum of copy number variation: Copy number alterations correlate with changes in gene expression in tumor transcriptome. Nov. 15, 2009. 1 page. Retrieved from:http://tools.thermofisher.com/content/sfs/posters/cms_073633.pdf.
Iafrate, et al. Detection of large-scale variation in the human genome. Nat Genet. Sep. 2004;36(9):949-51. Epub Aug. 1, 2004.
Ikeguchi, et al. Detection of loss of heterozygosityat microsatellite loci in esophageal squamous-cell carcinoma. Oncology. 1999;56(2):164-8.
Ingolia, et al. Genome-wide analysis in vivo of translation with nucleotide resolution using ribosome profiling. Science. Apr. 10, 2009;324(5924):218-23. Epub Feb. 12, 2009.
Jabara, C. Capturing the cloud: High throughput sequencing of multiple individual genomes from a retroviral population. Biology Lunch Bunch Series, Training Initiatives in Biomedical & Biological Sciences of the University of North Carolina at Chapel Hill, Apr. 23, 2010.
Jabara, et al. Accurate sampling and deep sequencing of the HIV-1 protease gene using a Primer ID. (Paper # 665), The 18th Annual Conference on Retroviruses and Opportunistic Infections, Boston, Massachusetts, Mar. 2011.
Jabara, et al. Accurate sampling and deep sequencing of the HIV-1 protease gene using a Primer ID. Proc Natl Acad Sci U S A. Dec. 13, 2011;108(50):20166-71. doi: 10.1073/pnas.1110064108. Epub Nov. 30, 2011.
Jahr, et al. DNA fragments in the blood plasma of cancer patients: quantitations and evidence for their origin from apoptotic and necrotic cells. Cancer Res. Feb. 15, 2001;61(4):1659-65.
Jeronimo, et al. Quantitative GSTP1 hypermethylation in bodily fluids of patients with prostate cancer. Urology. Dec. 2002;60(6):1131-5.
Kanagawa. Bias and artifacts in multitemplate polymerase chain reactions (PCR), 2003, Journal of Bioscience and Bioengineering, vol. 96, No. 4, p. 317-323.
Kimura, et al. EGFR mutation status in tumour-derived DNA from pleural effusion fluid is a practical basis for predicting the response to gefitinib. Br J Cancer. Nov. 20, 2006;95(10):1390-5. Epub Oct. 24, 2006.
Kinde, et al. Detection and quantification of rare mutations with massively parallel sequencing. Proc Natl Acad Sci U S A. Jun. 7, 2011;108(23):9530-5. doi: 10.1073/pnas.1105422108. Epub May 17, 2011.
Kinde, et al. Supplemental Information, Detection and quantification of rare mutations with massively parallel sequencing. Proc Natl Acad Sci U S A. Jun. 7, 2011;108(23):1-10.
Kivioja, T., et al. Counting absolute numbers of molecules using unique molecular identifiers. Nat Methods. Nov. 20, 2011;9(1):72-4. doi: 10.1038/nmeth.1778.
Final Office Action for U.S. Appl. No. 15/796,642 dated Nov. 18, 2025.
Wall, J.D. et al. "Estimating genotype error rates from high-coverage next-generation sequence data" Genome Research (2014) 24:1734-1739.
Flynn, J.F. et al. "Anti-EGFR Therapy: Mechanism and Advances in Clinical Efficacy in Breast Cancer" J Oncology (2009) 526963, 16 pages, https://doi.org/10.1155/2009/526963.
Iqgql, N. et al. "A Breakthrough of Targeted Therapy in Cancer", Chemotherapy Research and Practice (2014) 357027, 9 pages. https://doi.org/10.1155/2014/357027.

* cited by examiner

I. <u>Genetic Information</u>
   A. Collecting Sources of Genetic Material and Sequencing the Materials (1)
   B. Processing Genetic Information (2)
      1. Genetic Variants
         a) Sequence Variants
         b) Copy Number Variants
      2. Frequency of Genetic Variants or Degree of CNV in Sample Containing Genetic Material
   C. Separating Information from noise (3)

II. <u>Diagnosis of Cancer</u>
   A. Based on Frequency of Sequence Variants or Level of CNV (4)
   B. Confidence of Detecting Genetic Variants in the Noise Range (5)

III. <u>Increasing Confidence of Diagnosis</u>
   A. Using a plurality of measurements to increase confidence of Diagnosis (6)
   B. Using measurements at a plurality of time points to determine whether cancer is advancing, in remission or stabilized (7)

*FIG. 1A*

POINT MUTATIONS - *Complete** *or Critical Exon Coverage in 70 Genes*

| | | | | | | | | | |
|---|---|---|---|---|---|---|---|---|---|
| *AKT1* | *ALK* | ***APC*** | ***AR*** | *ARAF* | ***ARID1A*** | *ATM* | ***BRAF*** | ***BRCA1*** | ***BRCA2*** |
| ***CCND1*** | ***CCND2*** | ***CCNE1*** | *CDH1* | ***CDK4*** | ***CDK6*** | ***CDKN2A*** | ***CDKN2B*** | *CTNNB1* | ***EGFR*** |
| ***ERBB2*** | *ESR1* | *EZH2* | *FBXW7* | ***FGFR1*** | ***FGFR2*** | *FGFR3* | *GATA3* | *GNA11* | *GNAQ* |
| *GNAS* | *HNF1A* | ***HRAS*** | *IDH1* | *IDH2* | *JAK2* | *JAK3* | ***KIT*** | ***KRAS*** | *MAP2K1* |
| *MAP2K2* | ***MET*** | *MLH1* | *MPL* | ***MYC*** | ***NF1*** | *NFE2L2* | *NOTCH1* | *NPM1* | ***NRAS*** |
| *NTRK1* | ***PDGFRA*** | ***PIK3CA*** | ***PTEN*** | *PTPN11* | ***RAF1*** | ***RB1*** | *RET* | *RHEB* | *RHOA* |
| *RIT1* | *ROS1* | *SMAD4* | *SMO* | *SRC* | *STK11* | *TERT* | ***TP53*** | *TSC1* | *VHL* |

AMPLIFICATIONS

| | | | | | | | | |
|---|---|---|---|---|---|---|---|---|
| *AR* | *BRAF* | *CCND1* | *CCND2* | *CCNE1* | *CDK4* | *CDK6* | *EGFR* | *ERBB2* |
| *FGFR1* | *FGFR2* | *KIT* | *KRAS* | *MET* | *MYC* | *PDGFRA* | *PIK3CA* | *RAF1* |

FUSIONS

| | | | | | |
|---|---|---|---|---|---|
| *ALK* | *FGFR2* | *FGFR3* | *RET* | *ROS1* | *NTRK1* |

INDELS

| | | |
|---|---|---|
| *EGFR* exons 19/20 | *ERBB2* exons 19/20 | *MET* exon 14 skipping |

FIG. 9

GENERATING ADJUSTED TEST RESULTS FROM MOLECULAR BARCODED CELL-FREE DNA SEQUENCE DATA

CROSS-REFERENCE TO RELATED APPLICATIONS

This application is a continuation application of U.S. patent application Ser. No. 15/796,642, filed Oct. 27, 2017, which is a continuation application of International Application No. PCT/US2016/030301, filed Apr. 29, 2016, which application claims the benefit under 35 U.S.C. § 119 (e) of U.S. Provisional Application No. 62/155,755, filed May 1, 2015, each of which is incorporated herein by reference in their entireties.

BACKGROUND

Cancer is a major cause of disease worldwide. Each year, tens of millions of people are diagnosed with cancer around the world, and more than half of the patients eventually die from it. In many countries, cancer ranks the second most common cause of death following cardiovascular diseases.

To detect cancer, several screening tests are available. A physical exam and history surveys general signs of health, including checking for signs of disease, such as lumps or other unusual physical symptoms. A history of the patient's health habits and past illnesses and treatments will also be taken. Laboratory tests are another type of screening test and may require medical procedures to procure samples of tissue, blood, urine, or other substances in the body before conducting laboratory testing. Imaging procedures screen for cancer by generating visual representations of areas inside the body. Genetic tests detect certain gene deleterious mutations linked to some types of cancer. Genetic testing is particularly useful for a number of diagnostic methods.

One approach for cancer screening may include the monitoring of a sample derived from cell free nucleic acids, a population of polynucleotides that can be found in different types of bodily fluids. In some cases, disease may be characterized or detected based on detection of genetic variations, such as a change in copy number variation and/or sequence variation of one or more nucleic acid sequences, or the development of other certain rare genetic alterations. Cell free DNA ("cfDNA") may contain genetic variations associated with a particular disease. With improvements in sequencing and techniques to manipulate nucleic acids, there is a need in the art for improved methods and systems for using cell free DNA to detect and monitor disease.

SUMMARY

In an aspect, the present disclosure provides a method for analyzing a disease state of a subject, comprising (a) using a genetic analyzer to generate genetic data from nucleic acid molecules in biological samples of the subject obtained at (i) two or more time points or (ii) substantially the same time point, wherein the genetic data relates to genetic information of the subject, and wherein the biological samples include a cell-free biological sample; (b) receiving the genetic data from the genetic analyzer; (c) with one or more programmed computer processors, using the genetic data to produce an adjusted test result in a characterization of the genetic information of the subject; and (d) outputting the adjusted test result into computer memory.

In some embodiments, the genetic data comprises current sequence reads and prior sequence reads, and wherein (c) comprises comparing the current sequence reads with the prior sequence reads and updating a diagnostic confidence indication accordingly with respect to the characterization of the genetic information of the subject, which diagnostic confidence indication is indicative of a probability of identifying one or more genetic variations in a biological sample of the subject.

In some embodiments, the method further comprises generating a confidence interval for the current sequence reads. In some embodiments, the method further comprises comparing the confidence interval with one or more prior confidence intervals and determining a disease progression based on overlapping confidence intervals.

In some embodiments, the biological samples are obtained at two or more time points including a first time point and a second time point, and wherein (c) comprises increasing a diagnostic confidence indication in a subsequent or a previous characterization if the information from the first time point corroborates information from the second time point. In some embodiments, the biological samples are obtained at two or more time points including a first time point and a second time point, and wherein (c) comprises increasing a diagnostic confidence indication in the subsequent characterization if the information from the first time point corroborates information from the second time point.

In some embodiments, a first co-variate variation is detected in the genetic data, and wherein (c) comprises increasing a diagnostic confidence indication in the subsequent characterization if a second co-variate variation is detected.

In some embodiments, the biological samples are obtained at two or more time points including a first time point and a second time point, and wherein (c) comprises decreasing a diagnostic confidence indication in the subsequent characterization if the information from a first time point conflicts with information from the second time point.

In some embodiments, the method further comprises obtaining a subsequent characterization and leaving as is a diagnostic confidence indication in the subsequent characterization for de novo information. In some embodiments, the method further comprises determining a frequency of one or more genetic variants detected in a collection of sequence reads included in the genetic data and producing the adjusted test result at least in part by comparing the frequency of the one or more genetic variants at the two or more time points. In some embodiments, the method further comprises determining an amount of copy number variation at one or more genetic loci detected in a collection of sequence reads included in the genetic data and producing the adjusted test result at least in part by comparing the amount at the two or more time points. In some embodiments, the method further comprises using the adjusted test result to provide (i) a therapeutic intervention or (ii) a diagnosis of a health or disease to the subject.

In some embodiments, the genetic data comprises sequence data from potions of a genome comprising disease-associated or cancer associated genetic variants.

In some embodiments, the method further comprises using the adjusted test result to increase a sensitivity of detecting genetic variants by increasing read depth of polynucleotides in a sample from the subject.

In some embodiments, the genetic data comprises a first set of genetic data and a second set of genetic data, wherein the first set of genetic data is at or below a detection threshold and the second set of genetic data is above the detection threshold. In some embodiments, the detection threshold is a noise threshold. In some embodiments, the method further comprises, in (c), adjusting a diagnosis of the subject from negative or uncertain to positive when the same genetic variants are detected in the first set of genetic data and the second set of genetic data in a plurality of sampling instances or time points. In some embodiments, the method further comprises, in (c), adjusting a diagnosis of the subject from negative or uncertain to positive in a characterization from an earlier time point when the same genetic variants are detected in the first set of genetic data at an earlier time point and in the second set of genetic data at a later time point.

In some embodiments, the disease state is cancer and the genetic analyzer is a nucleic acid sequencer.

In some embodiments, the biological samples include at least two different types of biological samples. In some embodiments, the biological samples include the same type of biological sample. In some embodiments, the biological samples are blood samples. In some embodiments, the nucleic acid molecules are cell-free deoxyribonucleic acid (DNA).

In another aspect, the present disclosure provides a method of detecting a trend in the amount of cancer polynucleotides in a biological sample from a subject over time, comprising determining, using or more programmed computer processors, a frequency of the cancer polynucleotides at each of a plurality of time points; determining an error range for the frequency at each of the plurality of time points to provide at least a first error range at a first time point and a second error range at a second time point subsequent to the first time point; and determining whether (1) the first error range overlaps with the second error range, which overlap is indicative of stability of frequency of the cancer polynucleotides at a plurality of time points, (2) the second error range is greater than the first error range, thereby indicating an increase in frequency of the cancer polynucleotides at a plurality of time points, or (3) the second error range is less than the first error range, thereby indicating a decrease in frequency of the cancer polynucleotides at a plurality of time points.

In some embodiments, the cancer polynucleotides are deoxyribonucleic acid (DNA) molecules. In some embodiments, the DNA is cell-free DNA.

In some embodiments, the frequency at each of the plurality of time points is determined by sequencing nucleic acid molecules in biological samples of the subject. In some embodiments, the biological samples are blood samples. In some embodiments, the nucleic acid molecules are cell-free deoxyribonucleic acid (DNA).

In another aspect, the present disclosure provides a method to detect one or more genetic variations and/or amount of genetic variation in a subject, comprising sequencing nucleic acid molecules in a cell-free nucleic acid sample of the subject with a genetic analyzer to generate a first set of sequence reads at a first time point; comparing the first set of sequence reads with at least a second set of sequence reads obtained at least at a second time point before the first time point to yield a comparison of first set of sequence reads and the at least the second set of sequence reads; using the comparison to update a diagnostic confidence indication accordingly, which diagnostic confidence indication is indicative of a probability of identifying one or more genetic variations in a cell-free nucleic acid sample of the subject; and detecting a presence or absence of the one or more genetic variations and/or amount of genetic variation in nucleic acid molecules in a cell-free nucleic acid sample of the subject based on the diagnostic confidence indication.

In some embodiments, the method further comprises obtaining the cell-free nucleic acid molecules from the subject.

In some embodiments, the method further comprises sequencing additional cell-free nucleic acid molecules of the subject to generate a third set of sequence reads at a third time point subsequent to the first time point, and detecting a presence or absence of the one or more genetic variations and/or amount of genetic variation in the additional cell-free nucleic acid molecules of the subject based on the diagnostic confidence indication.

In some embodiments, the method further comprises increasing the diagnostic confidence indication if information obtained from the first set of sequence reads at the first time point corroborates information obtained from the at least the second set of sequence reads at the second time point.

In some embodiments, the method further comprises decreasing the diagnostic confidence indication if information obtained from the first set of sequence reads at the first time point does not corroborate or conflicts with information obtained from the at least the second set of sequence reads at the second time point. In some embodiments, the method further comprises leaving as is the diagnostic confidence indication in a subsequent characterization for de novo information.

In another aspect, the present disclosure provides a method for detecting a mutation in a cell-free nucleic acid sample of a subject, comprising: (a) determining consensus sequences by comparing current sequence reads obtained from a genetic analyzer with prior sequence reads from a prior time period to yield a comparison, and updating a diagnostic confidence indication based on the comparison, wherein each consensus sequence corresponds to a unique polynucleotide among a set of tagged parent polynucleotides derived from the cell-free nucleic acid sample, and (b) based on the diagnostic confidence, generating a genetic profile of extracellular polynucleotides in the subject, wherein the genetic profile comprises data resulting from copy number variation or mutation analyses.

In some embodiments, the method further comprises prior to (a), providing a plurality of sets of tagged parent polynucleotides derived from the cell-free nucleic acid sample, wherein each set is mappable to a different reference sequence.

In some embodiments, the method further comprises: using the consensus sequences to normalize ratios or frequency of variance for each mappable base position and determining actual or potential rare variant(s) or mutation (s); and comparing a resulting number for each region with potential rare variant(s) or mutation(s) to similarly derived numbers from a reference sample.

In another aspect, the present disclosure provides a method to detect abnormal cellular activity, comprising: providing at least one set of tagged parent polynucleotides derived from a biological sample of a subject; amplifying the tagged parent polynucleotides in the set to produce a corresponding set of amplified progeny polynucleotides; using a genetic analyzer to sequence a subset of the set of amplified progeny polynucleotides to produce a set of sequencing reads; and collapsing the set of sequencing reads to generate a set of consensus sequences by comparing current sequence reads with prior sequence reads from at least one prior time period and updating a diagnostic confidence indication accordingly, which diagnostic confidence indication is indicative of a probability of identifying one or more genetic variations in a biological sample of the subject, wherein each consensus sequence corresponds to a unique polynucleotide among the set of tagged parent polynucleotides.

In some embodiments, the method further comprises increasing the diagnostic confidence indication if the set of sequencing reads is identified in the at least one prior time period. In some embodiments, the method further comprises decreasing the diagnostic confidence indication if the set of sequencing reads is not identified in the at least one prior time period. In some embodiments, the method further comprises keeping the diagnostic confidence indication unchanged if the set of sequencing reads is identified in the at least one prior time period but is nonconclusive.

In some embodiments, the set of sequencing reads comprises at least one sequencing read.

In some embodiments, the biological sample is a blood sample. In some embodiments, the biological sample comprises cell-free nucleic acid molecules, and at least one set of tagged parent polynucleotides are generated from the cell-free nucleic acid molecules.

In some embodiments, the method further comprises generating a genetic profile of polynucleotides of the subject, which genetic profile includes an analysis of one or more genetic variants of the subject. In some embodiments, the polynucleotides include extracellular polynucleotides.

In another aspect, the present disclosure provides a method for detecting a mutation in a cell-free or substantially cell free sample of a subject comprising: (a) sequencing extracellular polynucleotides from a bodily sample of the subject with a genetic analyzer; (b) for each of the extracellular polynucleotides, generating a plurality of sequencing reads; (c) filtering out reads that fail to meet a set threshold; (d) mapping sequence reads derived from the sequencing onto a reference sequence; (e) identifying a subset of mapped sequence reads that align with a variant of the reference sequence at each mappable base position; (f) for each mappable base position, calculating a ratio of (i) a number of mapped sequence reads that include a variant as compared to the reference sequence, to (ii) a number of total sequence reads for each mappable base position; and (g) using one or more programmed computer processors to compare the sequence reads with other sequence reads from at least one previous time point and updating a diagnostic confidence indication accordingly, which diagnostic confidence indication is indicative of a probability of identifying the variant.

In some embodiments, the bodily sample is a blood sample. In some embodiments, the extracellular polynucleotides include cell-free deoxyribonucleic acid (DNA) molecules.

In another aspect, the present disclosure provides a method for operating a genetic test equipment, comprising: providing initial starting genetic material obtained from a bodily sample obtained from a subject; converting double stranded polynucleotide molecules from the initial starting genetic material into at least one set of non-uniquely tagged parent polynucleotides, wherein each polynucleotide in a set is mappable to a reference sequence; and for each set of tagged parent polynucleotides: (i) amplifying the tagged parent polynucleotides in the set to produce a corresponding set of amplified progeny polynucleotides; (ii) sequencing the set of amplified progeny polynucleotides to produce a set of sequencing reads; (iii) collapsing the set of sequencing reads to generate a set of consensus sequences, wherein collapsing uses sequence information from a tag and at least one of: (1) sequence information at a beginning region of a sequence read, (2) an end region of the sequence read and (3) length of the sequence read, wherein each consensus sequence of the set of consensus sequences corresponds to a polynucleotide molecule among the set of tagged parent polynucleotides; and (iv) analyzing the set of consensus sequences for each set of tagged parent molecules; (v) comparing current sequence reads with prior sequence reads from at least one other time point; and (vi) updating a diagnostic confidence indication accordingly, which diagnostic confidence indication is indicative of a probability of identifying one or more genetic variations in a bodily sample of the subject.

In some embodiments, the bodily sample is a blood sample. In some embodiments, the initial starting genetic material includes cell-free deoxyribonucleic acid (DNA).

In some embodiments, the set of consensus sequences for each set of tagged parent molecules is analyzed separately.

In some embodiments, analyzing comprises detecting mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, abnormal changes in nucleic acid methylation infection or cancer.

In some embodiments, (vi) comprises increasing diagnostic confidence indication in the current sequence reads if information from the prior sequence reads corroborates information from the current sequence reads. In some embodiments, (vi) comprises decreasing a diagnostic confidence indication in the current sequence reads if information from the prior sequence reads conflicts with information from the current sequence reads. In some embodiments, (vi) comprises keeping a diagnostic confidence indication the same in the current sequence reads if information from the prior sequence reads is inconclusive with respect to information from the current sequence reads.

In some embodiments, (v) comprises comparing one or more current sequence read variations with one or more prior sequence read variations.

In another aspect, the present disclosure provides a method for detecting one or more genetic variants in a subject, comprising: (a) obtaining nucleic acid molecules from one or more cell-free biological samples of said subject; (b) assaying said nucleic acid molecules to produce a first set of genetic data and a second set of genetic data, wherein said first set of genetic data and/or said second set of genetic data is within a detection threshold; (c) comparing said first set of genetic data to said second set of genetic data to identify said one or more genetic variants in said first set of genetic data or said second set of genetic data; and (d) based on said one or more genetic variants identified in (c), using one or more programmed computer processors to update a diagnostic confidence indication for identifying said one or more genetic variants in a cell-free biological sample of said subject.

In some embodiments, said first set of genetic data and said second set of genetic data are within said detection threshold. In some embodiments, said first set of genetic data is within said detection threshold and said second set of genetic data is above said detection threshold. In some embodiments, said detection threshold is a noise threshold.

In some embodiments, the method further comprises identifying said one or more genetic variants in said first set of genetic data, and increasing said diagnostic confidence indication.

In some embodiments, subsets of said nucleic acid molecules are assayed at different time points. In some embodiments, said nucleic acid molecules are obtained from a plurality of cell-free biological samples at the same time point or different time points.

In some embodiments, said nucleic acid molecules are deoxyribose nucleic acid (DNA). In some embodiments, said DNA is cell-free DNA (cfDNA).

In some embodiments, the method further comprises generating a genetic profile for said subject, wherein said genetic profile comprises said diagnostic confidence indication for identifying said one or more genetic variants.

In some embodiments, a co-variate variant is identified in said first set of genetic data in (c), and further comprising updating said diagnostic confidence indication for identifying a second co-variate variant in a cell-free biological sample of said subject. In some embodiments, the method further comprises increasing said diagnostic confidence indication in (c) if said first set of genetic data is observed in said second set of genetic data. In some embodiments, the method further comprises decreasing said diagnostic confidence indication in (c) if said first set of genetic data differs from said second set of genetic data.

In some embodiments, said detection threshold comprises errors introduced by sequencing or amplification.

In some embodiments, said detection threshold comprises a per-base error rate of 0.5% to 5%. In some embodiments, said detection threshold comprises a per-base error rate of 0.5% to 1%.

In some embodiments, said nucleic acid molecules are obtained from a second cell-free biological sample of said subject. In some embodiments, said second cell-free biological sample is obtained after obtaining said cell-free biological sample of (a). In some embodiments, said second cell-free biological sample is obtained prior to obtaining said cell-free biological sample of (a). In some embodiments, said second cell-free biological sample is obtained concurrent with obtaining said cell-free biological sample of (a). In some embodiments, said first set of genetic data corresponds to said cell-free biological sample of (a) and said second set of genetic data corresponds to said second cell-free biological sample.

In some embodiments, the method further comprises: attaching tags to said nucleic acid molecules to generate tagged parent polynucleotides; amplifying said tagged parent polynucleotides to produce tagged progeny polynucleotides; and sequencing said tagged progeny polynucleotides to produce sequencing reads.

In some embodiments, the attaching comprises uniquely tagging the nucleic acid molecules. In some embodiments, the attaching comprises non-uniquely tagging said nucleic acid molecules such that no more than 5% of said nucleic acid molecules are uniquely tagged.

In some embodiments, the method further comprises selectively enriching sequences of interest prior to the sequencing.

In some embodiments, the method further comprises grouping said sequence reads into families based at least on a sequence tag. In some embodiments, grouping the sequence reads is further based on one or more of: sequence information at a beginning of a sequence read derived from the nucleic acid molecule, sequence information at an end of said sequence derived from the nucleic acid molecule, and a length of said sequence read.

In some embodiments, the method further comprises comparing the sequence reads grouped within each family to determine consensus sequences for each family, wherein each of the consensus sequences corresponds to a unique polynucleotide among the tagged parent polynucleotides.

In some embodiments, the method further comprises obtaining less than 100 ng of the nucleic acid molecules.

In another aspect, the present disclosure provides a method for calling a genetic variant in cell-free deoxyribose nucleic acids (cfDNA) from a subject comprising: (a) using a DNA sequencing system to sequence cfDNA from a sample taken at a first time point from a subject; (b) detecting a genetic variant in the sequenced cfDNA from the first time point, wherein the genetic variant is detected at a level below a diagnostic limit; (c) using the DNA sequencing system to sequence cfDNA from a sample taken from the subject at one or more subsequent time points; (d) detecting the genetic variant in the sequenced cfDNA from the one or more subsequent time points, wherein the genetic variant is detected at level below the diagnostic limit; (e) calling the samples as positive for the genetic variant based on detecting the genetic variant below the diagnostic limit in samples taken at a plurality of the time points.

In some embodiments, the method further comprises (f) detecting a trend, wherein, at the first time point, the genetic variant is detected below the diagnostic limit and called as positive, and, at one or more subsequent time points, the genetic variant is detected above the diagnostic limit whereby the genetic variant is increasing.

In some embodiments, the diagnostic limit is less than or equal to about 1.0%.

In another aspect, the present disclosure provides a method for calling a genetic variant in cell-free deoxyribose nucleic acids (cfDNA) from a subject comprising: (a) using a deoxyribonucleic acid (DNA) sequencing system to sequence cfDNA from a sample from a subject; (b) detecting a genetic variant in the sequenced cfDNA, wherein the genetic variant is detected at a level below a diagnostic limit; (c) using the DNA sequencing system to sequence cfDNA from the sample taken from the subject, wherein the sample is re-sequenced one or more times; (d) detecting the genetic variant in the sequenced cfDNA from the one or more re-sequenced samples, wherein the genetic variant is detected at level below the diagnostic limit; and (e) calling the samples as positive for the genetic variant based on detecting the genetic variant below the diagnostic limit in re-sequenced samples.

In another aspect, the present disclosure provides a non-transitory computer readable medium comprising machine-executable code that, upon execution by one or more computer processors, implements any of the methods above or elsewhere herein.

In another aspect, the present disclosure provides a computer system comprising one or more computer processors and memory coupled thereto. The memory comprises a non-transitory computer readable medium comprising machine-executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIGS. 1A-1D illustrate exemplary systems to reduce error rates and bias in DNA sequence readings.

FIG. 9 shows a gene panel that may be used with methods and systems of the present disclosure.

DETAILED DESCRIPTION

Figure 1B:
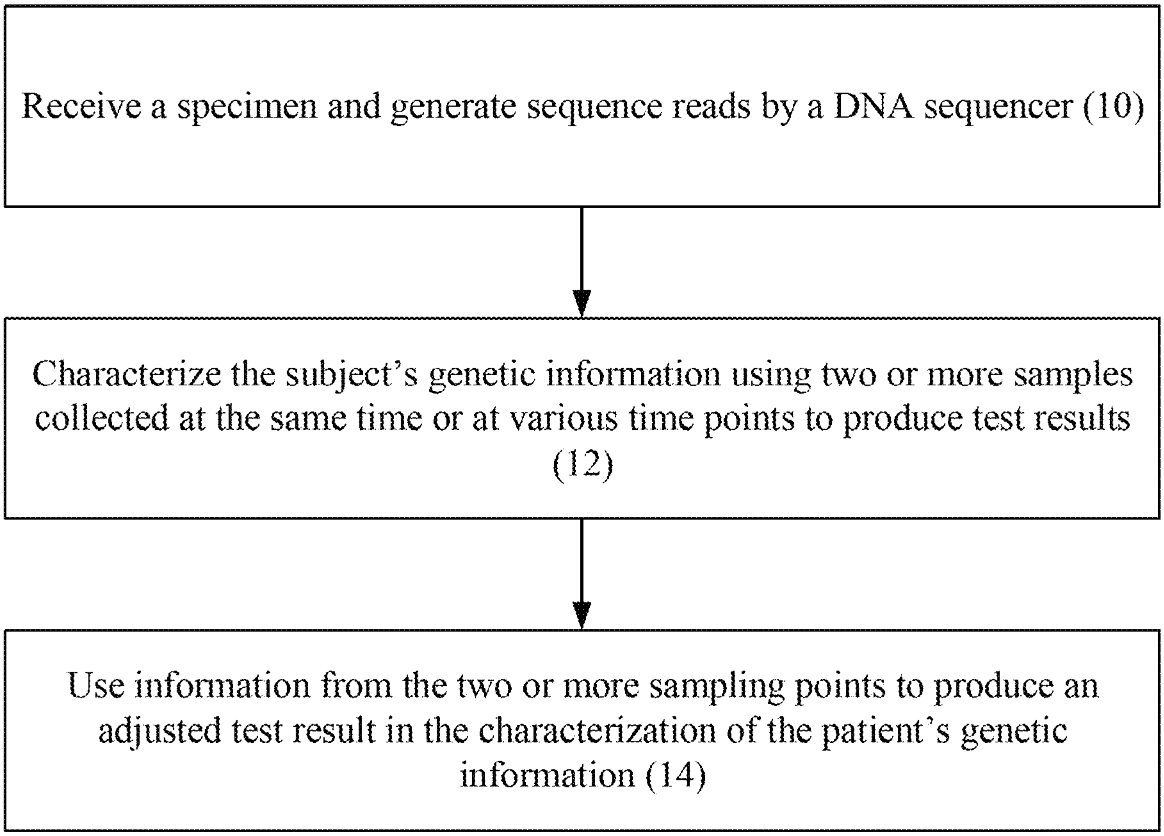

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, such as within 5-fold or within 2-fold, of a value. Where particular values are described in the application and claims, unless otherwise stated the term "about" meaning within an acceptable error range for the particular value should be assumed.

In certain embodiments, diagnostics involve detecting (e.g., measuring) a signal indicative of disease, such as a biomarker, and correlating the detection or measurement with a disease state. However, a signal may be weak due to low sample concentration or it may be obscured by noise. If the signal is weak such that it is at or below a noise threshold or detection limit, it may be difficult to differentiate signal from noise produced by the detection system or detect the signal at all. In such cases, one may not be confident in making a diagnosis. By looking at genetic data or detected variations from a plurality of points in time, a plurality of tests as confirmatory signals, or a plurality of commonly detected co-variate genetic variants, the diagnostic confidence can be enhanced.

The term detection limit and diagnostic limit, as used herein, generally refer to the capability to detect the presence or absence, or amount, of a given gene or variant at a predetermined level of confidence. A detection threshold as generally used herein refers to a range at or below the detection limit where certain genetic variants are undetectable or may not be differentiated from noise. In some instances, a "detection limit" may be lowest frequency or concentration at which a variant is detected in a variant-positive sample 95% of the time. A diagnostic limit may be the lowest frequency at which a positive call can be made. A diagnostic limit may be from about 0.01% to about 1%. A diagnostic limit may be less than or equal to about 5%, about 1.0%, about 0.8%, about 0.5%, about 0.25%, about 0.1%, about 0.08%, about 0.05%, about 0.03%, about 0.01%, or less. In some instances, the detection limit may be the same as the diagnostic limit. The detection limit or diagnostic limit may be a noise limit or noise threshold. In such a scenario, the detection limit or diagnostic limit is the limit at which signal may not be differentiated from noise.

In some instances, the diagnostic limit may be lower than the detection limit. Using methods and systems described herein, a genetic variant(s) present in an amount at or below the detection limit may be positively called at a predetermined level of confidence (e.g., at least 80%, 90%, or 95% confidence), even when the genetic variant(s) is present at or below a detection limit.

So, for example, sequence analysis of a sample may reveal a number of different genetic variants and a variety of frequencies or concentrations in the sample. The diagnostic limit may be set by a clinician at, for example, 1%, which is to say, no variant is to be reported as "present" in the sample, or "called" in a report unless the variant is present at a concentration of at least 1%. If a first variant is detected at 5%, that variant is "called" present in the sample and reported. Another variant is detected at 0.5%. This is below the diagnostic limit, and may be below the detection limit of the sequencing system. In this case, the clinician has several options. First, the same sample may be re-tested. If the variant is again detected, below or above the detection limit, it is now "called" as present in the sample. Second, the sequence data can be examined for the presence of a co-variate variation. For example, the variant may be a known resistance mutation. If a driver mutation is detected in the same gene from the sequence data, this also indicates that the resistance mutant is likely not to be a "noise" detection and, again, a positive call can be made. Third, the subject can be tested again at a later time point. If the variant is detected is the later sample, the first sample can be called as "present" for the variant. Alternatively, if a subsequent test show an amount of the variant with a confidence score that does not overlap with the first test, the variant can be called as increasing or decreasing in the subject, as the case may be.

Several factors may affect the ability to detect genes or variants at or near the detection or diagnostic limit. Detected genes or variants may be present at a low amounts or concentrations such that it a sequence analyzer cannot detect a gene or variant. For example, out of one million analyzed cell-free nucleic acid molecules, a genetic mutation may be present in one analyzed cell-free nucleic acid molecule, thus the variant base call exists at a frequency of one-in-million. A sequencing analyzer may mischaracterize the genetic mutation as a non-variant base call because the genetic mutation occurs with a low frequency relative to all other base calls at the same site. In such instances, a detection limit may generally refer to the ability of a genetic analyzer or sequencer to detect genetic variations present at very low frequencies. Additionally, sequence errors or artifacts introduced from sequencing or amplification can make it difficult or impossible to differentiate between errors and/or artifacts and detected genes or genetic variations. In such instances, a detection limit may refer to the ability to distinguish between variant base calls and error calls with confidence. The present disclosure provides technique(s) for detecting genetic variations at or below the detection limit and/or within a detection threshold.

The term "diagnostic confidence indication" as used herein generally refers to a representation, a number, a rank, a score, a degree or a value assigned to indicate the presence of one or more genetic variants and how much that presence is trusted. A diagnostic confidence indication may be indicative of a probability of identifying one or more genetic variations in a biological sample of the subject. For example, the representation can be a binary value or an alphanumeric ranking from A-Z, among others. In yet another example, the diagnostic confidence indication can have any value from 0 to 100, among others. In yet another example, the diagnostic confidence indication can be represented by a range or degree, e.g., "low" or "high", "more" or "less", "increased" or "decreased". A low diagnostic confidence indication indicate that a detected genetic variant may be noise (e.g., that the detected presence of the genetic variant cannot be trusted too much). A high diagnostic confidence indication means that, for a detected genetic variant, the genetic variant is likely to exist. In some instances, a result may be untrusted if its diagnostic confidence indication is under 25-30 out of 100.

The diagnostic confidence indication for each variant can be adjusted to indicate a confidence of predicting a genetic variation. The confidence can be increased or decreased by using measurements at a plurality of time points or from a plurality of samples at the same time point or at different time points. The diagnostic confidence can be further adjusted based on the detection of co-variate variations. The diagnostic confidence indication can be assigned by any of a number of statistical methods and can be based, at least in part, on the frequency at which the measurements are observed over a period of time.

The term "co-variate variations" or "co-variate variants", as used herein, generally refers to genetic variations that tend to vary together, for example, the presence of one variation is correlated with the presence of the co-variate variation. Accordingly, if a variant is seen below the diagnostic limit or the detection limit, and a co-variate variant is also detected, either above or below the detection limit, then it is more likely that the sample is positive for both variants, and they can be "called" as present in the sample. One example of co-variate variations are driver mutations and resistance mutations or mutations of unknown significance. That is, after a drive mutation is present, other mutations in the same gene, such as resistance mutations may appear, especially after treatment and recurrence of a cancer. As a non-limiting example, a driver mutation may be detected above the detection limit with high diagnostic confidence. However, due to insufficient sampling or noise, it may be difficult to confidently assess whether another genetic variation is present. If the genetic variation is typically present with the driver mutation such that the variants are co-variate variants (such as a passenger mutation or a resistance mutation), the diagnostic confidence indication of the genetic variant will increase. The strength of association between certain variants detected together can increase the probability, likelihood, and/or confidence that genetic data detected below a detection limit is a genetic variation.

The term "DNA sequencing system", as used herein, generally refers to DNA sample preparation protocols used in conjunction with a sequencing instrument. DNA sample preparation protocols may be directed to library preparation, amplification, adapter ligation, single strand elongation, among other molecular biological methods. A sequencing instrument may be any instrument capable of automating various sequencing methods or processes. Non-limiting examples of various sequencing methods or processes include: Sanger sequencing, high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS) (Helicos), massively-parallel sequencing, Clonal Single Molecule Array (Solexa), shotgun sequencing, Maxim-Gilbert sequencing, primer walking, and any other sequencing methods recognized in the art. A DNA sequencing system may comprise all protocols to prepare samples for sequencing in a particular sequencing instrument.

The term "subject," as used herein, generally refers to any organism that is used in the methods of the disclosure. In some examples, a subject is a human, mammal, vertebrate, invertebrate, eukaryote, archaea, fungus, or prokaryote. In some instances, a subject can be a human. A subject can be living or dead. A subject can be a patient. For example, a subject may be suffering from a disease (or suspected of suffering from a disease) and/or in the care of a medical practitioner. A subject can be an individual that is undergoing treatment and/or diagnosis for a health or medical condition. A subject and/or family member can be related to another subject used in the methods of the disclosure (e.g., a sister, a brother, a mother, a father, a nephew, a niece, an aunt, an uncle, a grandparent, a great-grandparent, a cousin).

The term "nucleic acid," as used herein, generally refers to a molecule comprising one or more nucleic acid subunits. A nucleic acid can include one or more subunits selected from adenosine (A), cytosine (C), guanine (G), thymine (T) and uracil (U), or variants thereof. A nucleotide can include A, C, G, T or U, or variants thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). A subunit can enable individual nucleic acid bases or groups of bases (e.g., AA, TA, AT, GC, CG, CT, TC, GT, TG, AC, CA, or uracil-counterparts thereof) to be resolved. In some examples, a nucleic acid is deoxyribonucleic acid (DNA) or ribonucleic acid (RNA), or derivatives thereof. A nucleic acid can be single-stranded or double stranded.

The term "genome" generally refers to an entirety of an organism's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together constitutes the human genome.

The term "sample," as used herein, generally refers to a biological sample. A sample may be or include blood, serum, plasma, vitreous, sputum, urine, tears, perspiration, saliva, semen, mucosal excretions, mucus, spinal fluid, amniotic fluid, lymph fluid and the like. A sample may be a cell-free sample. A sample may include nucleic acid molecules, such as polynucleotides. Polynucleotides may be deoxyribonucleic acid (DNA) or ribonucleic acid (RNA). Cell free polynucleotides may be fetal in origin (via fluid taken from a pregnant subject), or may be derived from tissue of the subject itself.

Detection Limit/Noise Range

Polynucleotide sequencing can be compared with a problem in communication theory. An initial individual polynucleotide or ensemble of polynucleotides can be conceptualized as an original message. Tagging and/or amplifying can be thought of as encoding the original message into a signal. Sequencing can be thought of as communication channel. The output of a sequencer, e.g., sequence reads, can be thought of as a received signal. Bioinformatic processing can be thought of as a receiver that decodes the received signal to produce a transmitted message, e.g., a nucleotide sequence or sequences. The received signal can include artifacts, such as noise and distortion. Noise can be thought of as an unwanted random addition to a signal. Distortion can be thought of as an alteration in the amplitude of a signal or portion of a signal.

Noise can be introduced through errors in copying and/or reading a polynucleotide. For example, in a sequencing process, a single polynucleotide can first be subject to amplification. Amplification can introduce errors, so that a subset of the amplified polynucleotides may contain, at a particular locus, a base that is not the same as the original base at that locus. Furthermore, in the reading process a base at any particular locus may be read incorrectly. As a consequence, the collection of sequence reads can include a certain percentage of base calls at a locus that are not the same as the original base. In typical sequencing technologies this error rate can be in the single digits, e.g., 2%-3%. In some instances, the error rate can be up to about 10%, up to about 9%, up to about 8%, up to about 7%, up to about 6%, up to about 5%, up to about 4%, up to about 3%, up to about 2%, or up to about 1%. When a collection of molecules that are all presumed to have the same sequence are sequenced, this noise may be sufficiently small that one can identify the original base with high reliability.

However, if a collection of parent polynucleotides includes a subset of polynucleotides having that vary at a particular locus, noise can be a significant problem. This can be the case, for example, when cell-free DNA includes not only germline DNA, but DNA from another source, such as fetal DNA or DNA from a cancer cell. In this case, if the frequency of molecules with sequence variants may be in the same range as the frequency of errors introduced by the sequencing process, then true sequence variants may not be distinguishable from noise. This could interfere, for example, with detecting sequence variants in a sample. For example, sequences can have a per-base error rate of 0.5-1%. Amplification bias and sequencing errors introduce noise into the final sequencing product. This noise can diminish sensitivity of detection. As a non-limiting example, sequence variants whose frequency is less than the sequencing error rate can be mistaken for noise.

A noise range or detection limit refers to instances where the frequency of molecules with sequence variants is in the same range as the frequency of errors introduced by the sequencing process. A "detection limit" may also refer to instances where too few variant-carrying molecules are sequenced for the variant to be detected. The frequency of molecules with sequence variants may be in the same range as the frequency of errors as a result of a small amount of nucleic acid molecules. As a non-limiting example, a sampled amount of nucleic acids, e.g. 100 ng, may contain a relatively small number of cell-free nucleic acid molecules, e.g. circulating tumor DNA molecules, such that the frequency of a sequence variant may be low, even though the variant may be present in a majority of circulating tumor DNA molecules. Alternately, the sequence variant may be rare or occur in only a very small amount of the sampled nucleic acids such that a detected variant is indistinguishable from noise and/or sequencing error. As a non-limiting example, at a particular locus, a genetic variant may only be detected in 0.1% to 5% of all reads at that locus.

Distortion can be manifested in the sequencing process as a difference in signal strength, e.g., total number of sequence reads, produced by molecules in a parent population at the same frequency. Distortion can be introduced, for example, through amplification bias, GC bias, or sequencing bias. This could interfere with detecting copy number variation in a sample. GC bias results in the uneven representation of areas rich or poor in GC content in the sequence reading. Also, by providing reads of sequences in greater or less amounts than their actual number in a population, amplification bias can distort measurements of copy number variation.

Sequencing and/or amplification artifacts or errors, such as noise and/or distortion, may be reduced in a polynucleotide sequencing process. Sequencing and/or amplification artifacts or errors may be reduced using a wide variety of techniques for sequencing and sequence analysis. Various techniques may include sequencing methodologies and/or statistical methods.

One way to reduce noise and/or distortion is to filter sequence reads. As a non-limiting example, sequence reads may be filtered by requiring sequence reads to meet a quality threshold, or by reducing GC bias. Such methods typically are performed on the collection of sequence reads that are the output of a sequencer, and can be performed sequence read-by-sequence read, without regard for family structure (sub-collections of sequences derived from a single original parent molecule).

Another way to reduce noise and/or distortion from a single individual molecule or from an ensemble of molecules is to group sequence reads into families derived from original individual molecules to reduce noise and/or distortion from a single individual molecule or from an ensemble of molecules. Efficient conversion of individual polynucleotides in a sample of initial genetic material into sequence-ready tagged parent polynucleotides may increase the probability that individual polynucleotides in a sample of initial genetic material will be represented in a sequence-ready sample. This can produce sequence information about more polynucleotides in the initial sample. Additionally, high yield generation of consensus sequences for tagged parent polynucleotides by high-rate sampling of progeny polynucleotides amplified from the tagged parent polynucleotides, and collapsing of generated sequence reads into consensus sequences representing sequences of parent tagged polynucleotides can reduce noise introduced by amplification bias and/or sequencing errors, and can increase sensitivity of detection. Collapsing sequence reads into a consensus sequence is one way to reduce noise in the received message from one molecule. Using probabilistic functions that convert received frequencies is another way to reduce noise and/or distortion. With respect to an ensemble of molecules, grouping reads into families and determining a quantitative measure of the families reduces distortion, for example, in the quantity of molecules at each of a plurality of different loci. Again, collapsing sequence reads of different families into consensus sequences eliminate errors introduced by amplification and/or sequencing error. Furthermore, determining frequencies of base calls based on probabilities derived from family information also reduces noise in the received message from an ensemble of molecules.

Noise and/or distortion may be further reduced by comparing genetic variations in a sequence read with genetic variations other sequence reads. A genetic variation observed in one sequence read and again in other sequence reads increases the probability that a detected variant is in fact a genetic variant and not merely a sequencing error or noise. As a non-limiting example, if a genetic variation is observed in a first sequence read and also observed in a second sequence read, a Bayesian inference may be made regarding whether the variation is in fact a genetic variation and not a sequencing error.

The present disclosure provides methods for detecting variations in nucleic acid molecules, particularly those at a frequency within a noise range or below a detection limit. Variants initially detected in nucleic acid molecules can be compared to other variants, such as for example variants at the same locus or co-variate genetic variants, to determine whether a variant is more or less likely to be accurately detected. Variants may be detected in amplified nucleic acid molecules, detected in sequence reads or collapsed sequence reads.

Repeated detection of a variant may increase the probability, likelihood, and/or confidence that a variant is accurately detected. A variant can be repeatedly detected by comparing two or more sets of genetic data or genetic variations. The two or more sets of genetic variations can be both samples at multiple time points and different samples at the same time point (for example a re-analyzed blood sample). In detecting a variant in the noise range or below the noise threshold, the re-sampling or repeated detection of a low frequency variant makes it more likely that the variant is in fact a variant and not a sequencing error. Re-sampling can be from the same sample, such as a sample that is re-analyzed or re-run, or from samples at different time points.

As a non-limiting example, a genetic variant having a low confidence score may be detected at a frequency or amount below the detection limit or noise range. However, if the genetic variant is observed again, such as for example at a later time point, in a prior sample, or upon re-analyzing a sample, the confidence score may increase. Thus, variant may be detected with greater confidence despite being present in a frequency or amount below the detection limit or noise range. In other instances, where the genetic variant is not observed again upon, for example, re-sampling, a confidence score may remain constant or decrease. Alternately, if a genetic variant observed at a particular locus conflicts a re-sampled result, the confidence score may decrease.

Co-variate detection may increase the probability, likelihood, and/or confidence that a variant is accurately detected. For co-variate genetic variants, the presence of one genetic variant is associated with the presence of one or more other genetic variants. Based on the detection of a co-variate genetic variation, it may be possible to infer the presence of an associated co-variate genetic variation, even where the associated genetic variation is present below a detection limit. Alternately, based on the detection of a co-variate genetic variation, the diagnostic confidence indication for the associated genetic variation may be increased. Further, in some instances where a co-variate variant is detected, a detection threshold for a co-variate variant detected below a detection limit may be decreased. Non-limiting examples of co-variate variations or genes include: driver mutations and resistance mutations, driver mutations and passenger mutations. As specific example of co-variants or genes is EGFR L858R activating mutation and EGFR T790M resistance mutation, found in lung cancers. Numerous other co-variate variants and genes are associated with various resistance mutations and will be recognized by one having skill in the art.

The present disclosure provides methods for detecting genetic variants where at least some variants are in the noise range or threshold. In the noise threshold or range, it may be difficult or impossible or difficult to detect genetic variations with confidence. In some instances, a noise threshold provides a limit for detecting genetic variation with statistical confidence. The noise threshold or range may overlap with a sequencing error rate. The noise threshold may be the same as the sequencing error rate. The noise threshold may be lower than the sequencing error rate. The noise threshold may be up to about 10%, up to about 9%, up to about 8%, up to about 7%, up to about 6%, up to about 5%, up to about 4%, up to about 3%, up to about 2%, or up to about 1%. In some instances, the noise range is about 0.5% to 10% errors per base. In some instances, the noise threshold is about 0.5% to 5% errors per base. In some instances, the noise threshold is about 0.5% to 1% errors per base. The terms noise and threshold may be used interchangeably.

Several types of genetic variants may be detected in nucleic acid molecules. Genetic variations may be interchangeably referred to as genetic variants or genetic aberrations. Genetic variations may include a single base substitution, a copy number variation, an indel and a gene fusion. A combination of these genetic variants may be detected. Non-limiting examples of additional genetic variants may also include: a transversion, a translocation, an inversion, a deletion, aneuploidy, partial aneuploidy, polyploidy, chromosomal instability, chromosomal structure alterations, chromosome fusions, a gene truncation, a gene amplification, a gene duplication, a chromosomal lesion, a DNA lesion, abnormal changes in nucleic acid chemical modifications, abnormal changes in epigenetic patterns and abnormal changes in nucleic acid methylation.

In one implementation, using measurements from a plurality of samples collected substantially at once or over a plurality of time points, the diagnostic confidence indication for each variant can be adjusted to indicate a confidence of predicting the observation of the copy number variation (CNV) or mutation. The confidence can be increased by using measurements at a plurality of time points to determine whether cancer is advancing, in remission or stabilized. The diagnostic confidence indication can be assigned by any of a number of statistical methods and can be based, at least in part, on the frequency at which the measurements are observed over a period of time. For example, a statistical correlation of current and prior results can be done. Alternatively, for each diagnosis, a hidden Markov model can be built, such that a maximum likelihood or maximum a posteriori decision can be made based on the frequency of occurrence of a particular test event from a plurality of measurements or a time points. As part of this model, the probability of error and resultant diagnostic confidence indication for a particular decision can be output as well. In this manner, the measurements of a parameter, whether or not they are in the noise range, may be provided with a confidence interval. Tested over time, one can increase the predictive confidence of whether a cancer is advancing, stabilized or in remission by comparing confidence intervals over time. Two sampling time points can be separated by at least about 1 microsecond, 1 millisecond, 1 second, 10 seconds, 30 seconds, 1 minute, 10 minutes, 30 minutes, 1 hour, 12 hours, 1 day, 1 week, 2 weeks, 3 weeks, one month, or one year. Two time points can be separated by about a month to about a year, about a year to about 5 years, or no more than about three months, two months, one month, three weeks, two weeks, one week, one day, or twelve hours.

FIG. 1A shows a first exemplary system to reduce error rates and bias that can be orders of magnitude higher than what is required to reliably detect de novo genomic alterations associated with cancer. The process first captures genetic information by collecting body fluid samples as sources of genetic material (blood, saliva, sweat, among others) and then the process sequences the materials (1). For example, polynucleotides in a sample can be sequenced, producing a plurality of sequence reads. The tumor burden in a sample that comprises polynucleotides can be estimated as a ratio of the relative number of sequence reads bearing a variant, to the total number of sequence reads generated from the sample. Also, in the case of copy number variants, the tumor burden can be estimated as the relative excess (in the case of gene duplication) or relative deficit (in the case of gene elimination) of total number of sequence reads at test and control loci. So, for example, a run may produce 1000 reads mapping to an oncogene locus, of which 900 correspond to wild type and 100 correspond to a cancer mutant, indicating a tumor burden of 10%. More details on exemplary collection and sequencing of the genetic materials are discussed below in FIGS. 2-4.

Next, genetic information is processed (2). Genetic variants are then identified. The variants can be a single-nucleotide polymorphism (SNP), in case it is a common genetic variant, a mutation, in a case where it is a rare genetic variant, or a copy-number variation, for example. The process then determines the frequency of genetic variants in the sample containing the genetic material. Since this process is noisy, the process separates information from noise (3).

The sequencing methods have error rates. For example, the mySeq system of Illumina can produce percent error rates in the low single digits. Thus, for 1000 sequence reads mapping to a locus, one might expect about 50 reads (about 5%) to include errors. Certain methodologies, such as those described in WO 2014/149134 (Talasaz and Eltoukhy), which is entirely incorporated herein by reference, can significantly reduce the error rate. Errors create noise that can obscure signals from cancer present at low levels in a sample. Thus, if a sample has a tumor burden at a level around the sequencing system error rate, e.g., around 0.1%-5%, it may be difficult to distinguish a signal corresponding to a genetic variant due to cancer from one due to noise.

Diagnosis of cancer can be done by analyzing the genetic variants, even in the presence of noise. The analysis can be based on the frequency of Sequence Variants or Level of CNV (4) and a diagnosis confidence indication or level for detecting genetic variants in the noise range can be established (5).

Next, the process increases the diagnosis confidence. This can be done using a plurality of measurements to increase confidence of Diagnosis (6), or alternatively using measurements at a plurality of time points to determine whether cancer is advancing, in remission or stabilized (7)

The diagnostic confidence can be used to identify disease states. For example, cell free polynucleotides taken from a subject can include polynucleotides derived from normal cells, as well as polynucleotides derived from diseased cells, such as cancer cells. Polynucleotides from cancer cells may bear genetic variants, such as somatic cell mutations and copy number variants. When cell free polynucleotides from a sample from a subject are sequenced, these cancer polynucleotides are detected as sequence variants or as copy number variants. The relative amount of tumor polynucleotides in a sample of cell free polynucleotides is referred to as the "tumor burden."

Measurements of a parameter, whether or not they are in the noise range, may be provided with a confidence interval. Tested over time, one can determine whether a cancer is advancing, stabilized or in remission by comparing confidence intervals over time. Where the confidence intervals do not overlap, this indicates the direction of disease.

FIG. 1B shows a second exemplary system to reduce error rates and bias that can be orders of magnitude higher than what is required to reliably detect de novo genomic alterations associated with cancer. This is done by generating a sequence read by a genetic analyzer, e.g., a DNA sequencer from a specimen (10). The system then characterizes the subject's genetic information over two or more samples or time points (12). Next, the system uses the information from the two or more sampling points or time points to produce an adjusted test result in characterizing the subject's genetic information (14).

The test result can be adjusted by enhancing or negating the confidence indication. For example, the process includes increasing a diagnostic confidence indication in a subsequent or a previous characterization if the information from a first time point corroborates information from the second time point. Alternatively, the process can increase a diagnostic confidence indication in the subsequent characterization if the information from a first time point corroborates information from the second time point. The diagnostic confidence indication in the subsequent characterization can be decreased if the information from a first time point conflicts with information from the second time point. Alternatively, the process can leave as is a diagnostic confidence indication in the subsequent characterization for de novo information.

In one embodiment of FIG. 1B, the system compares current sequence reads by a genetic analyzer, e.g., a DNA sequencer with prior sequence reads and updates a diagnostic confidence indication accordingly. Based on the enhanced confidence signal, the system accurately generates a genetic profile of extracellular polynucleotides in the subject, wherein the genetic profile comprises a plurality of data resulting from copy number variation and/or mutation analyses.

Figure 1C:
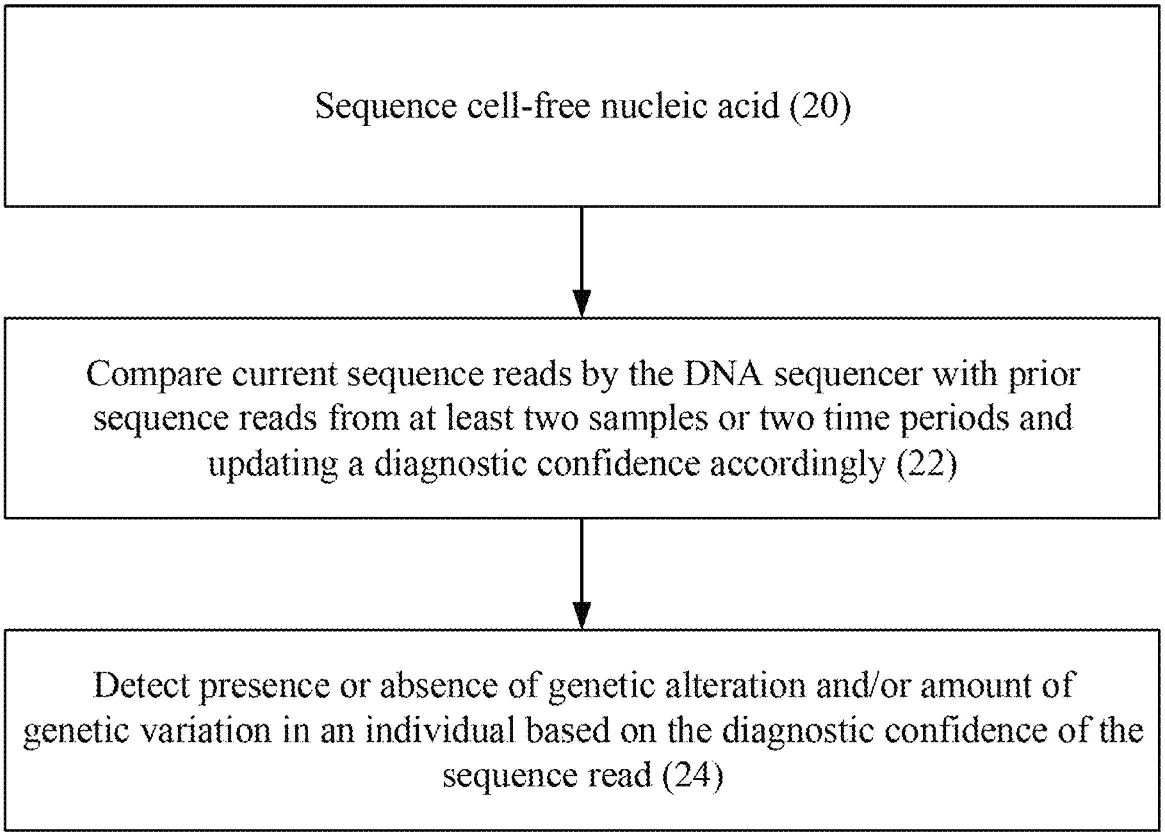

FIG. 1C shows a third exemplary system to reduce error rates and bias that can be orders of magnitude higher than what is required to reliably detect de novo genomic alterations associated with cancer. As a non-limiting example, the system performs cancer detection by sequencing of cell-free nucleic acid, wherein at least a portion of each gene in a panel of at least any of 10, 25, 50 or 100 genes is sequenced (20); comparing current sequence reads with prior sequence reads and updating a diagnostic confidence indication accordingly (22). The system then detects the presence or absence of genetic alteration and/or amount of genetic variation in an individual based on the diagnostic confidence indication of the current sequence read (24).

Figure 1D:
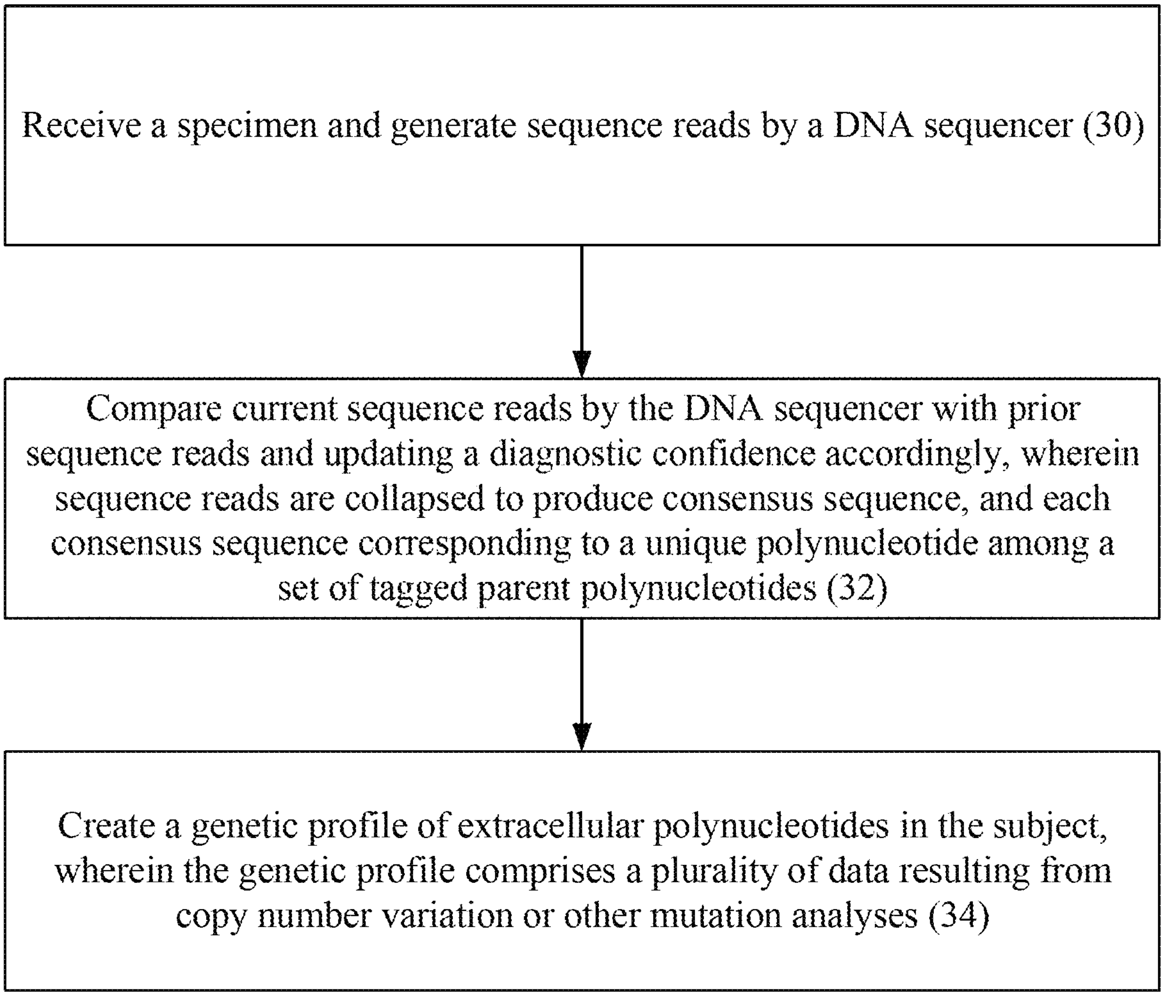

FIG. 1D shows yet another exemplary system to reduce error rates and bias that can be orders of magnitude higher than what is required to reliably detect de novo genomic alterations associated with cancer. The system performs cancer detection for example by sequencing of cell-free nucleic acid (30); comparing current sequence reads by the DNA sequencer with prior sequence reads and updating a diagnostic confidence accordingly, each consensus sequence corresponding to a unique polynucleotide among a set of tagged parent polynucleotides (32); and creating a genetic profile of extracellular polynucleotides in the subject, wherein the genetic profile comprises a plurality of data resulting from copy number variation or rare mutation analyses (34).

The systems of FIGS. 1A-1D detect with high sensitivity genetic variation in a sample of initial genetic material. The methods involve using one to three of the following tools: First, the efficient conversion of individual polynucleotides in a sample of initial genetic material into sequence-ready tagged parent polynucleotides, so as to increase the probability that individual polynucleotides in a sample of initial genetic material will be represented in a sequence-ready sample. This can produce sequence information about more polynucleotides in the initial sample. Second, high yield generation of consensus sequences for tagged parent polynucleotides by high rate sampling of progeny polynucleotides amplified from the tagged parent polynucleotides, and collapsing of generated sequence reads into consensus sequences representing sequences of parent tagged polynucleotides. This can reduce noise introduced by amplification bias and/or sequencing errors, and can increase sensitivity of detection. Third, the noise in the detection of mutations and copy number variations is reduced by comparing prior sample analysis with the current sample and increasing a diagnostic confidence indication if the same mutations and copy number variations have appeared in prior analysis and otherwise decreasing the diagnostic confidence indication if this is the first time the sequence is observed.

The system detects with high sensitivity genetic variation in a sample of initial genetic material. In one specific implementation, the system operation includes sample preparation, or the extraction and isolation of cell free polynucleotide sequences from a bodily fluid; subsequent sequencing of cell free polynucleotides by techniques utilized in the art; and application of bioinformatics tools to detect mutations and copy number variations as compared to a reference. The detection of mutations and copy number variations is enhanced by comparing prior sample analysis with the current sample and increasing a diagnostic confidence indication if the same mutations and copy number variations have appeared in prior analysis and otherwise decreasing or keep unchanged the diagnostic confidence indication if this is the first time the sequence is observed. The systems and methods also may contain a database or collection of different mutations or copy number variation profiles of different diseases, to be used as additional references in aiding detection of mutations, copy number variation profiling or general genetic profiling of a disease.

After sequencing data of cell free polynucleotide sequences is collected, one or more bioinformatics processes may be applied to the sequence data to detect genetic features or variations such as copy number variation, mutations or changes in epigenetic markers, including but not limited to methylation profiles. In some cases, in which copy number variation analysis is desired, sequence data may be: 1) aligned with a reference genome; 2) filtered and mapped; 3) partitioned into windows or bins of a sequence; 4) coverage reads counted for each window; 5) coverage reads can then be normalized using a stochastic or statistical modeling algorithm; and 6) an output file can be generated reflecting discrete copy number states at various positions in the genome. In other cases, in which mutation analysis is desired, sequence data may be 1) aligned with a reference genome; 2) filtered and mapped; 3) frequency of variant bases calculated based on coverage reads for that specific base; 4) variant base frequency normalized using a stochastic, statistical or probabilistic modeling algorithm; and 5) an output file can be generated reflecting mutation states at various positions in the genome. Temporal information from the current and prior analysis of the patient or subject is used to enhance the analysis and determination.

A variety of different reactions and/operations may occur within the systems and methods disclosed herein, including but not limited to: nucleic acid sequencing, nucleic acid quantification, sequencing optimization, detecting gene expression, quantifying gene expression, genomic profiling, cancer profiling, or analysis of expressed markers. Moreover, the systems and methods have numerous medical applications. For example, it may be used for the identification, detection, diagnosis, treatment, monitoring, staging of, or risk prediction of various genetic and non-genetic diseases and disorders including cancer. It may be used to assess subject response to different treatments of the genetic and non-genetic diseases, or provide information regarding disease progression and prognosis.

Polynucleotide Isolation and Extraction

The systems and methods of this disclosure may have a wide variety of uses in the manipulation, preparation, identification and/or quantification of nucleic acids including cell free polynucleotides. Examples of nucleic acids or polynucleotides include but are not limited to: DNA, RNA, amplicons, cDNA, dsDNA, ssDNA, plasmid DNA, cosmid DNA, high Molecular Weight (MW) DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA (e.g., retroviral RNA).

Cell free polynucleotides may be derived from a variety of sources including human, mammal, non-human mammal, ape, monkey, chimpanzee, reptilian, amphibian, or avian, sources. Further, samples may be extracted from variety of animal fluids containing cell free sequences, including but not limited to blood, serum, plasma, vitreous, sputum, urine, tears, perspiration, saliva, semen, mucosal excretions, mucus, spinal fluid, amniotic fluid, lymph fluid and the like.

Cell free polynucleotides may be fetal in origin (via fluid taken from a pregnant subject), or may be derived from tissue of the subject itself.

Isolation and extraction of cell free polynucleotides may be performed through collection of bodily fluids using a variety of techniques. In some cases, collection may comprise aspiration of a bodily fluid from a subject using a syringe. In other cases collection may comprise pipetting or direct collection of fluid into a collecting vessel.

After collection of bodily fluid, cell free polynucleotides may be isolated and extracted using a variety of techniques utilized in the art. In some cases, cell free DNA may be isolated, extracted and prepared using commercially available kits such as the Qiagen Qiamp® Circulating Nucleic Acid Kit protocol. In other examples, Qiagen Qubit™ dsDNA HS Assay kit protocol, Agilent™ DNA 1000 kit, or TruSeq™ Sequencing Library Preparation; Low-Throughput (LT) protocol may be used.

Generally, cell free polynucleotides are extracted and isolated by from bodily fluids through a partitioning step in which cell free DNAs, as found in solution, are separated from cells and other non-soluble components of the bodily fluid. Partitioning may include, but is not limited to, techniques such as centrifugation or filtration. In other cases, cells are not partitioned from cell free DNA first, but rather lysed. In this example, the genomic DNA of intact cells is partitioned through selective precipitation. Cell free polynucleotides, including DNA, may remain soluble and may be separated from insoluble genomic DNA and extracted. Generally, after addition of buffers and other wash steps specific to different kits, DNA may be precipitated using isopropanol precipitation. Further clean up steps may be used such as silica based columns to remove contaminants or salts. General steps may be optimized for specific applications. Non-specific bulk carrier polynucleotides, for example, may be added throughout the reaction to optimize certain aspects of the procedure such as yield.

Isolation and purification of cell free DNA may be accomplished using any methodology, including, but not limited to, the use of commercial kits and protocols provided by companies such as Sigma Aldrich, Life Technologies, Promega, Affymetrix, IBI or the like. Kits and protocols may also be non-commercially available.

After isolation, in some cases, the cell free polynucleotides are pre-mixed with one or more additional materials, such as one or more reagents (e.g., ligase, protease, polymerase) prior to sequencing.

One method of increasing conversion efficiency involves using a ligase engineered for optimal reactivity on single-stranded DNA, such as a ThermoPhage ssDNA ligase derivative. Such ligases bypass traditional steps in library preparation of end-repair and A-tailing that can have poor efficiencies and/or accumulated losses due to intermediate cleanup steps, and allows for twice the probability that either the sense or anti-sense starting polynucleotide will be converted into an appropriately tagged polynucleotide. It also converts double-stranded polynucleotides that may possess overhangs that may not be sufficiently blunt-ended by the typical end-repair reaction. Optimal reactions conditions for this ssDNA reaction are: 1× reaction buffer (50 mM MOPS (pH 7.5), 1 mM DTT, 5 mM MgCl2, 10 mM KCl). With 50 mM ATP, 25 mg/ml BSA, 2.5 mM MnCl2, 200 μmol 85 nt ssDNA oligomer and 5 U ssDNA ligase incubated at 65° C. for 1 hour. Subsequent amplification using PCR can further convert the tagged single-stranded library to a double-stranded library and yield an overall conversion efficiency of well above 20%. Other methods of increasing conversion rate, e.g., to above 10%, include, for example, any of the following, alone or in combination: Annealing-optimized molecular-inversion probes, blunt-end ligation with a well-controlled polynucleotide size range, sticky-end ligation or an upfront multiplex amplification step with or without the use of fusion primers.

Molecular Barcoding of Cell Free Polynucleotides

The systems and methods of this disclosure may also enable the cell free polynucleotides to be tagged or tracked in order to permit subsequent identification and origin of the particular polynucleotide. This feature is in contrast with other methods that use pooled or multiplex reactions and that only provide measurements or analyses as an average of multiple samples. Here, the assignment of an identifier to individual or subgroups of polynucleotides may allow for a unique identity to be assigned to individual sequences or fragments of sequences. This may allow acquisition of data from individual samples and is not limited to averages of samples.

In some examples, nucleic acids or other molecules derived from a single strand may share a common tag or identifier and therefore may be later identified as being derived from that strand. Similarly, all of the fragments from a single strand of nucleic acid may be tagged with the same identifier or tag, thereby permitting subsequent identification of fragments from the parent strand. In other cases, gene expression products (e.g., mRNA) may be tagged in order to quantify expression, by which the barcode, or the barcode in combination with sequence to which it is attached can be counted. In still other cases, the systems and methods can be used as a PCR amplification control. In such cases, multiple amplification products from a PCR reaction can be tagged with the same tag or identifier. If the products are later sequenced and demonstrate sequence differences, differences among products with the same identifier can then be attributed to PCR error.

Additionally, individual sequences may be identified based upon characteristics of sequence data for the read themselves. For example, the detection of unique sequence data at the beginning (start) and end (stop) portions of individual sequencing reads may be used, alone or in combination, with the length, or number of base pairs of each sequence read unique sequence to assign unique identities to individual molecules. Fragments from a single strand of nucleic acid, having been assigned a unique identity, may thereby permit subsequent identification of fragments from the parent strand. This can be used in conjunction with bottlenecking the initial starting genetic material to limit diversity.

Further, using unique sequence data at the beginning (start) and end (stop) portions of individual sequencing reads and sequencing read length may be used, alone or combination, with the use of barcodes. In some cases, the barcodes may be unique as described herein. In other cases, the barcodes themselves may not be unique. In this case, the use of non unique barcodes, in combination with sequence data at the beginning (start) and end (stop) portions of individual sequencing reads and sequencing read length may allow for the assignment of a unique identity to individual sequences. Similarly, fragments from a single strand of nucleic acid having been assigned a unique identity, may thereby permit subsequent identification of fragments from the parent strand.

Generally, the methods and systems provided herein are useful for preparation of cell free polynucleotide sequences to a down-stream application sequencing reaction. A sequencing method may be classic Sanger sequencing.

Sequencing methods may include, but are not limited to: high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS) (Helicos), massively-parallel sequencing, Clonal Single Molecule Array (Solexa), shotgun sequencing, Maxim-Gilbert sequencing, primer walking, and any other sequencing methods recognized in the art.

Assignment of Barcodes to Cell Free Polynucleotide Sequences

The systems and methods disclosed herein may be used in applications that involve the assignment of unique or non-unique identifiers, or molecular barcodes, to cell free polynucleotides. The identifier may be a bar-code oligonucleotide that is used to tag the polynucleotide; but, in some cases, different unique identifiers are used. For example, in some cases, the unique identifier is a hybridization probe. In other cases, the unique identifier is a dye, in which case the attachment may comprise intercalation of the dye into the analyte molecule (such as intercalation into DNA or RNA) or binding to a probe labeled with the dye. In still other cases, the unique identifier may be a nucleic acid oligonucleotide, in which case the attachment to the polynucleotide sequences may comprise a ligation reaction between the oligonucleotide and the sequences or incorporation through PCR. In other cases, the reaction may comprise addition of a metal isotope, either directly to the analyte or by a probe labeled with the isotope. Generally, assignment of unique or non-unique identifiers, or molecular barcodes in reactions of this disclosure may follow methods and systems described by, for example, U.S Patent Publication Nos. 2001/0053519, 2003/0152490, 2011/0160078, and U.S. Pat. No. 6,582,908, each of which is entirely incorporated herein by reference.

The method may comprise attaching oligonucleotide barcodes to nucleic acid analytes through an enzymatic reaction including but not limited to a ligation reaction. For example, the ligase enzyme may covalently attach a DNA barcode to fragmented DNA (e.g., high molecular-weight DNA). Following the attachment of the barcodes, the molecules may be subjected to a sequencing reaction.

However, other reactions may be used as well. For example, oligonucleotide primers containing barcode sequences may be used in amplification reactions (e.g., PCR, qPCR, reverse-transcriptase PCR, digital PCR, etc.) of the DNA template analytes, thereby producing tagged analytes. After assignment of barcodes to individual cell free polynucleotide sequences, the pool of molecules may be sequenced.

In some cases, PCR may be used for global amplification of cell free polynucleotide sequences. This may comprise using adapter sequences that may be first ligated to different molecules followed by PCR amplification using universal primers. PCR for sequencing may be performed using any methodology, including but not limited to use of commercial kits provided by Nugen (WGA kit), Life Technologies, Affymetrix, Promega, Qiagen and the like. In other cases, only certain target molecules within a population of cell free polynucleotide molecules may be amplified. Specific primers, may in conjunction with adapter ligation, may be used to selectively amplify certain targets for downstream sequencing.

The unique identifiers (e.g., oligonucleotide bar-codes, antibodies, probes, etc.) may be introduced to cell free polynucleotide sequences randomly or non-randomly. In some cases, they are introduced at an expected ratio of unique identifiers to microwells. For example, the unique identifiers may be loaded so that more than about 1, 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 unique identifiers are loaded per genome sample. In some cases, the unique identifiers may be loaded so that less than about 2, 3, 4, 5, 6, 7, 8, 9, 10, 20, 50, 100, 500, 1000, 5000, 10000, 50,000, 100,000, 500,000, 1,000, 000, 10,000,000, 50,000,000 or 1,000,000,000 unique identifiers are loaded per genome sample. In some cases, the average number of unique identifiers loaded per sample genome is less than, or greater than, about 1, 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 unique identifiers per genome sample.

In some cases, the unique identifiers may be a variety of lengths such that each barcode is at least about 1, 2, 3, 4, 5, 6, 7, 8, 9, 10, 20, 50, 100, 500, 1000 base pairs. In other cases, the barcodes may comprise less than 1, 2, 3, 4, 5, 6, 7, 8, 9, 10, 20, 50, 100, 500, 1000 base pairs.

In some cases, unique identifiers may be predetermined or random or semi-random sequence oligonucleotides. In other cases, a plurality of barcodes may be used such that barcodes are not necessarily unique to one another in the plurality. In this example, barcodes may be ligated to individual molecules such that the combination of the bar code and the sequence it may be ligated to creates a unique sequence that may be individually tracked. As described herein, detection of non unique barcodes in combination with sequence data of beginning (start) and end (stop) portions of sequence reads may allow assignment of a unique identity to a particular molecule. The length, or number of base pairs, of an individual sequence read may also be used to assign a unique identity to such a molecule. As described herein, fragments from a single strand of nucleic acid having been assigned a unique identity, may thereby permit subsequent identification of fragments from the parent strand. In this way the polynucleotides in the sample can be uniquely or substantially uniquely tagged.

The unique identifiers may be used to tag a wide range of analytes, including but not limited to RNA or DNA molecules. For example, unique identifiers (e.g., barcode oligonucleotides) may be attached to whole strands of nucleic acids or to fragments of nucleic acids (e.g., fragmented genomic DNA, fragmented RNA). The unique identifiers (e.g., oligonucleotides) may also bind to gene expression products, genomic DNA, mitochondrial DNA, RNA, mRNA, and the like.

In many applications, it may be important to determine whether individual cell free polynucleotide sequences each receive a different unique identifier (e.g., oligonucleotide barcode). If the population of unique identifiers introduced into the systems and methods is not significantly diverse, different analytes may possibly be tagged with identical identifiers. The systems and methods disclosed herein may enable detection of cell free polynucleotide sequences tagged with the same identifier. In some cases, a reference sequences may be included with the population of cell free polynucleotide sequences to be analyzed. The reference sequence may be, for example, a nucleic acid with a known sequence and a known quantity. If the unique identifiers are oligonucleotide barcodes and the analytes are nucleic acids, the tagged analytes may subsequently be sequenced and quantified. These methods may indicate if one or more fragments and/or analytes may have been assigned an identical barcode.

A method disclosed herein may comprise utilizing reagents necessary for the assignment of barcodes to the analytes. In the case of ligation reactions, reagents including, but not limited to, ligase enzyme, buffer, adapter oligonucleotides, a plurality of unique identifier DNA barcodes and the like may be loaded into the systems and methods. In the case of enrichment, reagents including but not limited to a plurality of PCR primers, oligonucleotides containing unique identifying sequence, or barcode sequence, DNA polymerase, DNTPs, and buffer and the like may be used in preparation for sequencing.

Generally, the method and system of this disclosure may utilize the methods of U.S. Pat. No. 7,537,897 in using molecular barcodes to count molecules or analytes, which is entirely incorporated herein by reference.

In a sample comprising fragmented genomic DNA, e.g., cell-free DNA (cfDNA), from a plurality of genomes, there is some likelihood that more than one polynucleotide from different genomes will have the same start and stop positions ("duplicates" or "cognates"). The probable number of duplicates beginning at any position is a function of the number of haploid genome equivalents in a sample and the distribution of fragment sizes. For example, cfDNA has a peak of fragments at about 160 nucleotides, and most of the fragments in this peak range from about 140 nucleotides to 180 nucleotides. Accordingly, cfDNA from a genome of about 3 billion bases (e.g., the human genome) may be comprised of almost 20 million ($2\times10^7$) polynucleotide fragments. A sample of about 30 ng DNA can contain about 10,000 haploid human genome equivalents. (Similarly, a sample of about 100 ng of DNA can contain about 30,000 haploid human genome equivalents.) A sample containing about 10,000 ($10^4$) haploid genome equivalents of such DNA can have about 200 billion ($2\times10^{11}$) individual polynucleotide molecules. It has been empirically determined that in a sample of about 10,000 haploid genome equivalents of human DNA, there are about 3 duplicate polynucleotides beginning at any given position. Thus, such a collection can contain a diversity of about $6\times10^{10}$-$8\times10^{10}$ (about 60 billion-80 billion e.g., about 70 billion ($7\times10^{10}$)) differently sequenced polynucleotide molecules.

The probability of correctly identifying molecules is dependent on initial number of genome equivalents, the length distribution of sequenced molecules, sequence uniformity and number of tags. When the tag count is equal to one, that is, equivalent to having no unique tags or not tagging. The table below lists the probability of correctly identifying a molecule as unique assuming a typical cell-free size distribution as above.

| Tag Count | Tag % Correctly uniquely identified |
|---|---|
| 1000 human haploid genome equivalents | |
| 1 | 96.9643 |
| 4 | 99.2290 |
| 9 | 99.6539 |
| 16 | 99.8064 |
| 25 | 99.8741 |
| 100 | 99.9685 |

-continued

| Tag Count | Tag % Correctly uniquely identified |
|---|---|
| 3000 human haploid genome equivalents | |
| 1 | 91.7233 |
| 4 | 97.8178 |
| 9 | 99.0198 |
| 16 | 99.4424 |
| 25 | 99.6412 |
| 100 | 99.9107 |

In this case, upon sequencing the genomic DNA, it may not be possible to determine which sequence reads are derived from which parent molecules. This problem can be diminished by tagging parent molecules with a sufficient number of unique identifiers (e.g., the tag count) such that there is a likelihood that two duplicate molecules, i.e., molecules having the same start and stop positions, bear different unique identifiers so that sequence reads are traceable back to particular parent molecules. One approach to this problem is to uniquely tag every, or nearly every, different parent molecule in the sample. However, depending on the number of haploid gene equivalents and distribution of fragment sizes in the sample, this may require billions of different unique identifiers.

The above method can be cumbersome and expensive. Individual polynucleotide fragments in a genomic nucleic acid sample (e.g., genomic DNA sample) can be uniquely identified by tagging with non-unique identifiers, e.g., non-uniquely tagging the individual polynucleotide fragments. As used herein, a collection of molecules can be considered to be "uniquely tagged" if each of at least 95% of the molecules in the collection bears an identifying tag ("identifier") that is not shared by any other molecule in the collection ("unique tag" or "unique identifier"). For unique tags, the number of tags may be fewer than the number of unique molecules in the sample. For unique tags, the number of tags may be fewer than 10% of number of molecules in sample. For unique tags, the number of tags may fewer than 1% of number of molecules in sample. A collection of molecules can be considered to be "non-uniquely tagged" if each of at least 1%, at least 5%, at least 10%, at least 15%, at least 20%, at least 25%, at least 30%, at least 35%, at least 40%, at least 45%, or at least or about 50% of the molecules in the collection bears an identifying tag that is shared by at least one other molecule in the collection ("non-unique tag" or "non-unique identifier"). In some embodiments, for a non-uniquely tagged population, no more than 1%, 5%, 10%, 15%, 20%, 25%, 30%, 35%, 40%, 45%, or 50% of the molecules are uniquely tagged. In some embodiments, for unique tagging, at least two times as many different tags are used as the estimated number of molecules in the sample. The number of different identifying tags used to tag molecules in a collection can range, for example, between any of 2, 4, 8, 16, or 32 at the low end of the range, and any of 50, 100, 500, 1000, 5000 and 10,000 at the high end of the range. So, for example, a collection of between 100 billion and 1 trillion molecules can be tagged with between 4 and 100 different identifying tags.

The present disclosure provides methods and compositions in which a population of polynucleotides in a sample of fragmented genomic DNA is tagged with n different unique identifier. In some embodiments, n is at least 2 and no more than 100,000*z, wherein z is a measure of central tendency (e.g., mean, median, mode) of an expected number of duplicate molecules having the same start and stop positions. In some embodiments, z is 1, 2, 3, 4, 5, 6, 7, 8, 9, 10, or more than 10. In some embodiments, z is less than 10, less than 9, less than 8, less than 7, less than 6, less than 5, less than 4, less than 3. In certain embodiments, n is at least any of 2*z, 3*z, 4*z, 5*z, 6*z, 7*z, 8*z, 9*z, 10*z, 11*z, 12*z, 13*z, 14*z, 15*z, 16*z, 17*z, 18*z, 19*z, or 20*z (e.g., lower limit). In other embodiments, n is no greater than 100,000*z, 10,000*z, 1000*z or 100*z (e.g., upper limit). Thus, n can range between any combination of these lower and upper limits. In certain embodiments, n is between 5*z and 15*z, between 8*z and 12*z, or about 10*z. For example, a haploid human genome equivalent has about 3 picograms of DNA. A sample of about 1 microgram of DNA contains about 300,000 haploid human genome equivalents. In some embodiments, the number n can be between 5 and 95, 6 and 80, 8 and 75, 10 and 70, 15 and 45, between 24 and 36 or about 30. In some embodiments, the number n is less than 96. For example, the number n can be greater than or equal to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 3435, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95. In some situations, the number n can be greater than zero but less than 100, 99, 98, 97, 96, 95, 94, 93, 92, 91, or 90. In some examples, the number n is 64. The number n can be less than 75, less than 50, less than 40, less than 30, less than 20, less than 10, or less than 5. Improvements in sequencing can be achieved as long as at least some of the duplicate or cognate polynucleotides bear unique identifiers, that is, bear different tags. However, in certain embodiments, the number of tags used is selected so that there is at least a 95% chance that all duplicate molecules comprising the same start and end sequences bear unique identifiers.

Some embodiments provide methods for performing a ligation reaction in which parent polynucleotides in a sample are admixed with a reaction mixture comprising y different barcode oligonucleotides, wherein y=a square root of n. The ligation can result in the random attachment of barcode oligonucleotides to parent polynucleotides in the sample. The reaction mixture can then be incubated under ligation conditions sufficient to effect ligation of barcode oligonucleotides to parent polynucleotides of the sample. In some embodiments, random barcodes selected from the y different barcode oligonucleotides are ligated to both ends of parent polynucleotides. Random ligation of the y barcodes to one or both ends of the parent polynucleotides can result in production of $y^2$ unique identifiers. For example, a sample comprising about 10,000 haploid human genome equivalents of cfDNA can be tagged with about 36 unique identifiers. The unique identifiers can comprise six unique DNA barcodes. Ligation of 6 unique barcodes to both ends of a polynucleotide can result in 36 possible unique identifiers are produced.

In some embodiments, a sample comprising about 10,000 haploid human genome equivalents of DNA is tagged with 64 unique identifiers, wherein the 64 unique identifiers are produced by ligation of 8 unique barcodes to both ends of parent polynucleotides. The ligation efficiency of the reaction can be over 10%, over 20%, over 30%, over 40%, over 50%, over 60%, over 70%, over 80%, or over 90%. The ligation conditions can comprise use of bi-directional adaptors that can bind either end of the fragment and still be amplifiable. The ligation conditions can comprise blunt end ligation, as opposed to tailing with forked adaptors. The ligation conditions can comprise careful titration of an amount of adaptor and/or barcode oligonucleotides. The ligation conditions can comprise the use of over 2×, over 5×, over 10×, over 20×, over 40×, over 60×, over 80×, (e.g., ~100×) molar excess of adaptor and/or barcode oligonucleotides as compared to an amount of parent polynucleotide fragments in the reaction mixture. The ligation conditions can comprise use of a T4 DNA ligase (e.g., NEBNExt Ultra Ligation Module). In an example, 18 microliters of ligase master mix is used with 90 microliter ligation (18 part of the 90) and ligation enhancer. Accordingly, tagging parent polynucleotides with n unique identifiers can comprise use of a number y different barcodes, wherein y=a square root of n. Samples tagged in such a way can be those with a range of about 10 ng to any of about 100 ng, about 1 μg, about 10 μg of fragmented polynucleotides, e.g., genomic DNA, e.g. cfDNA. The number y of barcodes used to identify parent polynucleotides in a sample can depend on the amount of nucleic acid in the sample.

The present disclosure also provides compositions of tagged polynucleotides. The polynucleotides can comprise fragmented DNA, e.g. cfDNA. A set of polynucleotides in the composition that map to a mappable base position in a genome can be non-uniquely tagged, that is, the number of different identifiers can be at least at least 2 and fewer than the number of polynucleotides that map to the mappable base position. A composition of between about 10 ng to about 10 μg (e.g., any of about 10 ng-1 μg, about 10 ng-100 ng, about 100 ng-10 μg, about 100 ng-1 μg, about 1 μg-10 μg) can bear between any of 2, 5, 10, 50 or 100 to any of 100, 1000, 10,000 or 100,000 different identifiers. For example, between 5 and 100 different identifiers can be used to tag the polynucleotides in such a composition.

Figure 2:
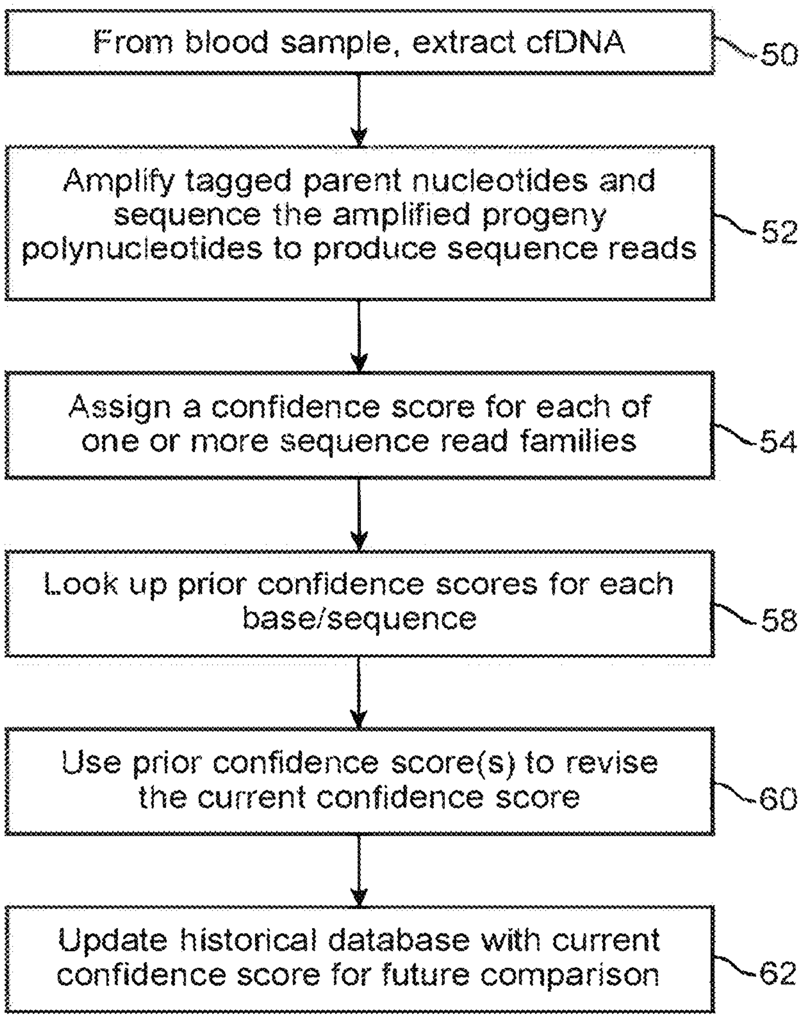
FIG. 2 illustrates an exemplary process for analyzing polynucleotides in a sample of initial genetic material.

FIG. 2 shows an exemplary process for analyzing polynucleotides in a sample of initial genetic material. First, a sample containing initial genetic material is provided and cell free DNA can be extracted (50). The sample can include target nucleic acid in low abundance. For example, nucleic acid from a normal or wild-type genome (e.g., a germline genome) can predominate in a sample that also includes no more than 20%, no more than 10%, no more than 5%, no more than 1%, no more than 0.5% or no more than 0.1% nucleic acid from at least one other genome containing genetic variation, e.g., a cancer genome or a fetal genome, or a genome from another individual or species. The sample can include, for example, cell free nucleic acid or cells comprising nucleic acid with proper oversampling of the original polynucleotides by the sequencing or genetic analysis process.

Next, the initial genetic material is converted into a set of tagged parent polynucleotides and sequenced to produce sequence reads (52). This step generates a plurality of genomic fragment sequence reads. In some cases, these sequences reads may contain barcode information. In other examples, barcodes are not utilized. Tagging can include attaching sequenced tags to molecules in the initial genetic material. Sequenced tags can be selected so that all unique polynucleotides mapping to the same reference sequence have a unique identifying tag. Conversion can be performed at high efficiency, for example at least 50%. The set of tagged parent polynucleotides can be amplified to produce a set of amplified progeny polynucleotides. Amplification may be, for example, 1,000-fold. The set of amplified progeny polynucleotides is sampled for sequencing at a sampling rate so that the sequence reads produced both (1) cover a target number of unique molecules in the set of tagged parent polynucleotides and (2) cover unique molecules in the set of tagged parent polynucleotides at a target coverage fold (e.g., 5- to 10-fold coverage of parent polynucleotides. The set of sequence reads is collapsed to produce a set of consensus sequences corresponding to unique tagged parent polynucleotides. Sequence reads can be qualified for inclusion in the analysis. For example, sequence reads that fail to meet a quality control score can be removed from the pool. Sequence reads can be sorted into families representing reads of progeny molecules derived from a particular unique parent molecule. For example, a family of amplified progeny polynucleotides can constitute those amplified molecules derived from a single parent polynucleotide. By comparing sequences of progeny in a family, a consensus sequence of the original parent polynucleotide can be deduced. This produces a set of consensus sequences representing unique parent polynucleotides in the tagged pool.

Next, the process assigns a confidence score for the sequence (54). After sequencing, reads are assigned a quality score. A quality score may be a representation of reads that indicates whether those reads may be useful in subsequent analysis based on a threshold. In some cases, some reads are not of sufficient quality or length to perform the subsequent mapping step. Sequencing reads with a predetermined quality score (above 90% for example) may be filtered out of the data. The genomic fragment reads that meet a specified quality score threshold are mapped to a reference genome, or a template sequence that is known not to contain copy number variations. After mapping alignment, sequence reads are assigned a mapping score. A mapping score may be a representation or reads mapped back to the reference sequence indicating whether each position is or is not uniquely mappable. In instances, reads may be sequences unrelated to copy number variation analysis. For example, some sequence reads may originate from contaminant polynucleotides. Sequencing reads with a mapping score at least 90%, 95%, 99%, 99.9%, 99.99% or 99.999% may be filtered out of the data set. In other cases, sequencing reads assigned a mapping scored less than a predetermined percentage may be filtered out of the data set.

The genomic fragment reads that meet a specified quality score threshold are mapped to a reference genome, or a template sequence that is known not to contain copy number variations. After mapping alignment, sequence reads are assigned a mapping score. In instances, reads may be sequences unrelated to copy number variation analysis. After data filtering and mapping, the plurality of sequence reads generates a chromosomal region of coverage. These chromosomal regions may be divided into variable length windows or bins. A window or bin may be at least 5 kb, 10, kb, 25 kb, 30 kb, 35, kb, 40 kb, 50 kb, 60 kb, 75 kb, 100 kb, 150 kb, 200 kb, 500 kb, or 1000 kb. A window or bin may also have bases up to 5 kb, 10, kb, 25 kb, 30 kb, 35, kb, 40 kb, 50 kb, 60 kb, 75 kb, 100 kb, 150 kb, 200 kb, 500 kb, or 1000 kb. A window or bin may also be about 5 kb, 10, kb, 25 kb, 30 kb, 35, kb, 40 kb, 50 kb, 60 kb, 75 kb, 100 kb, 150 kb, 200 kb, 500 kb, or 1000 kb.

For coverage normalization, each window or bin is selected to contain about the same number of mappable bases. In some cases, each window or bin in a chromosomal region may contain the exact number of mappable bases. In other cases, each window or bin may contain a different number of mappable bases. Additionally, each window or bin may be non-overlapping with an adjacent window or bin. In other cases, a window or bin may overlap with another adjacent window or bin. In some cases a window or bin may overlap by at least 1 bp, 2 bp, 3 bp, 4 bp, 5, bp, 10 bp, 20 bp, 25 bp, 50 bp, 100 bp, 200 bp, 250 bp, 500 bp, or 1000 bp.

In some cases, each of the window regions may be sized so they contain about the same number of uniquely mappable bases. The mappability of each base that comprise a window region is determined and used to generate a mappability file which contains a representation of reads from the references that are mapped back to the reference for each file. The mappability file contains one row per every position, indicating whether each position is or is not uniquely mappable.

Additionally, predefined windows, known throughout the genome to be hard to sequence, or contain a substantially high GC bias, may be filtered from the data set. For example, regions known to fall near the centromere of chromosomes (i.e., centromeric DNA) are known to contain highly repetitive sequences that may produce false positive results. These regions may be filtered out. Other regions of the genome, such as regions that contain an unusually high concentration of other highly repetitive sequences such as microsatellite DNA, may be filtered from the data set.

The number of windows analyzed may also vary. In some cases, at least 10, 20, 30, 40, 50, 100, 200, 500, 1000, 2000, 5,000, 10,000, 20,000, 50,000 or 100,000 windows are analyzed. In other cases, the number of widows analyzed is up to 10, 20, 30, 40, 50, 100, 200, 500, 1000, 2000, 5,000, 10,000, 20,000, 50,000 or 100,000 windows are analyzed.

For an exemplary genome derived from cell free polynucleotide sequences, the next step comprises determining read coverage for each window region. This may be performed using either reads with barcodes, or without barcodes. In cases without barcodes, the previous mapping steps will provide coverage of different base positions. Sequence reads that have sufficient mapping and quality scores and fall within chromosome windows that are not filtered, may be counted. The number of coverage reads may be assigned a score per each mappable position. In cases involving barcodes, all sequences with the same barcode, physical properties or combination of the two may be collapsed into one read, as they are all derived from the sample parent molecule. This step reduces biases which may have been introduced during any of the preceding steps, such as steps involving amplification. For example, if one molecule is amplified 10 times but another is amplified 1000 times, each molecule is only represented once after collapse thereby negating the effect of uneven amplification. Only reads with unique barcodes may be counted for each mappable position and influence the assigned score. For this reason, it is important that the barcode ligation step be performed in a manner optimized for producing the lowest amount of bias. The sequence for each base is aligned as the most dominant nucleotide read for that specific location. Further, the number of unique molecules can be counted at each position to derive simultaneous quantification at each position. This step reduces biases which may have been introduced during any of the preceding steps, such as steps involving amplification.

The discrete copy number states of each window region can be utilized to identify copy number variation in the chromosomal regions. In some cases, all adjacent window regions with the same copy number can be merged into a segment to report the presence or absence of copy number variation state. In some cases, various windows can be filtered before they are merged with other segments.

In determining the nucleic acid read coverage for each window, the coverage of each window can be normalized by the mean coverage of that sample. Using such an approach, it may be desirable to sequence both the test subject and the control under similar conditions. The read coverage for each window may be then expressed as a ratio across similar windows.

Nucleic acid read coverage ratios for each window of the test subject can be determined by dividing the read coverage of each window region of the test sample with read coverage of a corresponding window region of the control ample.

Next, the process looks up prior confidence scores for each read family for the patient (58). This information is stored in a database. Prior analysis of the patient's test result can be used to refine the confidence score, as detailed in FIG. 2. The information is used to infer the frequency of each sequence read at a locus in the set of tagged parent polynucleotides based on confidence scores among sequence read families (60). The historical database is then updated with the current confidence score for future use (62). In this manner, consensus sequences can be generated from families of sequence reads to improve noise elimination.

Figure 3:
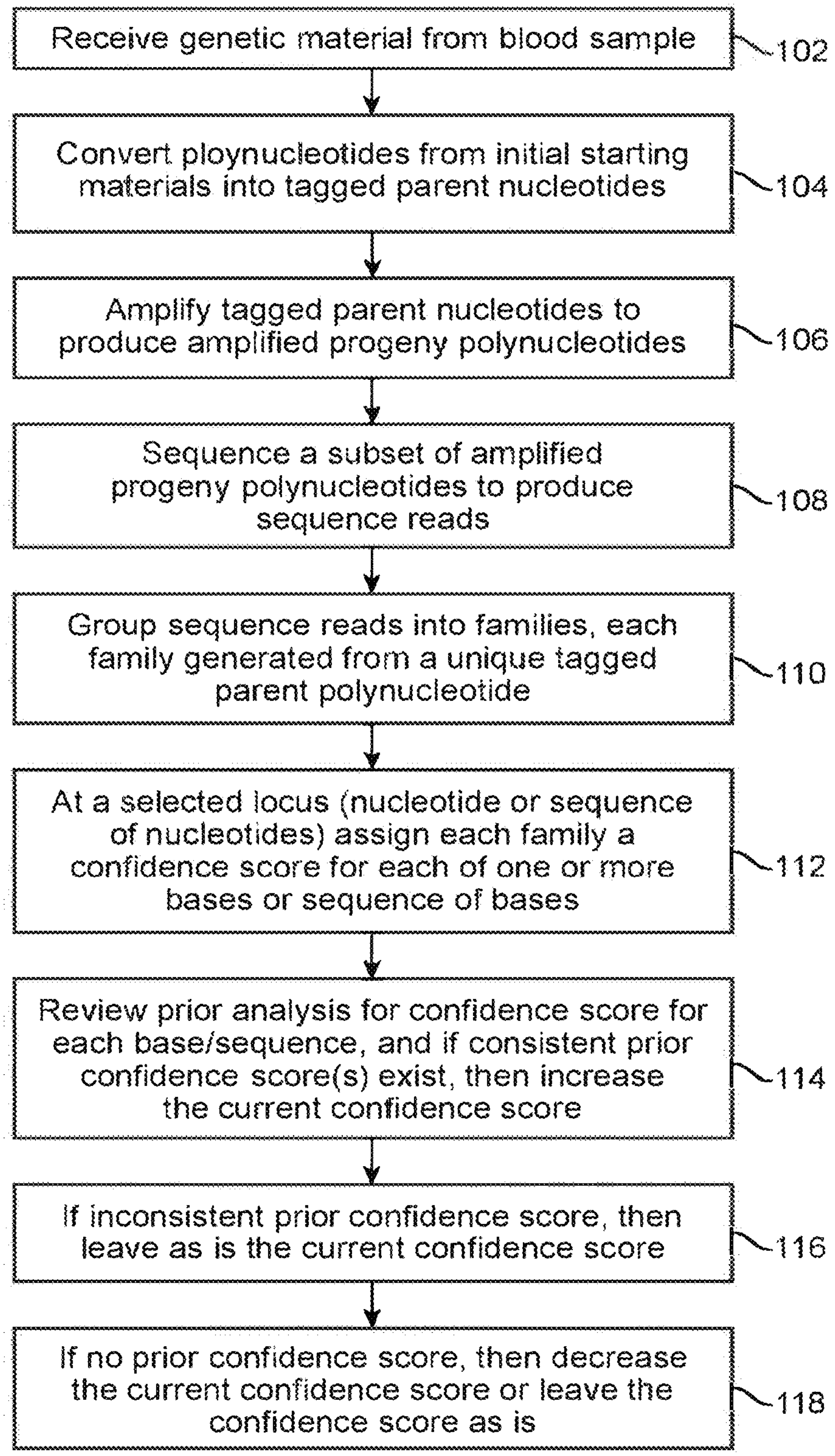
FIG. 3 illustrates another exemplary process for analyzing polynucleotides in a sample of initial genetic material.

Turning now to FIG. 3, the process receives genetic materials from blood sample or other body samples (102). The process converts the polynucleotides from the genetic materials into tagged parent nucleotides (104). The tagged parent nucleotides are amplified to produce amplified progeny polynucleotides (106). A subset of the amplified polynucleotides is sequenced to produce sequence reads (108), which are grouped into families, each generated from a unique tagged parent nucleotide (110). At a selected locus, the process assigns each family a confidence score for each family (112). Next, a consensus is determined using prior readings. This is done by reviewing prior confidence score for each family, and if consistent prior confidence scores exists, then the current confidence score is increased (114). If there are prior confidence scores, but they are inconsistent, the current confidence score is not modified in one embodiment (116). In other embodiments, the confidence score is adjusted in a predetermined manner for inconsistent prior confidence scores. If this is a first time the family is detected, the current confidence score can be reduced as it may be a false reading (118). The process can infer the frequency of the family at the locus in the set of tagged parent polynucleotides based on the confidence score (120).

While temporal information has been used in FIGS. 1-2 to enhance the information for mutation or copy number variation detection, other consensus methods can be applied. In other embodiments, the historical comparison can be used in conjunction with other consensus sequences mapping to a particular reference sequence to detect instances of genetic variation. Consensus sequences mapping to particular reference sequences can be measured and normalized against control samples. Measures of molecules mapping to reference sequences can be compared across a genome to identify areas in the genome in which copy number varies, or heterozygosity is lost. Consensus methods include, for example, linear or non-linear methods of building consensus sequences (such as voting, averaging, statistical, maximum a posteriori or maximum likelihood detection, dynamic programming, Bayesian, hidden Markov or support vector machine methods, etc.) derived from digital communication theory, information theory, or bioinformatics. After the sequence read coverage has been determined, a stochastic modeling algorithm is applied to convert the normalized nucleic acid sequence read coverage for each window region to the discrete copy number states. In some cases, this algorithm may comprise one or more of the following: Hidden Markov Model, dynamic programming, support vector machine, Bayesian network, trellis decoding, Viterbi decoding, expectation maximization, Kalman filtering methodologies and neural networks.

After this, a report can be generated. For example, the copy number variation may be reported as graph, indicating various positions in the genome and a corresponding increase or decrease or maintenance of copy number variation at each respective position. Additionally, copy number variation may be used to report a percentage score indicating how much disease material (or nucleic acids having a copy number variation) exists in the cell free polynucleotide sample.

In one embodiment, the report includes annotations to help physicians. The annotating can include annotating a report for a condition in the NCCN Clinical Practice Guidelines in Oncology™ or the American Society of Clinical Oncology (ASCO) clinical practice guidelines. The annotating can include listing one or more FDA-approved drugs for off-label use, one or more drugs listed in a Centers for Medicare and Medicaid Services (CMS) anti-cancer treatment compendia, and/or one or more experimental drugs found in scientific literature, in the report. The annotating can include connecting a listed drug treatment option to a reference containing scientific information regarding the drug treatment option. The scientific information can be from a peer-reviewed article from a medical journal. The annotating can include using information provided by Ingenuity® Systems. The annotating can include providing a link to information on a clinical trial for a drug treatment option in the report. The annotating can include presenting information in a pop-up box or fly-over box near provided drug treatment options in an electronic based report. The annotating can include adding information to a report selected from the group consisting of one or more drug treatment options, scientific information concerning one or more drug treatment options, one or more links to scientific information regarding one or more drug treatment options, one or more links to citations for scientific information regarding one or more drug treatment options, and clinical trial information regarding one or more drug treatment options.

Figure 4:
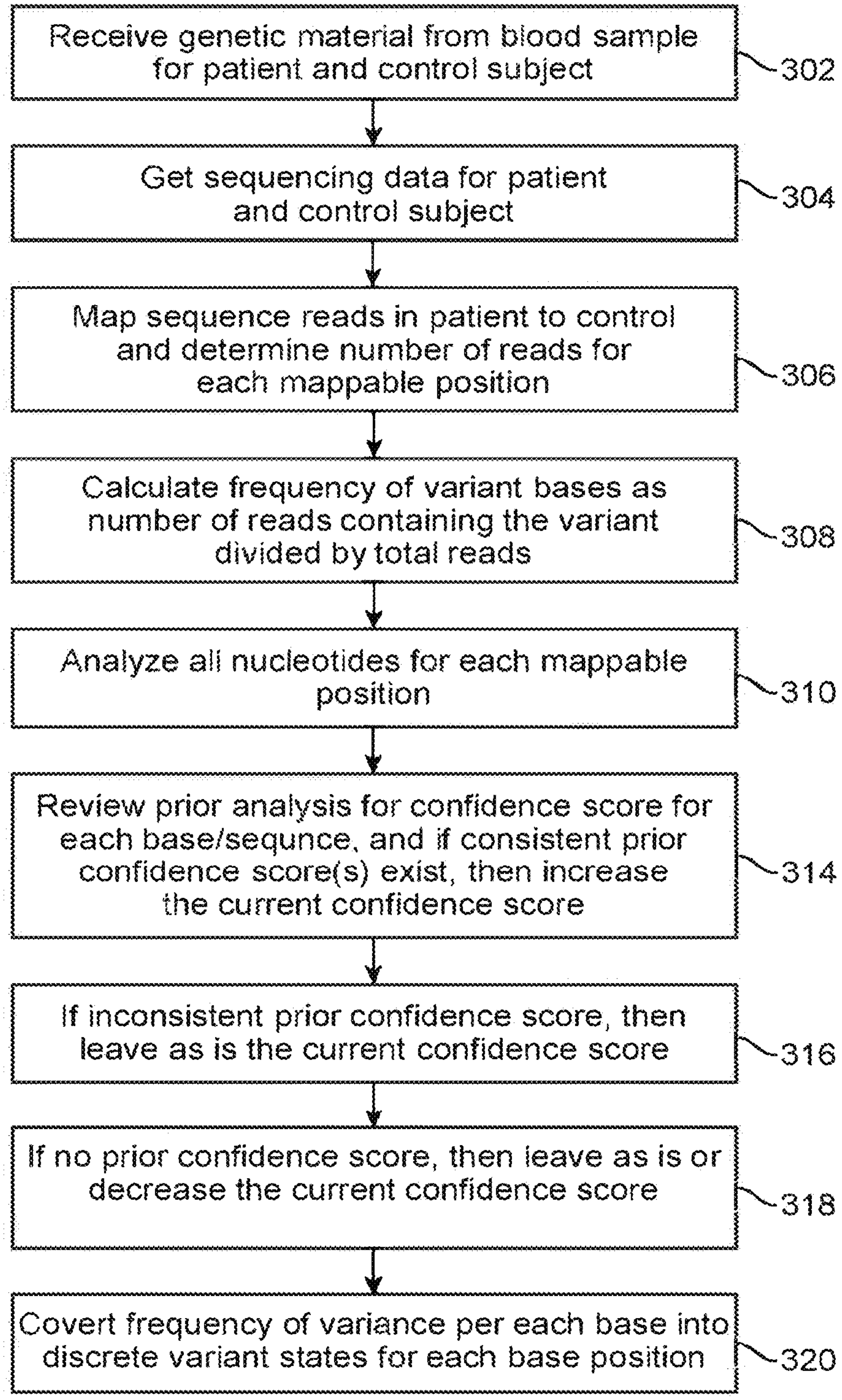
FIG. 4 illustrates another exemplary process for analyzing polynucleotides in a sample of initial genetic material.

As depicted in FIG. 4, a comparison of sequence coverage to a control sample or reference sequence may aid in normalization across windows. In this embodiment, cell free DNAs are extracted and isolated from a readily accessible bodily fluid such as blood. For example, cell free DNAs can be extracted using a variety of methods recognized in the art, including but not limited to isopropanol precipitation and/or silica based purification. Cell free DNAs may be extracted from any number of subjects, such as subjects without cancer, subjects at risk for cancer, or subjects known to have cancer.

Following the isolation/extraction step, any of a number of different sequencing operations may be performed on the cell free polynucleotide sample. Samples may be processed before sequencing with one or more reagents (e.g., enzymes, unique identifiers (e.g., barcodes), probes, etc.). In some cases if the sample is processed with a unique identifier such as a barcode, the samples or fragments of samples may be tagged individually or in subgroups with the unique identifier. The tagged sample may then be used in a downstream application such as a sequencing reaction by which individual molecules may be tracked to parent molecules.

Generally, as shown in FIG. 4, mutation detection may be performed on selectively enriched regions of the genome or transcriptome purified and isolated (302). As described herein, specific regions, which may include but are not limited to genes, oncogenes, tumor suppressor genes, promoters, regulatory sequence elements, non-coding regions, miRNAs, snRNAs and the like may be selectively amplified from a total population of cell free polynucleotides. This may be performed as herein described. In one example, multiplex sequencing may be used, with or without barcode labels for individual polynucleotide sequences. In other examples, sequencing may be performed using any nucleic acid sequencing platforms recognized in the art. This step generates a plurality of genomic fragment sequence reads (304). Additionally, a reference sequence is obtained from a control sample, taken from another subject. In some cases, the control subject may be a subject known to not have known genetic variations or disease. In some cases, these sequence reads may contain barcode information. In other examples, barcodes are not utilized. In yet other examples, non-unique sequence tags are used.

After sequencing, reads are assigned a quality score. A quality score may be a representation of reads that indicates whether those reads may be useful in subsequent analysis based on a threshold. In some cases, some reads are not of sufficient quality or length to perform the subsequent mapping step. In step 306, the genomic fragment reads that meet a specified quality score threshold are mapped to a reference genome, or a reference sequence that is known not to contain mutations. After mapping alignment, sequence reads are assigned a mapping score. A mapping score may be a representation or reads mapped back to the reference sequence indicating whether each position is or is not uniquely mappable. In instances, reads may be sequences unrelated to mutation analysis. For example, some sequence reads may originate from contaminant polynucleotides. Sequencing reads with a mapping score at least 90%, 95%, 99%, 99.9%, 99.99% or 99.999% may be filtered out of the data set. In other cases, sequencing reads assigned a mapping scored less than 90%, 95%, 99%, 99.9%, 99.99% or 99.999% may be filtered out of the data set.

For each mappable base, bases that do not meet the minimum threshold for mappability, or low quality bases, may be replaced by the corresponding bases as found in the reference sequence.

Once read coverage may be ascertained and variant bases relative to the control sequence in each read are identified, the frequency of variant bases may be calculated as the number of reads containing the variant divided by the total number of reads (308). This may be expressed as a ratio for each mappable position in the genome.

For each base position, the frequencies of all four nucleotides, cytosine, guanine, thymine, adenine are analyzed in comparison to the reference sequence (310). A stochastic or statistical modeling algorithm is applied to convert the normalized ratios for each mappable position to reflect frequency states for each base variant. In some cases, this algorithm may comprise one or more of the following: Hidden Markov Model, dynamic programming, support vector machine, Bayesian or probabilistic modeling, trellis decoding, Viterbi decoding, expectation maximization, Kalman filtering methodologies, and neural networks.

The discrete mutation states of each base position can be utilized to identify a base variant with high frequency of variance as compared to the baseline of the reference sequence. In some cases, the baseline might represent a frequency of at least 0.0001%, 0.001%, 0.01%, 0.1%, 1.0%, 2.0%, 3.0%, 4.0% 5.0%, 10%, or 25%. In other cases the baseline might represent a frequency of at least 0.0001%, 0.001%, 0.01%, 0.1%, 1.0%, 2.0%, 3.0%, 4.0% 5.0%, 10%, or 25%. In some cases, all adjacent base positions with the base variant or mutation can be merged into a segment to report the presence or absence of a mutation. In some cases, various positions can be filtered before they are merged with other segments.

After calculation of frequencies of variance for each base position, the variant with largest deviation for a specific position in the sequence derived from the subject as compared to the reference sequence is identified as a mutation. In some cases, a mutation may be a cancer mutation. In other cases, a mutation might be correlated with a disease state.

A mutation or variant may comprise a genetic aberration that includes, but is not limited to a single base substitution, a transversion, a translocation, an inversion, a deletion, aneuploidy, partial aneuploidy, polyploidy, chromosomal instability, chromosomal structure alterations, chromosome fusions, a gene truncation, a gene amplification, a gene duplication, a chromosomal lesion, a DNA lesion, abnormal changes in nucleic acid chemical modifications, abnormal changes in epigenetic patterns and abnormal changes in nucleic acid methylation. In some cases, a mutation may be at most 1, 2, 3, 4, 5, 6, 7, 8, 9, 10, 15 or 20 nucleotides in length. On other cases a mutation may be at least 1, 2, 3, 4, 5, 6, 7, 8, 9, 10, 15 or 20 nucleotides in length.

Next, a consensus is determined using prior readings. This is done by reviewing prior confidence score for the corresponding bases, and if consistent prior confidence scores exists, then the current confidence score is increased (314). If there are prior confidence scores, but they are inconsistent, the current confidence score is not modified in one embodiment (316). In other embodiments, the confidence score is adjusted in a predetermined manner for inconsistent prior confidence scores. If this is a first time the family is detected, the current confidence score can be reduced as it may be a false reading (318). The process then converts the frequency of variance per each base into discrete variant states for each base position (320).

The presence or absence of a mutation may be reflected in graphical form, indicating various positions in the genome and a corresponding increase or decrease or maintenance of a frequency of mutation at each respective position. Additionally, mutations may be used to report a percentage score indicating how much disease material exists in the cell free polynucleotide sample. A confidence score may accompany each detected mutation, given known statistics of typical variances at reported positions in non-disease reference sequences. Mutations may also be ranked in order of abundance in the subject or ranked by clinically actionable importance.

Next, applications of the technology are detailed. One application is Detection of Cancer. Numerous cancers may be detected using the methods and systems described herein. Cancers cells, as most cells, can be characterized by a rate of turnover, in which old cells die and replaced by newer cells. Generally dead cells, in contact with vasculature in a given subject, may release DNA or fragments of DNA into the blood stream. This is also true of cancer cells during various stages of the disease. Cancer cells may also be characterized, dependent on the stage of the disease, by various genetic variations such as copy number variation as well as mutations. This phenomenon may be used to detect the presence or absence of cancers individuals using the methods and systems described herein.

For example, blood from subjects at risk for cancer may be drawn and prepared as described herein to generate a population of cell free polynucleotides. In one example, this might be cell free DNA. The systems and methods of the disclosure may be employed to detect mutations or copy number variations that may exist in certain cancers present.

The method may help detect the presence of cancerous cells in the body, despite the absence of symptoms or other hallmarks of disease.

The types and number of cancers that may be detected may include but are not limited to blood cancers, brain cancers, lung cancers, skin cancers, nose cancers, throat cancers, liver cancers, bone cancers, lymphomas, pancreatic cancers, skin cancers, bowel cancers, rectal cancers, thyroid cancers, bladder cancers, kidney cancers, mouth cancers, stomach cancers, solid state tumors, heterogeneous tumors, homogenous tumors and the like.

In the early detection of cancers, any of the systems or methods herein described, including mutation detection or copy number variation detection may be utilized to detect cancers. These system and methods may be used to detect any number of genetic variations that may cause or result from cancers. These may include but are not limited to mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, abnormal changes in nucleic acid methylation infection and cancer.

Additionally, the systems and methods described herein may also be used to help characterize certain cancers. Genetic data produced from the system and methods of this disclosure may allow practitioners to help better characterize a specific form of cancer. Cancers may be heterogeneous in both composition and staging. Genetic profile data may allow characterization of specific sub-types of cancer that may be important in the diagnosis or treatment of that specific sub-type. This information may also provide a subject or practitioner clues regarding the prognosis of a specific type of cancer.

The systems and methods provided herein may be used to monitor cancers, or other diseases in a particular subject. This may allow either a subject or practitioner to adapt treatment options in accord with the progress of the disease. In this example, the systems and methods described herein may be used to construct genetic profiles of a particular subject of the course of the disease. In some instances, cancers can progress, becoming more aggressive and genetically unstable. In other examples, cancers may remain benign, inactive or dormant. The system and methods of this disclosure may be useful in determining disease progression.

Further, the systems and methods described herein may be useful in determining the efficacy of a particular treatment option. In one example, successful treatment options may actually increase the amount of copy number variation or mutations detected in subject's blood if the treatment is successful as more cancers may die and shed DNA. In other examples, this may not occur. In another example, perhaps certain treatment options may be correlated with genetic profiles of cancers over time. This correlation may be useful in selecting a therapy. Additionally, if a cancer is observed to be in remission after treatment, the systems and methods described herein may be useful in monitoring residual disease or recurrence of disease.

The methods and systems described herein may not be limited to detection of mutations and copy number variations associated with only cancers. Various other diseases and infections may result in other types of conditions that may be suitable for early detection and monitoring. For example, in certain cases, genetic disorders or infectious diseases may cause a certain genetic mosaicism within a subject. This genetic mosaicism may cause copy number variation and mutations that could be observed. In another example, the system and methods of the disclosure may also be used to monitor the genomes of immune cells within the body. Immune cells, such as B cells, may undergo rapid clonal expansion upon the presence certain diseases. Clonal expansions may be monitored using copy number variation detection and certain immune states may be monitored. In this example, copy number variation analysis may be performed over time to produce a profile of how a particular disease may be progressing.

Further, the systems and methods of this disclosure may also be used to monitor systemic infections themselves, as may be caused by a pathogen such as a bacteria or virus. Copy number variation or even mutation detection may be used to determine how a population of pathogens are changing during the course of infection. This may be particularly important during chronic infections, such as HIV/AIDS or Hepatitis infections, whereby viruses may change life cycle state and/or mutate into more virulent forms during the course of infection.

Yet another example that the system and methods of this disclosure may be used for is the monitoring of transplant subjects. Generally, transplanted tissue undergoes a certain degree of rejection by the body upon transplantation. The methods of this disclosure may be used to determine or profile rejection activities of the host body, as immune cells attempt to destroy transplanted tissue. This may be useful in monitoring the status of transplanted tissue as well as altering the course of treatment or prevention of rejection.

Further, the methods of the disclosure may be used to characterize the heterogencity of an abnormal condition in a subject, the method comprising generating a genetic profile of extracellular polynucleotides in the subject, wherein the genetic profile comprises a plurality of data resulting from copy number variation and mutation analyses. In some cases, including but not limited to cancer, a disease may be heterogeneous. Disease cells may not be identical. In the example of cancer, some tumors comprise different types of tumor cells, some cells in different stages of the cancer. In other examples, heterogeneity may comprise multiple foci of disease. Again, in the example of cancer, there may be multiple tumor foci, perhaps where one or more foci are the result of metastases that have spread from a primary site.

The methods of this disclosure may be used to generate or profile, fingerprint or set of data that is a summation of genetic information derived from different cells in a heterogeneous disease. This set of data may comprise copy number variation and mutation analyses alone or in combination.

Additionally, the systems and methods of the disclosure may be used to diagnose, prognose, monitor or observe cancers or other diseases of fetal origin. That is, these methodologies may be employed in a pregnant subject to diagnose, prognose, monitor or observe cancers or other diseases in a unborn subject whose DNA and other polynucleotides may co-circulate with maternal molecules.

Further, these reports are submitted and accessed electronically via the internet. Analysis of sequence data occurs at a site other than the location of the subject. The report is generated and transmitted to the subject's location. Via an internet enabled computer, the subject accesses the reports reflecting his tumor burden.

The annotated information can be used by a health care provider to select other drug treatment options and/or provide information about drug treatment options to an insurance company. The method can include annotating the drug treatment options for a condition in, for example, the NCCN Clinical Practice Guidelines in Oncology™ or the American Society of Clinical Oncology (ASCO) clinical practice guidelines.

The drug treatment options that are stratified in a report can be annotated in the report by listing additional drug treatment options. An additional drug treatment can be an FDA-approved drug for an off-label use. A provision in the 1993 Omnibus Budget Reconciliation Act (OBRA) requires Medicare to cover off-label uses of anticancer drugs that are included in standard medical compendia. The drugs used for annotating lists can be found in CMS approved compendia, including the National Comprehensive Cancer Network (NCCN) Drugs and Biologics Compendium™, Thomson Micromedex DrugDex®, Elsevier Gold Standard's Clinical Pharmacology compendium, and American Hospital Formulary Service—Drug Information Compendium®.

The drug treatment options can be annotated by listing an experimental drug that may be useful in treating a cancer with one or more molecular markers of a particular status. The experimental drug can be a drug for which in vitro data, in vivo data, animal model data, pre-clinical trial data, or clinical-trial data are available. The data can be published in peer-reviewed medical literature found in journals listed in the CMS Medicare Benefit Policy Manual, including, for example, American Journal of Medicine, Annals of Internal Medicine, Annals of Oncology, Annals of Surgical Oncology, Biology of Blood and Marrow Transplantation, Blood, Bone Marrow Transplantation, British Journal of Cancer, British Journal of Hematology, British Medical Journal, Cancer, Clinical Cancer Research, Drugs, European Journal of Cancer (formerly the European Journal of Cancer and Clinical Oncology), Gynecologic Oncology, International Journal of Radiation, Oncology, Biology, and Physics, The Journal of the American Medical Association, Journal of Clinical Oncology, Journal of the National Cancer Institute, Journal of the National Comprehensive Cancer Network (NCCN), Journal of Urology, Lancet, Lancet Oncology, Leukemia, The New England Journal of Medicine, and Radiation Oncology.

The drug treatment options can be annotated by providing a link on an electronic based report connecting a listed drug to scientific information regarding the drug. For example, a link can be provided to information regarding a clinical trial for a drug (clinicaltrials.gov). If the report is provided via a computer or computer website, the link can be a footnote, a hyperlink to a website, a pop-up box, or a fly-over box with information, etc. The report and the annotated information can be provided on a printed form, and the annotations can be, for example, a footnote to a reference.

The information for annotating one or more drug treatment options in a report can be provided by a commercial entity that stores scientific information, for example, Ingenuity® Systems. A health care provider can treat a subject, such as a cancer patient, with an experimental drug listed in the annotated information, and the health care provider can access the annotated drug treatment option, retrieve the scientific information (e.g., print a medical journal article) and submit it (e.g., a printed journal article) to an insurance company along with a request for reimbursement for providing the drug treatment. Physicians can use any of a variety of Diagnosis-related group (DRG) codes to enable reimbursement.

A drug treatment option in a report can also be annotated with information regarding other molecular components in a pathway that a drug affects (e.g., information on a drug that targets a kinase downstream of a cell-surface receptor that is a drug target). The drug treatment option can be annotated with information on drugs that target one or more other molecular pathway components. The identification and/or annotation of information related to pathways can be outsourced or subcontracted to another company.

The annotated information can be, for example, a drug name (e.g., an FDA approved drug for off-label use; a drug found in a CMS approved compendium, and/or a drug described in a scientific (medical) journal article), scientific information concerning one or more drug treatment options, one or more links to scientific information regarding one or more drugs, clinical trial information regarding one or more drugs (e.g., information from clinicaltrials.gov/), one or more links to citations for scientific information regarding drugs, etc.

The annotated information can be inserted into any location in a report. Annotated information can be inserted in multiple locations on a report. Annotated information can be inserted in a report near a section on stratified drug treatment options. Annotated information can be inserted into a report on a separate page from stratified drug treatment options. A report that does not contain stratified drug treatment options can be annotated with information.

The provided methods can also be utilized for investigating the effects of drugs on sample (e.g. tumor cells) isolated from a subject (e.g. cancer patient). An in vitro culture using a tumor from a cancer patient can be established using techniques recognized by those skilled in the art.

The provided method can also include high-throughput screening of FDA approved off-label drugs or experimental drugs using the in vitro culture and/or xenograft model.

The provided method can also include monitoring tumor antigen for recurrence detection.

Figure 5A:
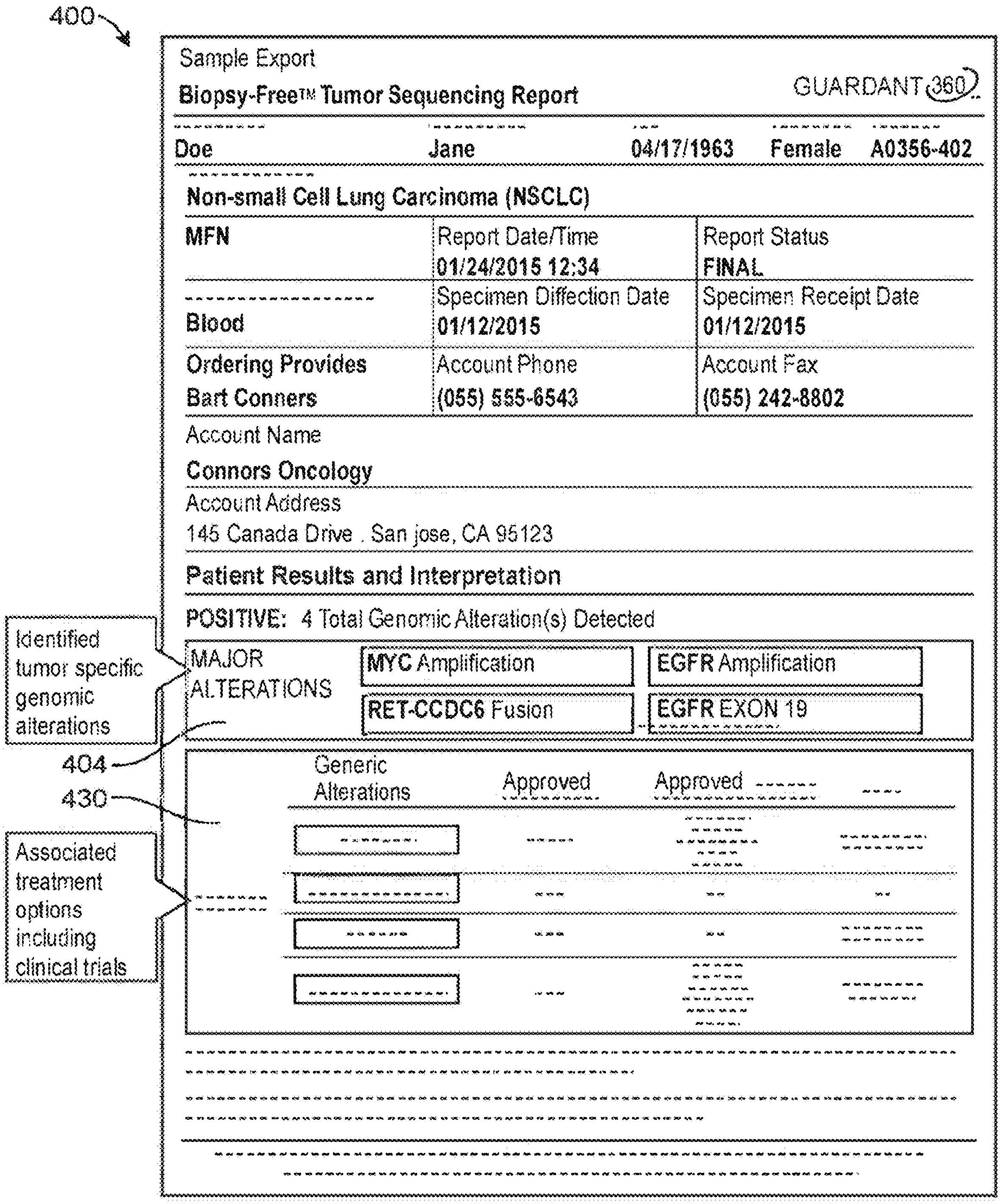
FIGS. 5A and 5B show schematic representations of internet enabled access of reports generated from copy number variation analysis of a subject with cancer.
Figure 5B:
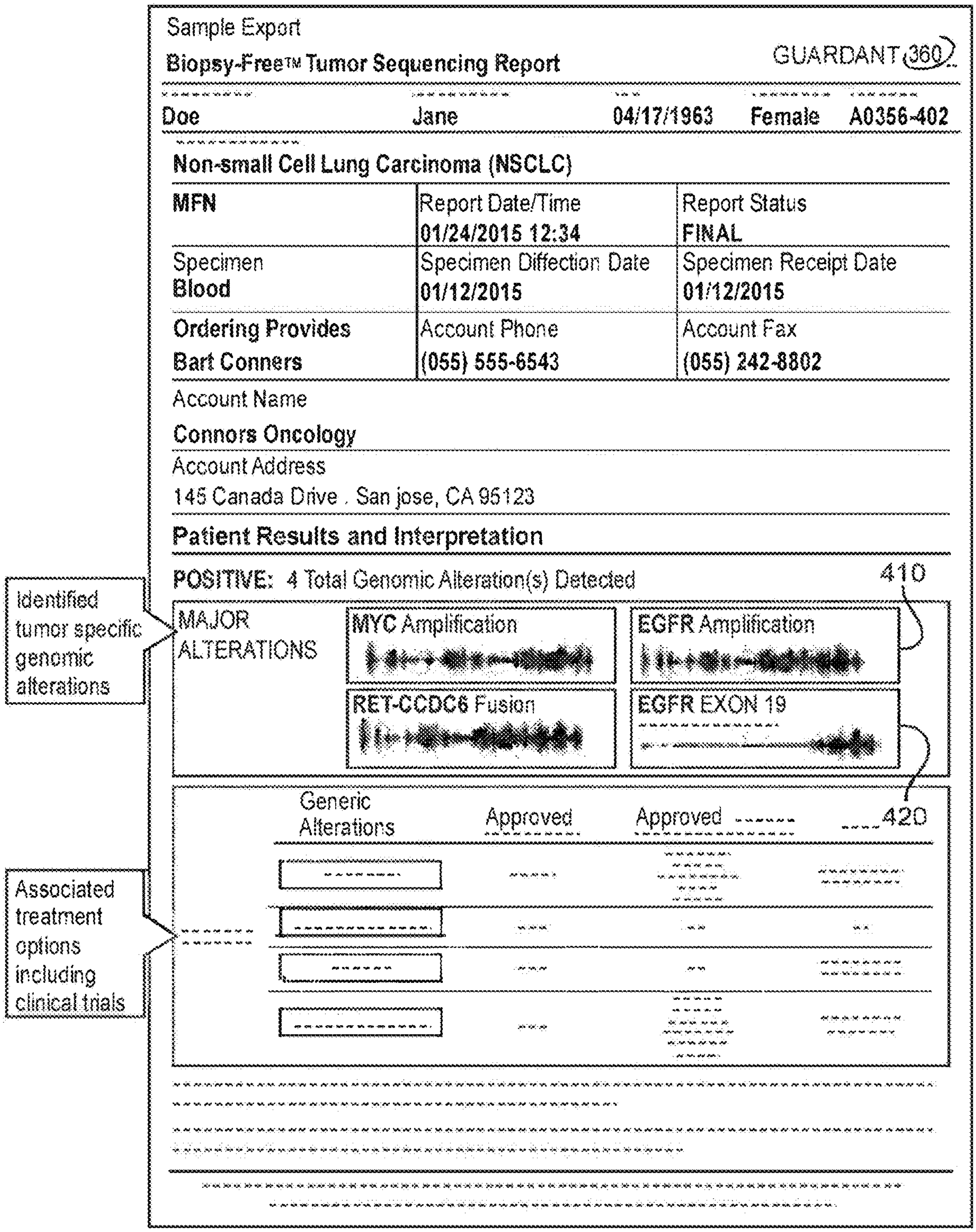

Reports may be generated, mapping genome positions and copy number variation for the subject with cancer, as shown in FIGS. 5A and 5B. These reports, in comparison to other profiles of subjects with known outcomes, can indicate that a particular cancer is aggressive and resistant to treatment. The subject is monitored for a period and retested. If at the end of the period, the copy number variation profile begins to increase dramatically, this may indicate that the current treatment is not working. A comparison is done with genetic profiles of other prostate subjects. For example, if it is determined that this increase in copy number variation indicates that the cancer is advancing, then the original treatment regimen as prescribed is no longer treating the cancer and a new treatment is prescribed.

In an embodiment, the system supports the gene panel shown in FIG. 9. The gene panel of FIG. 9 may be used with methods and systems of the present disclosure.

These reports may be submitted and accessed electronically via the internet. Analysis of sequence data occurs at a site other than the location of the subject. The report is generated and transmitted to the subject's location. Via an internet enabled computer, the subject accesses the reports reflecting his tumor burden (FIGS. 5A and 5B).

Figure 6:
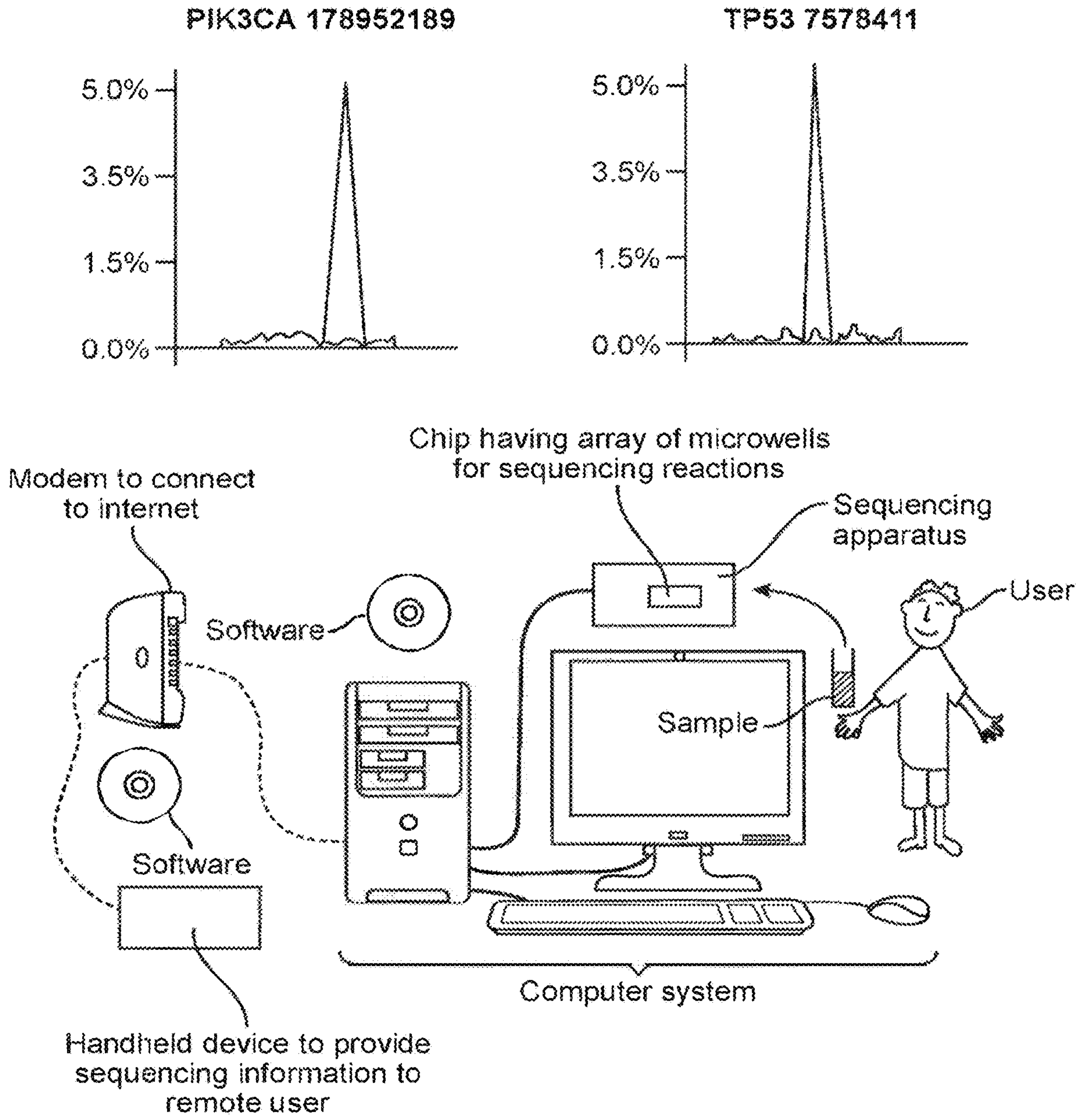
FIG. 6 shows a schematic representation of internet enabled access of reports of a subject with cancer.

FIG. 6 is schematic representation of internet enabled access of reports of a subject with cancer. The system of FIG. 6 can use a handheld DNA sequencer or a desktop DNA sequencer. The DNA sequencer is a scientific instrument used to automate the DNA sequencing process. Given a sample of DNA, a DNA sequencer is used to determine the order of the four bases: adenine, guanine, cytosine, and thymine. The order of the DNA bases is reported as a text string, called a read. Some DNA sequencers can be also considered optical instruments as they analyze light signals originating from fluorochromes attached to nucleotides.

The DNA sequencer can apply Gilbert's sequencing method based on chemical modification of DNA followed by cleavage at specific bases, or it can apply Sanger's technique which is based on dideoxynucleotide chain termination. The Sanger method became popular due to its increased efficiency and low radioactivity. The DNA sequencer can use techniques that do not require DNA amplification (polymerase chain reaction-PCR), which speeds up the sample preparation before sequencing and reduces errors. In addition, sequencing data is collected from the reactions caused by the addition of nucleotides in the complementary strand in real time. For example, the DNA sequencers can utilize a method called Single-molecule real-time (SMRT), where sequencing data is produced by light (captured by a camera) emitted when a nucleotide is added to the complementary strand by enzymes containing fluorescent dyes. Alternatively, the DNA sequencers can use electronic systems based on nanopore sensing technologies.

The data is sent by the DNA sequencers over a direct connection or over the internet to a computer for processing. The data processing aspects of the system can be implemented in digital electronic circuitry, or in computer hardware, firmware, software, or in combinations of them. Data processing apparatus of the invention can be implemented in a computer program product tangibly embodied in a machine-readable storage device for execution by a programmable processor; and data processing method steps of the invention can be performed by a programmable processor executing a program of instructions to perform functions of the invention by operating on input data and generating output. The data processing aspects of the invention can be implemented advantageously in one or more computer programs that are executable on a programmable system including at least one programmable processor coupled to receive data and instructions from and to transmit data and instructions to a data storage system, at least one input device, and at least one output device. Each computer program can be implemented in a high-level procedural or object-oriented programming language, or in assembly or machine language, if desired; and, in any case, the language can be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of nonvolatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICS (application-specific integrated circuits).

To provide for interaction with a user, the invention can be implemented using a computer system having a display device such as a monitor or LCD (liquid crystal display) screen for displaying information to the user and input devices by which the user can provide input to the computer system such as a keyboard, a two-dimensional pointing device such as a mouse or a trackball, or a three-dimensional pointing device such as a data glove or a gyroscopic mouse. The computer system can be programmed to provide a graphical user interface through which computer programs interact with users. The computer system can be programmed to provide a virtual reality, three-dimensional display interface.

Computer Control Systems

Figure 7:
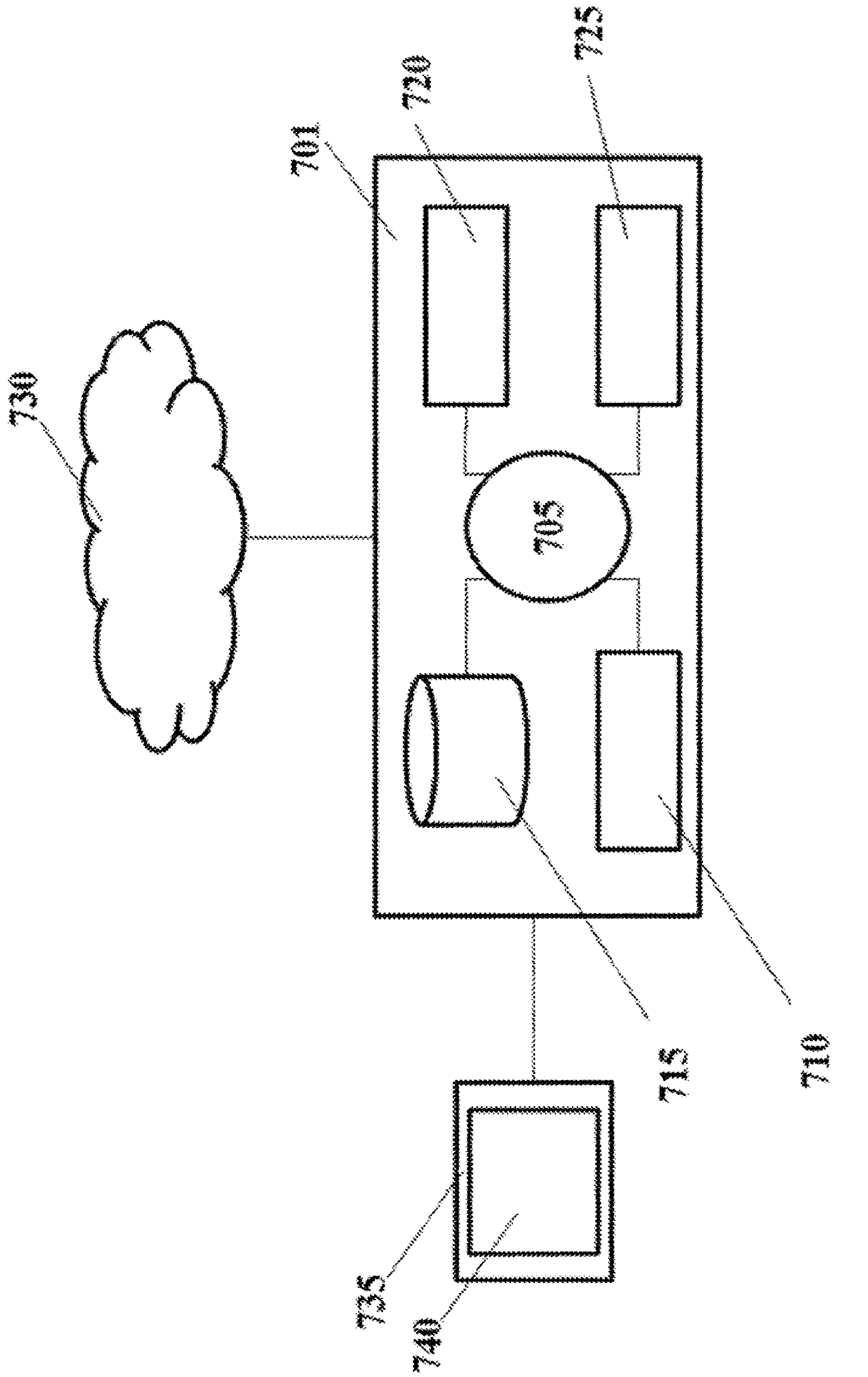
FIG. 7 illustrates a computer system programmed or otherwise configured to analyze genetic data.

The present disclosure provides computer control systems that are programmed to implement methods of the disclosure. FIG. 7 shows a computer system 701 that is programmed or otherwise configured to analyze genetic data. The methods described herein for detecting genetic variations below a detection limit may provide for more efficient processing of genetic data, thereby improving the functioning of a computer system. For example, the computer system may be able to process genetic data and identify a genetic variant more quickly or efficiently (e.g., no re-processing of the genetic data or processing of additional genetic data may be necessary if the computer system may identify the genetic variant below the detection limit).

The computer system 701 can regulate various aspects of detecting genetic variations below a noise range or detection limit of the present disclosure, such as, for example, detecting genetic variations in nucleic acid molecules, comparing sets of genetic variations, determining diagnostic confidence indications, determining confidence intervals, sequencing nucleic acids, including massively parallel sequencing, grouping sequence reads into families, collapsing grouped sequence reads, determining consensus sequences. The computer system 801 can be an electronic device of a user or a computer system that is remotely located with respect to the electronic device. The electronic device can be a mobile electronic device.

The computer system 701 includes a central processing unit (CPU, also "processor" and "computer processor" herein) 705, which can be a single core or multi core processor, or a plurality of processors for parallel processing. The computer system 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720 and peripheral devices 725 are in communication with the CPU 705 through a communication bus (solid lines), such as a motherboard. The storage unit 715 can be a data storage unit (or data repository) for storing data. The computer system 701 can be operatively coupled to a computer network ("network") 730 with the aid of the communication interface 720. The network 730 can be the Internet, an internet and/or extranet, or an intranet and/or extranet that is in communication with the Internet. The network 730 in some cases is a telecommunication and/or data network. The network 730 can include one or more computer servers, which can enable distributed computing, such as cloud computing. The network 730, in some cases with the aid of the computer system 701, can implement a peer-to-peer network, which may enable devices coupled to the computer system 701 to behave as a client or a server.

The CPU 705 can execute a sequence of machine-readable instructions, which can be embodied in a program or software. The instructions may be stored in a memory location, such as the memory 710. The instructions can be directed to the CPU 705, which can subsequently program or otherwise configure the CPU 705 to implement methods of the present disclosure. Examples of operations performed by the CPU 705 can include fetch, decode, execute, and writeback.

The CPU 705 can be part of a circuit, such as an integrated circuit. One or more other components of the system 701 can be included in the circuit. In some cases, the circuit is an application specific integrated circuit (ASIC).

The storage unit 715 can store files, such as drivers, libraries and saved programs. The storage unit 715 can store user data, e.g., user preferences and user programs. The computer system 701 in some cases can include one or more additional data storage units that are external to the computer system 701, such as located on a remote server that is in communication with the computer system 701 through an intranet or the Internet.

The computer system 701 can communicate with one or more remote computer systems through the network 730. For instance, the computer system 701 can communicate with a remote computer system of a user (e.g., a physician, a laboratory technician, a genetic counselor, a scientist, among others). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 701 via the network 730.

Methods as described herein can be implemented by way of machine (e.g., computer processor) executable code stored on an electronic storage location of the computer system 701, such as, for example, on the memory 710 or electronic storage unit 715. The machine executable or machine readable code can be provided in the form of software. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 701 can include or be in communication with an electronic display 735 that comprises a user interface (UI) 740 for providing, for example, personal or individualized patient reports identifying genomic variations or alterations, which may include tumor specific genomic alterations and associated treatment options. Examples of UI's include, without limitation, a graphical user interface (GUI) and web-based user interface. Data generated and displayed using a user interface (740) may be accessed by a user, such as a healthcare professional, laboratory technician, genetic counselor, or a scientist, on the network.

Methods and systems of the present disclosure can be implemented by way of one or more algorithms. An algorithm can be implemented by way of software upon execution by the central processing unit 705. The algorithm can, for example, sequence nucleic acids (e.g. massively parallel sequencing), group nucleic acid sequences, collapse grouped nucleic acid sequences, generate consensus sequences, detect genetic variations, update diagnostic confidence intervals, annotate sequences, generate reports, and execute other processes which may comprise one or more of the following: Hidden Markov Model, dynamic programming, Bayesian network, trellis decoding, Viterbi decoding, expectation maximization, Kalman filtering methodologies and neural networks.

The following examples are offered by way of illustration and not by way of limitation.

EXAMPLES

Figure 8:
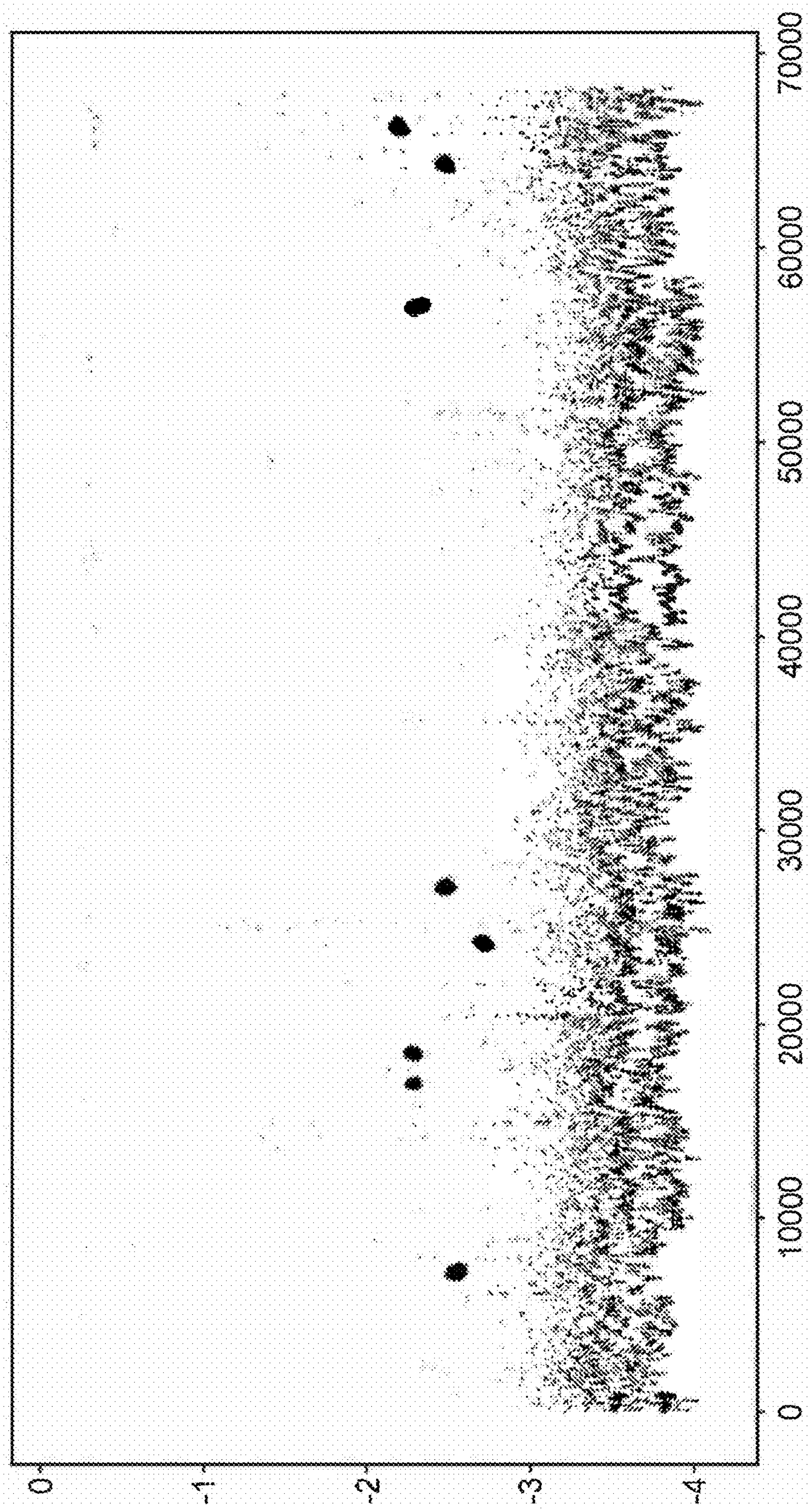
FIG. 8 shows detection of sequences in a sample spiked with nucleic acids bearing cancer mutants.

FIG. 8 shows a graph of frequency of detected base changes (compared to a reference genome) in a DNA sample along 70 kb of sequence of a plurality of oncogenes amplified and sequenced using protocols appropriate for Illumine sequencing. The sample was spiked with a low percentage of control DNA carrying sequence variants at known locations.

These variants are represented by dark circles. Variants occurring at log 0 (100%) or log −0.3 (0.5 or 50%) represent homozygous or heterozygous loci. Variants at less than log −2 (less than 1%) occur in the noise range of this system, and may represent sequencing errors (noise) or actual variants (information). For any variant detected in the noise range, it may not be possible to determine whether the variant represents noise or information. Amid the "noise", one has diminished confidence that base calls at the mutant positions represent information (actual mutants) rather than noise. However, if the control DNA is spiked into a second sample, it should appear again at a similar frequency. In contrast, the probability that an error is detected at the same locus again is a function of the error rate, and is less likely to be seen. The independent detection of the same variant increases the probability that information, rather than noise, is being detected, and provides increased confidence that a diagnosis of cancer is a correct one.

To the extent a sequencing error is the result of chance, the probability of detecting the same sequencing error multiple times can be exponentially smaller than detecting it a single time. Thus, if a particular signal is detected multiple times, it is more probably information rather than noise. This characteristic can be used to increase the probability that a genetic variant detected at low level represents an actual polynucleotide or set of polynucleotides, rather than a sequencing artifact.

In one example, a signal indicating a pathology is detected in a plurality of instances. In certain embodiments, the signal is a polynucleotide bearing a somatic mutation associated with cancer or a copy number variation associated with cancer. Repeated detection of the signal increases the probability that the signal represents information rather than noise. The repeated instances include, without limitation, (1) repeated testing of the same sample, (2) testing of two samples taken at the same time from a subject or (3) testing of two samples taken at different times from a subject. Determining increased probability is particularly useful when the first detected signal is at a level that cannot be reliably differentiated from noise. The methods of this disclosure find use, among other things, in monitoring a subject over time for early detection of pathology, for example, when repeated testing detects pathology at levels which, in a single test, are too low to reliably make a diagnosis of pathology.

In another example describing co-variate variants associated with lung cancer, a signal associated with a detected high confidence variation is detected below the detection limit. If EGFR L858R activating mutation is detected, the detection threshold for a co-variate resistance mutation, EGFR T790M resistance mutation, is relaxed. The independent detection of the activating or driver mutation increases confidence that a co-variate variate within the detection threshold is also detected.

Methods and systems of the present disclosure may be combined with other methods and systems, such as, for example, those described in Patent Cooperation Treaty (PCT) Patent Publication Nos. WO/2014/039556, WO/2014/149134, WO/2015/100427 and WO/2015/175705, each of which is entirely incorporated herein by reference.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method comprising:

(a) ligating molecular barcodes to a first plurality of cell-free DNA (cfDNA) molecules, wherein the first plurality of cfDNA molecules are from a first cell-free biological sample from a subject;

(b) ligating molecular barcodes to a second plurality of cfDNA molecules, wherein the second plurality of cfDNA molecules are from a second cell-free biological sample from the subject;

(c) generating genetic data using a genetic analyzer, wherein the genetic data relates to sequence information of the subject and wherein the ligated molecular barcodes track back to particular polynucleotides;

(d) storing the genetic data received from the genetic analyzer in computer memory as (i) first genetic data corresponding to the first cell-free biological sample and (ii) second genetic data corresponding to the second cell-free biological sample, each as one or more memory-resident genetic data objects associated with the molecular barcodes;

(e) comparing the genetic data from the first cell-free biological sample to the genetic data from the second cell-free biological sample to produce an adjusted test result, wherein the adjusted test result comprises a modification of a previously stored diagnostic confidence value associated with the genetic data based upon whether the genetic data from the first cell-free biological sample corroborates or conflicts with the genetic data from the second cell-free biological sample, and wherein the comparing comprises updating, in the computer memory, a diagnostic confidence value associated with the genetic data based on the corroboration or conflict, wherein corroboration comprises detecting a same genetic variant at a corresponding genomic position in both the first genetic data and the second genetic data, and wherein the corroboration enables identification of the genetic variant at a frequency below a per-base error rate or noise threshold of the genetic analyzer; and (f) outputting the adjusted test result into computer memory, wherein the adjusted test result comprises the updated diagnostic confidence value stored in association with the genetic data for use in a subsequent characterization of sequence information of the subject, wherein the subsequent characterization comprises generating a later diagnostic determination of a disease state using the updated diagnostic confidence value.

2. The method of claim 1, wherein the genetic data comprises sequence reads included in the second genetic data and sequence reads included in the first genetic data, and wherein (e) comprises comparing the sequence reads included in the second genetic data with the and sequence reads included in the first genetic data and updating a diagnostic confidence value stored in the computer memory with respect to the characterization of the genetic sequence information of the subject, which diagnostic confidence value is indicative of a probability of identifying one or more genetic variations in the first or second cell-free biological sample of the subject.

3. The method of claim 2, further comprising generating a confidence interval associated with the diagnostic confidence value stored in the computer memory.

4. The method of claim 3, further comprising comparing numerical values of the confidence interval associated with the diagnostic confidence value with numerical values of one or more prior confidence intervals stored in the computer memory and determining a disease progression based on numerical overlap of the confidence intervals.

5. The method of claim 1:

wherein the first and second cell-free biological samples are obtained at two or more time points including a first time point and a second time point, and wherein step (e) comprises increasing the diagnostic confidence value stored in the computer memory for the subsequent characterization performed after the updating of the diagnostic confidence value if the information from the first time point corroborates information from the second time point.

6. The method of claim 1:

wherein the first and second cell-free biological samples are obtained at two or more time points including a first time point and a second time point, and wherein step (e) comprises increasing the diagnostic confidence value stored in the computer memory in the subsequent characterization if the information from the first time point corroborates information from the second time point.

7. The method of claim 1:

wherein a first co-variate variation is detected in at least one of the first genetic data or the second genetic data, and wherein step (e) comprises increasing the diagnostic confidence value stored in the computer memory in the subsequent characterization if a second co-variate variation is detected.

8. The method of claim 1:

wherein the first and second cell-free biological samples are obtained at two or more time points including a first time point and a second time point, and wherein step (e) comprises decreasing the diagnostic confidence value stored in the computer memory in the subsequent characterization if the information from a first time point conflicts with information from the second time point.

9. The method of claim 1, further comprising:

obtaining a subsequent characterization; and leaving as is the diagnostic confidence value stored in the computer memory in the subsequent characterization for de novo information.

10. The method of claim 1, further comprising:

determining a frequency of one or more genetic variants detected in a collection of sequence reads included in the first genetic data and the second genetic data; and producing the adjusted test result at least in part by comparing the frequency of the one or more genetic variants at a first time point associated with the first cell-free biological sample and a second time point associated with the second cell-free biological sample.

11. The method of claim 1, further comprising:

determining an amount of copy number variation at one or more genetic loci detected in a collection of sequence reads included in the first genetic data and the second genetic data; and producing the adjusted test result at least in part by comparing the amount of copy number variation at a first time point associated with the first cell-free biological sample and a second time point associated with the second cell-free biological sample.

12. The method of claim 1, further comprising using the adjusted test result to provide (i) a therapeutic intervention or (ii) a diagnosis of a health or disease to the subject.

13. The method of claim 1, wherein the genetic data comprises sequence data from portions of a genome comprising disease-associated or cancer-associated genetic variants.

14. The method of claim 1, further comprising using the adjusted test result to increase a sensitivity of detecting genetic variants by increasing read depth of polynucleotides in the first cell-free biological sample or the second cell-free biological sample from the subject.

15. The method of claim 1, wherein the genetic data comprises the first genetic data and the second genetic data, wherein the first genetic data is at or below a detection threshold and the second genetic data is above the detection threshold.

16. The method of claim 15, wherein the detection threshold is a noise threshold.

17. The method of claim 15, further comprising, in step (e), adjusting a diagnosis of the subject from negative or uncertain to positive when the same genetic variants are detected in the first genetic data and the second genetic data in a plurality of sampling instances or time points.

18. The method of claim 1, wherein the disease state is cancer and the genetic analyzer is a nucleic acid sequencer.

19. The method of claim 1, wherein the first and second cell-free biological samples include a same type of biological sample.

20. The method of claim 19, wherein the first and second cell-free biological samples are blood samples.

21. The method of claim 1, wherein step (a) comprises:

spiking control DNA into the first and second cell-free biological samples; and calculating an error rate for the first and second cell-free biological samples.

22. The method of claim 1, wherein the molecular barcodes and the corresponding first and second genetic data for the first and second cell-free biological samples are represented as string identifiers stored in computer memory, each string identifier associated with a subset of the first and second genetic data.

23. The method of claim 22, further comprising parsing the string identifiers stored in computer memory by one or more processors that access the memory to read sequence characters of the string identifiers and extract tag information used to associate corresponding portions of the genetic data represented in the computer memory.

24. The method of claim 1, further comprising normalizing the first and second genetic data from the first and second cell-free biological samples by adjusting sequence-read counts according to a per-base error rate determined from control DNA spiked into the samples before performing the comparison of the genetic data.

25. The method of claim 1, wherein the comparing comprises executing machine-readable instructions that:

access data objects corresponding to the first and second genetic data stored in the computer memory for the first and second cell-free biological samples; and update the diagnostic confidence value in the memory based on consistency of the first and second genetic data between the samples.

26. The method of claim 1, wherein the molecular barcodes uniquely tag polynucleotides in the cfDNA molecules to generate tagged cfDNA molecules.

27. The method of claim 1, further comprising:

generating a plurality of sequencing reads from the tagged cfDNA molecules; and grouping sequence reads into families, each family generated from a uniquely tagged parent polynucleotide.

* * * * *